United States Patent
Wilson et al.

(10) Patent No.: US 10,975,140 B2
(45) Date of Patent: *Apr. 13, 2021

(54) COMPOSITIONS COMPRISING AAV EXPRESSING DUAL ANTIBODY CONSTRUCTS AND USES THEREOF

(71) Applicant: The Trustees of the University of Pennsylvania, Philadelphia, PA (US)

(72) Inventors: James M. Wilson, Philadelphia, PA (US); Anna Tretiakova, Philadelphia, PA (US)

(73) Assignee: The Trustees of the University of Pennsylvania, Blue Bell, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/821,295

(22) Filed: Mar. 17, 2020

(65) Prior Publication Data

US 2020/0216520 A1    Jul. 9, 2020

Related U.S. Application Data

(63) Continuation of application No. 16/460,623, filed on Jul. 2, 2019, now Pat. No. 10,647,758, which is a continuation of application No. 16/160,040, filed on Oct. 15, 2018, now Pat. No. 10,385,119, which is a continuation of application No. 15/310,555, filed as application No. PCT/US2015/030533 on May 13, 2015, now Pat. No. 10,138,295.

(60) Provisional application No. 61/992,649, filed on May 13, 2014.

(51) Int. Cl.
| | |
|---|---|
| *C12N 15/11* | (2006.01) |
| *A61K 48/00* | (2006.01) |
| *C12N 9/22* | (2006.01) |
| *C12N 15/86* | (2006.01) |
| *C12N 15/90* | (2006.01) |
| *C07K 16/10* | (2006.01) |
| *C12N 7/00* | (2006.01) |
| *A61K 39/00* | (2006.01) |

(52) U.S. Cl.
CPC ...... *C07K 16/1018* (2013.01); *A61K 48/0008* (2013.01); *C12N 7/00* (2013.01); *C12N 15/86* (2013.01); *A61K 2039/507* (2013.01); *C07K 2317/14* (2013.01); *C07K 2317/31* (2013.01); *C07K 2317/51* (2013.01); *C07K 2317/515* (2013.01); *C07K 2317/52* (2013.01); *C07K 2317/622* (2013.01); *C12N 2750/14121* (2013.01); *C12N 2750/14143* (2013.01); *C12N 2830/205* (2013.01); *C12N 2830/30* (2013.01); *C12N 2830/50* (2013.01); *C12N 2840/203* (2013.01)

(58) Field of Classification Search
CPC .......... A61P 35/00; C12N 9/22; C12N 15/86; C12N 2310/20; C12N 2750/14143
See application file for complete search history.

(56) References Cited

U.S. PATENT DOCUMENTS

| | | |
|---|---|---|
| 5,139,941 A | 8/1992 | Muzyczka et al. |
| 5,741,683 A | 4/1998 | Zhou et al. |
| 5,811,524 A | 9/1998 | Brams et al. |
| 5,891,994 A | 4/1999 | Goldstein |
| 5,972,596 A | 10/1999 | Pavlakis et al. |
| 6,057,152 A | 5/2000 | Samulski et al. |
| 6,193,981 B1 | 2/2001 | Goldstein |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter |
| 6,660,514 B1 | 12/2003 | Zolotukhin et al. |
| 6,780,639 B1 | 8/2004 | Chtarto et al. |
| 6,951,753 B2 | 10/2005 | Shenk et al. |

(Continued)

FOREIGN PATENT DOCUMENTS

| | | |
|---|---|---|
| CN | 1668636 A | 9/2005 |
| CN | 1981039 A | 6/2007 |
| CN | 101649328 A | 2/2010 |
| CN | 102791866 A | 11/2012 |
| CN | 103261220 A | 8/2013 |

(Continued)

OTHER PUBLICATIONS

Alexander et al., "Insulin stimulates glyceraldehyde-3-phosphate dehydrogenase gene expression through cis-acting DNA sequences." Proceedings of the National Academy of Sciences 85.14 (1988): 5092-5096. (Jul. 1988).

(Continued)

*Primary Examiner* — Barry A Chestnut
(74) *Attorney, Agent, or Firm* — Howson and Howson LLP; Cathy Kodroff

(57) ABSTRACT

A recombinant adeno-associated virus (AAV) having an AAV capsid and packaged therein a heterologous nucleic acid which expresses two functional antibody constructs in a cell is described. Also described are antibodies comprising a heavy chain and a light chain from a heterologous antibody. In one embodiment, the antibodies are co-expressed from a vector containing: a first expression cassette which encodes at least a first open reading frame (ORF) for a first immunoglobulin under the control of regulatory control sequences which direct expression thereof; and a second expression cassette which comprises a second ORF, a linker, and a third ORF under the control of regulatory control sequences which direct expression thereof, wherein the second and third ORF for a second and third immunoglobulin construct. The vector co-expressing these two antibody constructs is in one embodiment an AAV, in which the 5' and 3' ITRs flank the expression cassettes and regulatory sequences.

17 Claims, 8 Drawing Sheets

Specification includes a Sequence Listing.

(56) References Cited

U.S. PATENT DOCUMENTS

| | | |
|---|---|---|
| 7,094,604 B2 | 8/2006 | Snyder et al. |
| 7,125,717 B2 | 10/2006 | Carter |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,442,373 B2 | 10/2008 | Morrow et al. |
| 7,465,583 B2 | 12/2008 | Samulski et al. |
| 7,588,772 B2 | 9/2009 | Kay et al. |
| 7,790,449 B2 | 9/2010 | Gao et al. |
| 7,906,111 B2 | 3/2011 | Wilson et al. |
| 8,187,601 B2 | 5/2012 | Weng et al. |
| 9,198,984 B2 | 12/2015 | Lock et al. |
| 10,138,295 B2 | 11/2018 | Wilson et al. |
| 10,385,119 B2 | 8/2019 | Wilson et al. |
| 2006/0136184 A1 | 6/2006 | Gustafsson et al. |
| 2006/0159673 A1 | 7/2006 | Kojima |
| 2011/0065779 A1 | 3/2011 | Fanng et al. |
| 2011/0076265 A1 | 3/2011 | Burioni et al. |
| 2011/0236353 A1 | 9/2011 | Wilson et al. |
| 2012/0232133 A1 | 9/2012 | Balazs et al. |
| 2012/0282695 A1 | 11/2012 | Blain et al. |
| 2014/0032186 A1 | 1/2014 | Gustafsson et al. |
| 2014/0037637 A1 | 2/2014 | McNally et al. |
| 2014/0065666 A1 | 3/2014 | Simpson et al. |
| 2014/0094392 A1 | 4/2014 | Bowers et al. |
| 2014/0127749 A1 | 5/2014 | Mason et al. |

FOREIGN PATENT DOCUMENTS

| | | |
|---|---|---|
| CN | 103492574 A | 1/2014 |
| CN | 103764831 A | 4/2014 |
| JP | 2001-523971 T | 11/1998 |
| JP | 2006-515503 T | 6/2006 |
| JP | 2008-506389 T | 3/2008 |
| JP | 2009-532025 T | 9/2009 |
| JP | 2012-515540 T | 7/2012 |
| WO | WO-1999/016884 | 4/1999 |
| WO | WO-2001/054719 | 8/2001 |
| WO | WO-98/50431 | 11/2001 |
| WO | WO-2003/042397 | 5/2003 |
| WO | WO-2004/009618 A2 | 1/2004 |
| WO | WO-2004-065611 | 8/2004 |
| WO | WO-2005/033321 | 4/2005 |
| WO | WO-2005/108568 A1 | 11/2005 |
| WO | WO-2006/017325 | 2/2006 |
| WO | WO-2006/110689 | 10/2006 |
| WO | WO-2007/126798 | 11/2007 |
| WO | WO-2008/156763 | 12/2008 |
| WO | WO-2009/115972 | 9/2009 |
| WO | WO-2010/010466 | 1/2010 |
| WO | WO-2010/084197 | 7/2010 |
| WO | WO-2010/111367 A1 | 9/2010 |
| WO | WO-2010/130636 | 11/2010 |
| WO | WO-2010/140114 | 12/2010 |
| WO | WO-2010/151673 A1 | 12/2010 |
| WO | WO-2010/119991 A3 | 1/2011 |
| WO | WO-2011/097603 A1 | 8/2011 |
| WO | WO-2011/126868 | 10/2011 |
| WO | WO-2011/143318 A2 | 11/2011 |
| WO | WO-2011/160119 A2 | 12/2011 |
| WO | WO-2012/020006 A2 | 2/2012 |
| WO | WO-2012/023053 A2 | 2/2012 |
| WO | WO-2012/123430 A1 | 9/2012 |
| WO | WO-2012/125124 A1 | 9/2012 |
| WO | WO-2012/138975 A1 | 10/2012 |
| WO | WO-2012/145572 A1 | 10/2012 |
| WO | WO-2013/046704 | 4/2013 |
| WO | WO-2013/049492 | 4/2013 |
| WO | WO-2013/059206 A2 | 4/2013 |
| WO | WO-2013/076186 | 5/2013 |
| WO | WO-2013/155222 | 10/2013 |
| WO | WO-2013/163427 A1 | 10/2013 |
| WO | WO-2015/012924 | 1/2015 |
| WO | WO-2015/142661 A1 | 9/2015 |
| WO | WO-2015/175639 A1 | 11/2015 |

OTHER PUBLICATIONS

Amara et al, "Control of a mucosal challenge and prevention of AIDS by a multiprotein DNA/MVA vaccine." Science 292.5514 (2001): 69-74. (Apr. 6, 2001).

An et al, "Active retrotransposition by a synthetic L1 element in mice." Proceedings of the National Academy of Sciences 103.49 (2006): 18662-18667. (Epub Nov. 21, 2006.).

Andersson et al, "An atlas of active enhancers across human cell types and tissues." Nature 507.7493 (2014): 455-461. (Published online Mar. 26, 2014).

Barouch et al, "Elicitation of high-frequency cytotoxic T-lymphocyte responses against both dominant and subdominant simian-human immunodeficiency virus epitopes by DNA vaccination of rhesus monkeys." Journal of virology 75.5 (2001): 2462-2467. (Mar. 2001).

Brinster et al. "Regulation of metallothionein—thymidine kinase fusion plasmids injected into mouse eggs." (1982): 39-42. (Mar. 4, 1982).

Buning et al., 2008, "Recent developments in adeno-associated virus vector technology," J. Gene Med. 10:717-733 (Jul. 2008).

Choi et al. AAV hybrid serotypes: improved vectors for gene delivery. Curr Gene Ther. Jun. 2005;5(3):299-310. (Jun. 2005).

Ercolani et al., "Isolation and complete sequence of a functional human glyceraldehyde-3-phosphate dehydrogenase gene." Journal of Biological Chemistry 263.30 (1988): 15335-15341. (Oct. 25, 1988).

Gossen et al, "Tight control of gene expression in mammalian cells by tetracycline-responsive promoters." Proceedings of the National Academy of Sciences 89.12 (1992): 5547-5551. (Jun. 1992).

Grieger et al. "Adeno-associated virus as a gene therapy vector: Vector development, production and clinical applications," Adv. Biochem. Engin/Biotechnol. 99: 119-145 (Oct. 2005).

Grieger et al. "Packaging capacity of adeno-associated virus serotypes: impact of larger genomes on infectivity and postentry steps." Journal of virology 79.15 (2005): 9933-9944. (Aug. 2005).

Grieger et al. "Separate basic region motifs within the adeno-associated virus capsid proteins are essential for infectivity and assembly." Journal of virology 80.11 (2006): 5199-5210. (Jun. 2006).

Lai Chng et al., "Antisense RNA complementary to 3'coding and noncoding sequences of creatine kinase is a potent inhibitor of translation in vivo." Proceedings of the National Academy of Sciences 86.24 (1989): 10006-10010. (Dec. 1989).

Levitt et al, "Definition of an efficient synthetic poly (A) site." Genes & Development 3.7 (1989): 1019-1025. (Jul. 1989).

Lewis, Ad, et al. Generation of Neutralizing Activity against Human Immunodeficiency Virus Type 1 in Serum by Antibody Gene Transfer, J Virol. Sep. 2002;76(17):8769-75.

Mayo et al. "The mouse metallothionein-I gene is transcriptionally regulated by cadmium following transfection into human or mouse cells." Cell 29.1 (1982): 99-108.

McCarty et al, "Self-complementary recombinant adeno-associated virus (scAAV) vectors promote efficient transduction independently of DNA synthesis", Gene Therapy, Aug. 2001, vol. 8, No. 16, pp. 1248-1254 (Aug. 2001).

Medicines in Development Biologics, 2013 Report, pp. 1-87, a publication of PhRMA's Communications & Public Affairs Department. (202) 835-3460 (Feb. 7, 2013).

Ng et al. "Regulation of the human β-actin promoter by upstream and intron domains." Nucleic acids research 17.2 (1989): 601-615. (Jan. 25, 1989).

Quitschke et al, "The beta actin promoter. High levels of transcription depend upon a CCAAT binding factor." Journal of Biological Chemistry 264.16 (1989): 9539-9546. (Jun. 5, 1989).

Radcliffe et al, "Multiple gene products from a single vector:'self-cleaving'2A peptides." Gene Therapy 11.23 (2004): 1673-1673.

(56) References Cited

OTHER PUBLICATIONS

Sawada-Hirai et al, "Human anti-anthrax protective antigen neutralizing monoclonal antibodies derived from donors vaccinated with anthrax vaccine adsorbed." Journal of immune based therapies and vaccines 2.1 (2004): 5 . . . (on-line May 12, 2004).
Scharfmann et al., "Long-term in vivo expression of retrovirus-mediated gene transfer in mouse fibroblast implants." Proceedings of the National Academy of Sciences 88.11 (1991): 4626-4630. (Jun. 1, 1991).
Searle et al. "Building a metal-responsive promoter with synthetic regulatory elements." Molecular and Cellular Biology 5.6 (1985): 1480-1489. (Jun. 1985).
Sui et al, "Structural and functional bases for broad-spectrum neutralization of avian and human influenza A viruses." Nature structural & molecular biology 16.3 (2009): 265-273. (Mar. 2009).
Thomson et al, Nucl. Acids. Res., "A comprehensive comparison of multiple sequence alignments", 27(13):2682-2690 (1999). (Jul. 1, 1999).
Xia et al, "siRNA-mediated gene silencing in vitro and in vivo." Nature biotechnology 20.10 (2002): 1006-1010. Epub Sep. 16, 2002.
Zhang et al., 2009, "Adenovirus-adeno-associated virus hybrid for large-scale recombinant adeno-associated virus production," Human Gene Therapy 20:922-929 (Jul. 20, 2009).
Wang et al, Efficiency of Exendin-4 expression mediated by a recombinant double-stranded adeno-associated virus vector in treatment of diabetic rats. Acta Academiae Medicinae Militaris Tertiae, vol. 35, No. 17, pp. 1831-1835, Sep. 15, 2013.
Aurnhammer et al., Universal real-time PCR for the detection and quantification of adeno-associated virus serotype 2-derived inverted terminal repeat sequences. Hum Gene Ther Methods. Feb. 2012;23(1):18-28. (Published Online: Jun. 2011).
Platt et al., CRISPR-Cas9 knockin mice for genome editing and cancer modeling. Cell. Oct. 9, 2014;159(2):440-55. doi: 10.1016/j.cell.2014.09.014. Epub Sep. 25, 2014.
Yan et al., Inverted terminal repeat sequences are important for intermolecular recombination and circularization of adeno-associated virus genomes. J Virol. Jan. 2005;79(1):364-79. (Published online Dec. 13, 2004).
International Search Report and Written Opinion of the International Searching Authority/US issued on PCT/US2015/030533 dated Aug. 14, 2015.
Drug Information of Pertuzumab (Accession No. DB06366) retrieved from: https://www.drugbank.ca/drugs/DB06366 on Jan. 25, 2017.
Drug Information of Trastuzumab (Accession No. DB00072 (BTD00098, BIOD00098)) retrieved from: https://www.drugbank.ca/drugs/DB00072 on Jan. 25, 2017.
Office Action issued in the counterpart Colombian Patent Application No. NC2016/0005185, dated Mar. 21, 2018, with unofficial translation.
Office Action issued in the counterpart Chinese Patent Application No. 201580024949.8 dated Dec. 28, 2018, with unofficial translation provided by the Chinese Agent.
Office Action issued in the counterpart Chilean Patent Application No. 2840-2016 dated Nov. 24, 2017, with unofficial translation provided by the Chilean Agent.
Office Action issued in the counterpart Chilean Patent Application No. 2840-2016 dated Aug. 21, 2018, with unofficial translation provided by the Chilean Agent.
Office Action issued in the counterpart Eurasian Patent Application No. 201692293 dated Aug. 31, 2018, with unofficial translation provided by the Eurasian Agent.
Office Action issued in the counterpart Eurasian Patent Application No. 201692293/28 dated Apr. 10, 2019 with an unofficial English translation provided by the Agent.
Response dated Jun. 29, 2017 filed in the counterpart European Patent Application No. 15792528.0 in reply to a Communication pursuant to Rules 161(1) and 162 EPC inviting Applicant to amend the application.
Extended European Search Report issued in the counterpart European Patent Application No. 15792528.0 dated Sep. 20, 2017.
Communication pursuant to Rules 70(2) and 70a(2) EPC issued in the counterpart European Patent Application No. 15792528.0 dated Oct. 9, 2017.
Response dated Apr. 19, 2018 in reply to the Oct. 9, 2017 Communication in the counterpart European Patent Application No. 15792528.0.
Communication pursuant to Article 94(3) EPC issued in the counterpart European Patent Application No. 15792528.0 dated Feb. 7, 2019.
Response dated Aug. 10, 2019 in reply to the Feb. 7, 2019 Communication in the counterpart European Patent Application No. 15792528.0.
Office Action issued in the counterpart Indonesian Patent Application No. P00201607356 dated Feb. 19, 2019 with an unofficial English translation provided by the Indonesian Patent Agent.
Office Action issued in the counterpart Indonesian Patent Application No. P00201607356 dated Jul. 30, 2019 with an unofficial English translation provided by the Indonesian Patent Agent.
Office Action issued in the counterpart Israeli Patent Application No. 248508 dated Dec. 2, 2018 with unofficial translation provided by the Israeli Agent.
Office Action issued in the counterpart Japanese Patent Application No. 2016-567604 dated Mar. 19, 2019 with an unofficial English translation provided by the Agent.
Office Action issued in the counterpart Moroccan Patent Application No. PV/39437 dated Dec. 2, 2018 with unofficial translation provided by the Moroccan Agent.
First Office Action issued in the counterpart Mexican Patent Application No. MX/a/2016/014813, dated Mar. 9, 2018, with unofficial translation.
Second Office Action issued in the counterpart Mexican Patent Application No. MX/a/2016/014813, dated Aug. 13, 2018, with unofficial translation.
Office Action issued in the counterpart Panamanian Patent Application No. 91414 dated Nov. 24, 2017 with an unofficial English translation provided by Panamanian Agent.
Restriction Requirement issued in the parent U.S. Appl. No. 15/310,555 dated Jul. 28, 2017.
Response dated Sep. 20, 2017 to the Jul. 28, 2017 Restriction Requirement in the parent U.S. Appl. No. 15/310,555.
Non-Final Office Action issued in the parent U.S. Appl. No. 15/310,555 dated Oct. 4, 2017.
Response dated Mar. 5, 2018 in reply to the Oct. 4, 2017 Non-Final Office Action issued in the parent U.S. Appl. No. 15/310,555.
Office Action issued in the counterpart Patent Application in Philippines with Application No. 1/2016/502239 mailed by the Intellectual Property Office of the Philippines Bureau of Patents dated Nov. 18, 2019.
Office Action issued in the counterpart Eurasian Patent Application No. 201692293/28 dated Nov. 25, 2019 with an unofficial English translation provided by the local Agent.
Office Action issued in the counterpart Patent Application in China with Application No. 201580024949.8 mailed by the Chinese State Intellectual Property Office dated Dec. 4, 2019 with an unofficial English translation provided by the local Agent.
Office Action issued in counterpart Israeli Patent Application No. 248508 dated Mar. 1, 2020, with an unofficial English translation provided by the local Agent.
Search Report issued in counterpart United Arab Emirates Patent Application No. P6000282/16, dated Apr. 20, 2020.
Office Action dated Jul. 1, 2020 issued in corresponding Chinese Patent Application No. 201580024949.8, with local translation provided by Agent.
Substantive Examination Report dated Jul. 29, 2020 issued in corresponding Malaysian Patent Application No. PI 2016001938.
Response dated Aug. 2, 2019 in reply to the Mar. 19, 2019 Communication in the counterpart Japanese Patent Application No. 2016-567604.
Final Office Action issued in the counterpart Japanese Patent Application No. 2016-567604 dated Jan. 22, 2020 with an unofficial English translation provided by the Agent.

(56) References Cited

OTHER PUBLICATIONS

Response of an appeal dated May 22, 2020 filed to the Jan. 22, 2020 Office Action issued in the counterpart Japanese Patent Application No. 2016-567604.

Office Action issued in the counterpart Ukrainian Patent Application No. a2016 12601 dated Jun. 17, 2020 with an unofficial English translation provided by the Agent.

Japanese Patent Application No. 202005017AH which was derived from Japanese Patent Application No. 2016-567604, filed May 22, 2020.

Office Action issued in the counterpart Japanese Patent Application No. 202005017AH dated Jun. 17, 2020 with an unofficial English translation provided by the Agent.

Pre-trial Reexamination Report Issued in the counterpart Japanese Patent Application No. 2016-567604 dated Jul. 29, 2020 with an unofficial English translation thereof provided by Agent.

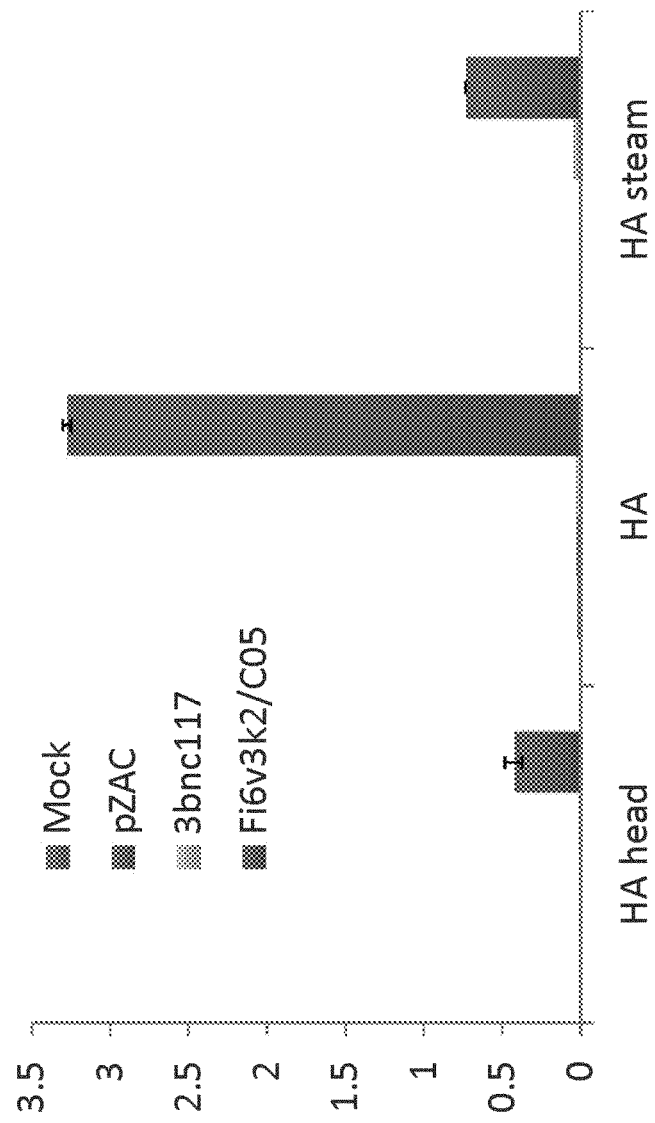

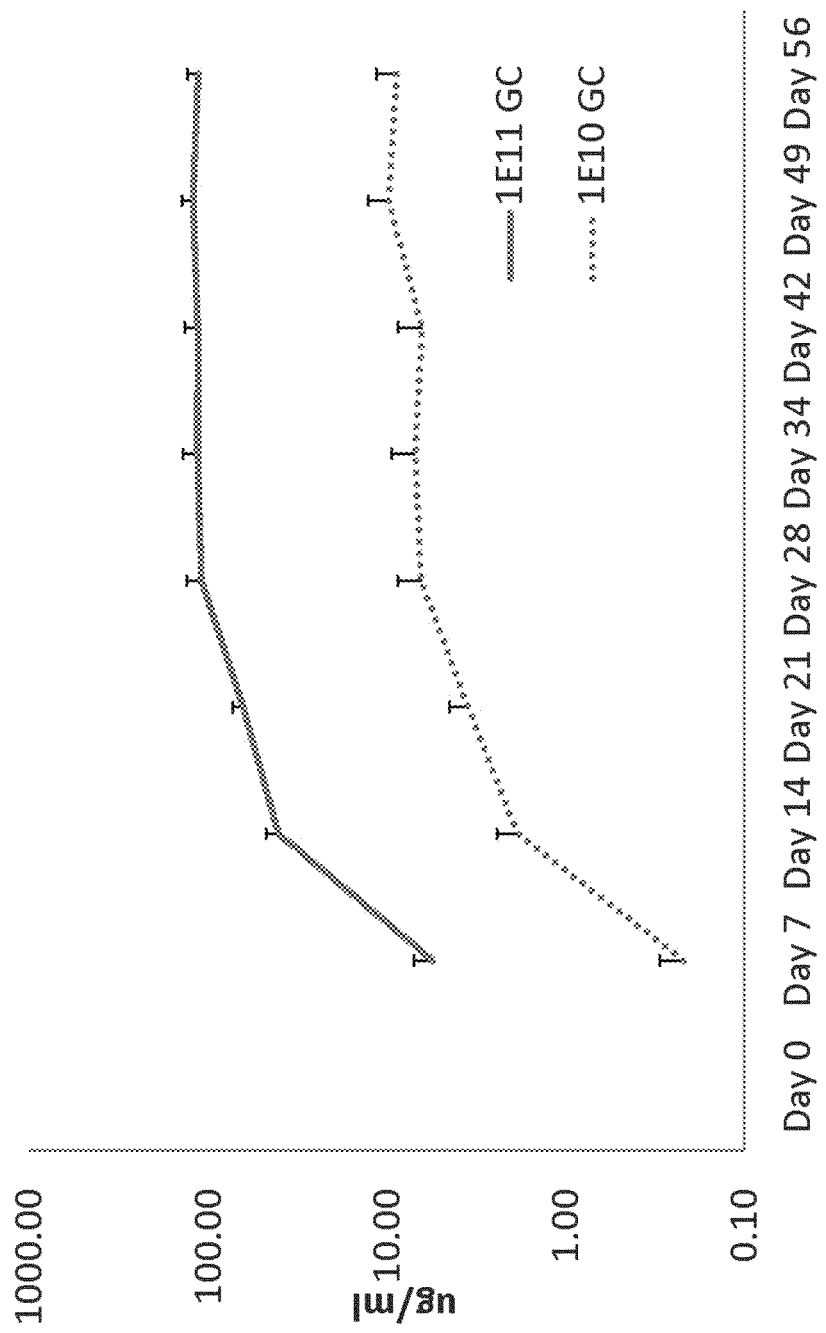

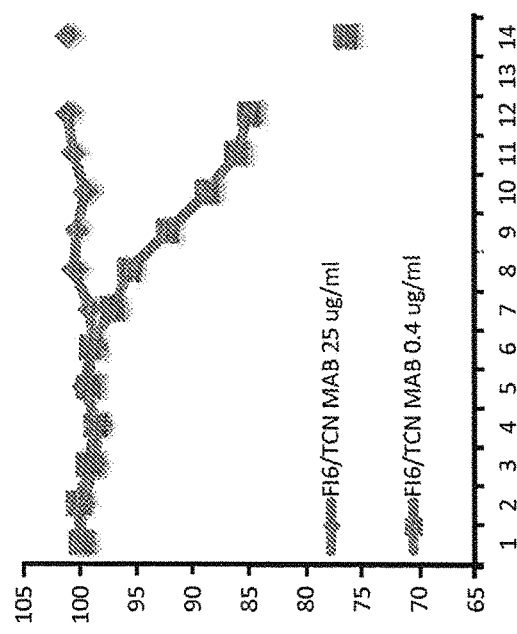
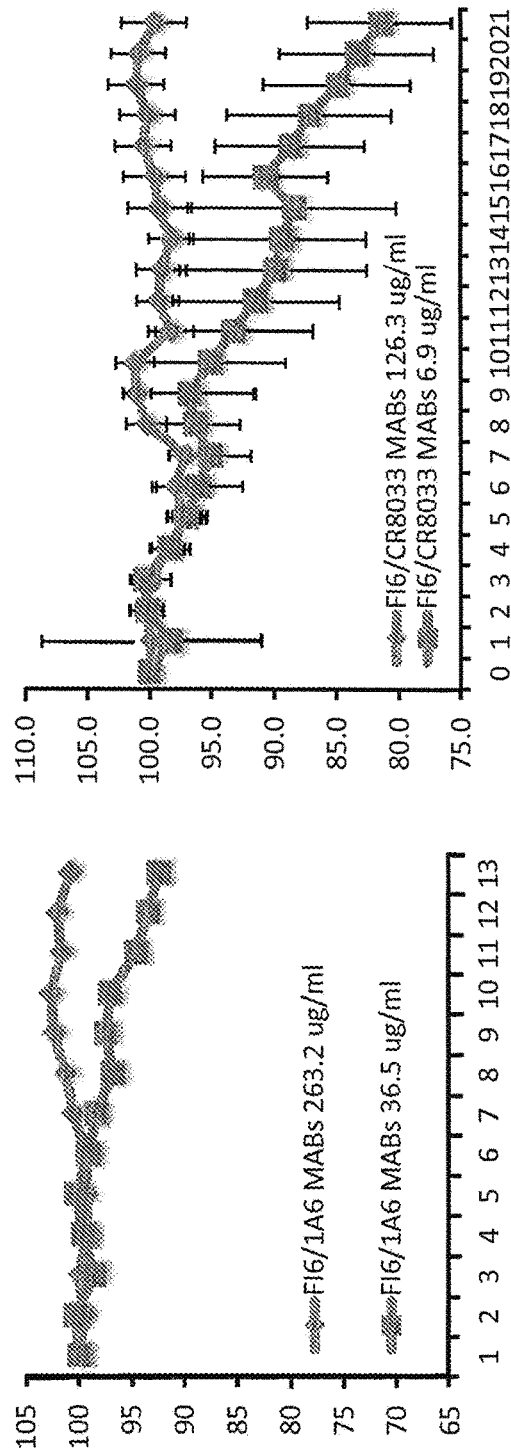
FIG 8A
FIG 8B
FIG 8C

SEQUENCE LISTING

<160> NUMBER OF SEQ ID NOS: 50

<210> SEQ ID NO 1
<211> LENGTH: 705
<212> TYPE: DNA
<213> ORGANISM: Artificial sequence
<220> FEATURE:
<223> OTHER INFORMATION: Synthetic sequence encoding FI6 heavy chain
<220> FEATURE:
<221> NAME/KEY: CDS
<222> LOCATION: (1)..(705)
<223> OTHER INFORMATION: FI6 constant

<400> SEQUENCE: 1

```
gcg gcg cct aag agc tgc gac aag acc cac acc tgt ccc ccc tgc cct      48
Ala Ala Pro Lys Ser Cys Asp Lys Thr His Thr Cys Pro Pro Cys Pro
1               5                   10                  15 gcc cct gaa ctg ctg gga ggc ccc agc gtg ttc ctg ttc ccc cca aag      96
Ala Pro Glu Leu Leu Gly Gly Pro Ser Val Phe Leu Phe Pro Pro Lys
            20                  25                  30 ccc aag gac acc ctg atg atc agc cgg acc ccc gaa gtg acc tgc gtg     144
Pro Lys Asp Thr Leu Met Ile Ser Arg Thr Pro Glu Val Thr Cys Val
        35                  40                  45 gtg gtg gac gtg tcc cac gag gac cct gaa gtg aag ttc aat tgg tac     192
Val Val Asp Val Ser His Glu Asp Pro Glu Val Lys Phe Asn Trp Tyr
    50                  55                  60 gtg gac ggc gtg gaa gtg cac aac gcc aag acc aag ccc aga gag gaa     240
Val Asp Gly Val Glu Val His Asn Ala Lys Thr Lys Pro Arg Glu Glu
65                  70                  75                  80 cag tac aac agc acc tac cgg gtg gtg tcc gtg ctg acc gtg ctg cac     288
Gln Tyr Asn Ser Thr Tyr Arg Val Val Ser Val Leu Thr Val Leu His
                85                  90                  95 cag gac tgg ctg aac ggc aaa gag tac aag tgc aag gtg tcc aac aag     336
Gln Asp Trp Leu Asn Gly Lys Glu Tyr Lys Cys Lys Val Ser Asn Lys
            100                 105                 110 gcc ctg cct gcc ccc atc gag aaa acc atc agc aag gcc aag ggc cag     384
Ala Leu Pro Ala Pro Ile Glu Lys Thr Ile Ser Lys Ala Lys Gly Gln
        115                 120                 125 ccc cgc gag cct cag gtg tgc aca ctg ccc ccc agc cgg gaa gag atg     432
Pro Arg Glu Pro Gln Val Cys Thr Leu Pro Pro Ser Arg Glu Glu Met
    130                 135                 140 acc aag aac cag gtg tcc ctg acc tgc ctg gtc aag ggc ttc tac ccc     480
Thr Lys Asn Gln Val Ser Leu Thr Cys Leu Val Lys Gly Phe Tyr Pro
145                 150                 155                 160 agc gat atc gcc gtg gaa tgg gag agc aac ggc cag ccc gag aac aac     528
Ser Asp Ile Ala Val Glu Trp Glu Ser Asn Gly Gln Pro Glu Asn Asn
                165                 170                 175 tac aag acc acc ccc cct gtg ctg gac agc gac ggc tca ttc ttc ctg     576
Tyr Lys Thr Thr Pro Pro Val Leu Asp Ser Asp Gly Ser Phe Phe Leu
            180                 185                 190 tac agc aag ctg acc gtg gac aag agc cgg tgg cag cag ggc aac gtg     624
Tyr Ser Lys Leu Thr Val Asp Lys Ser Arg Trp Gln Gln Gly Asn Val
        195                 200                 205 ttc agc tgc agc gtg atg cac gag gcc ctg cac aac cac tac acc cag     672
Phe Ser Cys Ser Val Met His Glu Ala Leu His Asn His Tyr Thr Gln
    210                 215                 220 aag tcc ctg agc ctg agc ccc ggc aag tga tga                         705
Lys Ser Leu Ser Leu Ser Pro Gly Lys
225                 230
```

```
<210> SEQ ID NO 2
<211> LENGTH: 233
<212> TYPE: PRT
<213> ORGANISM: Artificial sequence
<220> FEATURE:
<223> OTHER INFORMATION: Synthetic Construct

<400> SEQUENCE: 2

Ala Ala Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Cys Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 3
<211> LENGTH: 7722
<212> TYPE: DNA
<213> ORGANISM: Artificial sequence
<220> FEATURE:
<223> OTHER INFORMATION: plasmid carrying FI6 and 1A6 antibodies
<220> FEATURE:
<221> NAME/KEY: polyA_signal
<222> LOCATION: (191)..(239)
<223> OTHER INFORMATION: synthetic\polyA
<220> FEATURE:
<221> NAME/KEY: misc_feature
<222> LOCATION: (246)..(914)
<223> OTHER INFORMATION: complement - CH'2-3
<220> FEATURE:
<221> NAME/KEY: misc_feature
<222> LOCATION: (915)..(1235)
<223> OTHER INFORMATION: complement - CH'1
<220> FEATURE:
<221> NAME/KEY: misc_feature
<222> LOCATION: (1236)..(1598)
<223> OTHER INFORMATION: complement - 1A6\VH
```

```
<220> FEATURE:
<221> NAME/KEY: misc_feature
<222> LOCATION: (1599)..(1655)
<223> OTHER INFORMATION: complement - leader
<220> FEATURE:
<221> NAME/KEY: misc_feature
<222> LOCATION: (1734)..(2202)
<223> OTHER INFORMATION: Enhancer
<220> FEATURE:
<221> NAME/KEY: misc_feature
<222> LOCATION: (2388)..(2444)
<223> OTHER INFORMATION: leader
<220> FEATURE:
<221> NAME/KEY: CDS
<222> LOCATION: (2445)..(2777)
<223> OTHER INFORMATION: FI6\VL
<220> FEATURE:
<221> NAME/KEY: misc_feature
<222> LOCATION: (3183)..(3242)
<223> OTHER INFORMATION: leader
<220> FEATURE:
<221> NAME/KEY: CDS
<222> LOCATION: (3243)..(3629)
<223> OTHER INFORMATION: FI6\VH
<220> FEATURE:
<221> NAME/KEY: CDS
<222> LOCATION: (3630)..(3950)
<223> OTHER INFORMATION: CH1
<220> FEATURE:
<221> NAME/KEY: CDS
<222> LOCATION: (3951)..(4619)
<223> OTHER INFORMATION: CH2-3
<220> FEATURE:
<221> NAME/KEY: polyA_signal
<222> LOCATION: (4626)..(4703)
<223> OTHER INFORMATION: TKpAshort
<220> FEATURE:
<221> NAME/KEY: misc_feature
<222> LOCATION: (6995)..(7283)
<223> OTHER INFORMATION: COL\E1\Origin

<400> SEQUENCE: 3
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctacgta gccatgctct    180
aggaagatct cacacaaaaa accaacacac agatgtaatg aaaataaaga tattttattt     240
tatcacttcc cggggctcag gctcagggac ttctgggtgt agtggttgtg cagggcctcg    300
tgcatcacgc tgcagctgaa cacgttgccc tgctgccacc ggctcttgtc cacggtcagc    360
ttgctataca ggaagaatga gccgtcgctg tccagcacag ggggggtggt cttgtagttg    420
ttctcgggct ggccgttgct ctcccattcc acggcgatct cgctggggta gaagcccttg    480
accaggcagg tcaggacac ctggttcttg gtcatctctt cccggctggg gggcagtgtg     540
tagacctgag gctcgcgggg ctggcccttg gccttgctga tggttttctc gatgggggca    600
ggcagggcct tgttggacac cttgcacttg tactctttgc cgttcagcca gtcctggtgc    660
agcacggtca gcacggacac cacccggtag gtgctgttgt actgttcctc tctgggcttg    720
gtcttggcgt tgtgcacttc cacgccgtcc acgtaccaat tgaacttcac ttcagggtcc    780
tcgtgggaca cgtccaccac cacgcaggtc acttcggggg tccggctgat catcaggtg     840 tccttgggct ttgggggggaa caggaacacg ctggggcctc ccagcagttc aggggcaggg    900
caggggggac acgtgtgggt cttgtcgcag ctcttaggtt ccaccgctt gtccaccttg     960 gtgttgctgg gcttgtggtt cacgttgcag atgtaggtct gggtgccag gctgctgctg     1020 ggcacggtga ccacgctgct caggctatac aggccgctgc tctgcagcac ggctggaaag   1080
```

-continued

```
gtgtgcacgc cgctggtcag ggcgccagag ttccaggaca cggtcacggg ctcggggaag    1140
tagtccttga ccaggcagcc cagggcggct gttccgccag aggtgctctt gctgctaggg    1200
gccagaggga acacgcttgg tcccttggtg ctggcgctcg agacggtcac cagggttccc    1260
tgtccccagt aatccattcc tccgctggcg attccgctcc gatccttggc gcagtagtac    1320
acggcggtat cctcggcccg caggctgttc atctgcaggt acagggtgtt cttgctgttg    1380
gcccggctga tggtgaaccg tcccttcacg ctatcggcgt agtacttgtt gtttccatcg    1440
tagctgatca cggccaccca ctccagtccc tttcctgggg cctgccgcac ccagtgcatt    1500
ccgtaatcgc tgaaggtgaa tccgctggcg gcgcagctca gccgcaggct ccgtcctggc    1560
tgcaccactc ctcctccgct ctcctgcagc tgcacctgtg aattcgtcac cagggccagg    1620
ctcagggcga tcagcagcag cagctgcatg cgcatggtgg cggcgcgatc tgacggttca    1680
ctaaacgagc tctgcttata taggcctccc accgtacacg ccacctcgac atacctagtt    1740
attaatagta atcaattacg gggtcattag ttcatagccc atatatggag ttccgcgtta    1800
cataacttac ggtaaatggc ccgcctggct gaccgcccaa cgacccccgc ccattgacgt    1860
caataatgac gtatgttccc atagtaacgc caatagggac tttccattga cgtcaatggg    1920
tggagtattt acggtaaact gcccacttgg cagtacatca agtgtatcat atgccaagta    1980
cgccccctat tgacgtcaat gacggtaaat ggcccgcctg gcattatgcc cagtacatga    2040
ccttatggga ctttcctact tggcagtaca tctacgtatt agtcatcgct attaccatgg    2100
tgatgcggtt ttggcagtac atcaatgggc gtggatagcg gtttgactca cggggatttc    2160
caagtctcca ccccattgac gtcaatggga gtttgttttg gcaccaaaat caacgggact    2220
ttccaaaatg tcgtaacaac tccgccccat tgacgcaaat gggcggtagg cgtgtacggt    2280
gggaggtcta tataagcaga gctggtttag tgaaccgtca gatccgctgg cactttgca    2340 ctggaactta caacacccga gcaaggacgc gactctgccg ccccaccatg cgcatgcagc    2400
tgctgctgct gatcgccctg agcctggccc tggtgaccaa cagc gat atc gtc atg    2456
                                                Asp Ile Val Met
                                                 1 acc cag agc cca gat agc ctg gcc gtg agc ctg gga gag cgg gcc acc       2504
Thr Gln Ser Pro Asp Ser Leu Ala Val Ser Leu Gly Glu Arg Ala Thr
 5              10                  15                  20 atc aac tgc aag agc agc cag agc gtg acc ttc aac tac aag aac tac       2552
Ile Asn Cys Lys Ser Ser Gln Ser Val Thr Phe Asn Tyr Lys Asn Tyr
             25                  30                  35 ctg gcc tgg tac cag cag aag cca gga cag cca cca aag ctg ctg atc       2600
Leu Ala Trp Tyr Gln Gln Lys Pro Gly Gln Pro Pro Lys Leu Leu Ile
         40                  45                  50 tac tgg gcc agc acc cgg gag agc gga gtg cca gat cgg ttc agc gga       2648
Tyr Trp Ala Ser Thr Arg Glu Ser Gly Val Pro Asp Arg Phe Ser Gly
     55                  60                  65 agc gga agc gga acc gat ttc acc ctg acc atc agc agc ctg cag gcc       2696
Ser Gly Ser Gly Thr Asp Phe Thr Leu Thr Ile Ser Ser Leu Gln Ala
 70                  75                  80 gag gat gtg gcc gtg tac tac tgc cag cag cac tac cgg acc cca cca       2744
Glu Asp Val Ala Val Tyr Tyr Cys Gln Gln His Tyr Arg Thr Pro Pro
 85              90                  95                  100 acc ttc gga cag gga acc aag gtg gag atc aag cgtacggtgg ccgccccaag    2797
Thr Phe Gly Gln Gly Thr Lys Val Glu Ile Lys
                 105                 110 cgtgttcatc ttcccaccaa gcgatgagca gctgaagagc ggaaccgcca gcgtggtgtg    2857
cctgctgaac aacttctacc cacgggaggc caaggtgcag tggaaggtgg ataacgccct    2917
```

-continued

```
gcagagcgga aacagccagg agagcgtgac cgagcaggat agcaaggata gcacctacag    2977
cctgagcagc accctgaccc tgagcaaggc cgattacgag aagcacaagg tgtacgcctg    3037
cgaggtgacc caccagggac tgagcagccc agtgaccaag agcttcaacc gcggagagtg    3097
ccggaagcgg cgggcccag tgaagcagac cctgaacttc gatctgctga agctggccgg    3157
agatgtggag agcaacccag gaccaatgta cagaatgcag ctgctgagct gcatcgccct    3217
```

```
gagcctggcc ctggtgacca acagc cag gtg caa cta gtg gag agc gga gga    3269
                              Gln Val Gln Leu Val Glu Ser Gly Gly
                                          115                 120 gga gtg gtg cag cca gga cgg agc ctg cgg ctg agc tgc gcc gcc agc    3317
Gly Val Val Gln Pro Gly Arg Ser Leu Arg Leu Ser Cys Ala Ala Ser
            125                 130                 135 gga ttc acc ttc agc acc tac gcc atg cac tgg gtg cgg cag gcc cca    3365
Gly Phe Thr Phe Ser Thr Tyr Ala Met His Trp Val Arg Gln Ala Pro
            140                 145                 150 gga aag gga ctg gag tgg gtg gcc gtg atc agc tac gat gcc aac tac    3413
Gly Lys Gly Leu Glu Trp Val Ala Val Ile Ser Tyr Asp Ala Asn Tyr
        155                 160                 165 aag tac tac gcc gat agc gtg aag gga cgg ttc acc atc agc cgg gat    3461
Lys Tyr Tyr Ala Asp Ser Val Lys Gly Arg Phe Thr Ile Ser Arg Asp
    170                 175                 180 aac agc aag aac acc ctg tac ctg cag atg aac agc ctg cgg gcc gag    3509
Asn Ser Lys Asn Thr Leu Tyr Leu Gln Met Asn Ser Leu Arg Ala Glu
185                 190                 195                 200 gat acc gcc gtg tac tac tgc gcc aag gat agc cag ctg cgg agc ctg    3557
Asp Thr Ala Val Tyr Tyr Cys Ala Lys Asp Ser Gln Leu Arg Ser Leu
                205                 210                 215 ctg tac ttc gag tgg ctg agc cag gga tac ttc gat tac tgg gga cag    3605
Leu Tyr Phe Glu Trp Leu Ser Gln Gly Tyr Phe Asp Tyr Trp Gly Gln
            220                 225                 230 gga acc ctg gtg acc gtg agc agc gct agc acc aag gga cca agc gtg    3653
Gly Thr Leu Val Thr Val Ser Ser Ala Ser Thr Lys Gly Pro Ser Val
            235                 240                 245 ttc cca ctg gcc cca agc agc aag agc acc agc gga gga acc gcc gcc    3701
Phe Pro Leu Ala Pro Ser Ser Lys Ser Thr Ser Gly Gly Thr Ala Ala
    250                 255                 260 ctg gga tgc ctg gtg aag gat tac ttc cca gag cca gtg acc gtg agc    3749
Leu Gly Cys Leu Val Lys Asp Tyr Phe Pro Glu Pro Val Thr Val Ser
265                 270                 275                 280 tgg aac agc gga gcc ctg acc agc gga gtg cac acc ttc cca gcc gtg    3797
Trp Asn Ser Gly Ala Leu Thr Ser Gly Val His Thr Phe Pro Ala Val
                285                 290                 295 ctg cag agc agc gga ctg tat agc ctg agc agc gtg gtg acc gtg cca    3845
Leu Gln Ser Ser Gly Leu Tyr Ser Leu Ser Ser Val Val Thr Val Pro
            300                 305                 310 agc agc agc ctg gga acc cag acc tac atc tgc aac gtg aac cac aag    3893
Ser Ser Ser Leu Gly Thr Gln Thr Tyr Ile Cys Asn Val Asn His Lys
            315                 320                 325 cca agc aac acc aag gtg gat aag aag gtg gag cca aag agc tgc gat    3941
Pro Ser Asn Thr Lys Val Asp Lys Lys Val Glu Pro Lys Ser Cys Asp
        330                 335                 340 aag acc cac acg tgc cct cct tgt cca gcc ccc gaa ctg ctg ggc ggg    3989
Lys Thr His Thr Cys Pro Pro Cys Pro Ala Pro Glu Leu Leu Gly Gly
345                 350                 355                 360 cct agc gtg ttc ctg ttt ccc cct aag cct aaa gat aca ctg atg att    4037
Pro Ser Val Phe Leu Phe Pro Pro Lys Pro Lys Asp Thr Leu Met Ile
                365                 370                 375
```

| | | |
|---|---|---|
| agt aga acc cca gag gtc aca tgc gtg gtc gtg gac gtg tcc cac gaa<br>Ser Arg Thr Pro Glu Val Thr Cys Val Val Val Asp Val Ser His Glu<br>380                          385                       390 | | 4085 |
| gag cct gac gtg aag ttc aac tgg tac gtg gat ggc gtg gag gtg cac<br>Glu Pro Asp Val Lys Phe Asn Trp Tyr Val Asp Gly Val Glu Val His<br>         395                        400                       405 | | 4133 |
| aat gct aag act aaa cca cgc gaa gag cag tat aat agt aca tac cga<br>Asn Ala Lys Thr Lys Pro Arg Glu Glu Gln Tyr Asn Ser Thr Tyr Arg<br>410                          415                       420 | | 4181 |
| gtc gtg tca gtc ctg aca gtg ctg cac cag gat tgg ctg aac ggc aag<br>Val Val Ser Val Leu Thr Val Leu His Gln Asp Trp Leu Asn Gly Lys<br>425                        430                       435                      440 | | 4229 |
| gag tat aag tgc aag gtg tct aac aag gcc ctg ccc gcc cct atc gag<br>Glu Tyr Lys Cys Lys Val Ser Asn Lys Ala Leu Pro Ala Pro Ile Glu<br>                  445                       450                       455 | | 4277 |
| aaa aca att agc aag gcc aaa ggg cag cca cgg gaa ccc cag gtc tac<br>Lys Thr Ile Ser Lys Ala Lys Gly Gln Pro Arg Glu Pro Gln Val Tyr<br>                  460                       465                       470 | | 4325 |
| act ctg cca ccc tca aga gat gaa ctg act aag aac cag gtc agc ctg<br>Thr Leu Pro Pro Ser Arg Asp Glu Leu Thr Lys Asn Gln Val Ser Leu<br>475                        480                       485 | | 4373 |
| acc tgt ctg gtg aaa ggc ttc tac ccc agc gac atc gcc gtg gag tgg<br>Thr Cys Leu Val Lys Gly Phe Tyr Pro Ser Asp Ile Ala Val Glu Trp<br>490                        495                       500 | | 4421 |
| gaa agt aac ggc cag cct gag aat aac tac aag act acc cct cca gtg<br>Glu Ser Asn Gly Gln Pro Glu Asn Asn Tyr Lys Thr Thr Pro Pro Val<br>505                        510                       515                      520 | | 4469 |
| ctg gat agc gac ggg tcc ttc ttc ctg tat agc aag ctg aca gtg gac<br>Leu Asp Ser Asp Gly Ser Phe Phe Leu Tyr Ser Lys Leu Thr Val Asp<br>                  525                       530                       535 | | 4517 |
| aaa tcc cgc tgg cag cag gga aac gtc ttt tcc tgt tct gtg atg cat<br>Lys Ser Arg Trp Gln Gln Gly Asn Val Phe Ser Cys Ser Val Met His<br>540                        545                       550 | | 4565 |
| gag gcc ctg cac aat cat tac acc cag aag agt ctg tca ctg agc ccc<br>Glu Ala Leu His Asn His Tyr Thr Gln Lys Ser Leu Ser Leu Ser Pro<br>555                        560                       565 | | 4613 |
| ggc aaa tgataaaagg aacccgcgct atgacggcaa taaaaagaca gaataaaacc<br>Gly Lys<br>      570 | | 4669 |
| cacgggtgtt gggtcgtttg ttcataaacc cgggatcgat aaggatcttc ctagagcatg | | 4729 |
| gctacgtaga taagtagcat ggcgggttaa tcattaacta caaggaaccc ctagtgatgg | | 4789 |
| agttggccac tccctctctg cgcgctcgct cgctcactga ggccgggcga ccaaaggtcg | | 4849 |
| cccgacgccc gggctttgcc cggcggcct cagtgagcga gcgagcgcgc agccttaatt | | 4909 |
| aacctaattc actggccgtc gttttacaac gtcgtgactg ggaaaaccct ggcgttaccc | | 4969 |
| aacttaatcg ccttgcagca catccccctt cgccagctg gcgtaatagc gaagaggccc | | 5029 |
| gcaccgatcg cccttcccaa cagttgcgca gcctgaatgg cgaatgggac gcgccctgta | | 5089 |
| gcggcgcatt aagcgcggcg ggtgtggtgg ttacgcgcag cgtgaccgct acacttgcca | | 5149 |
| gcgccctagc gcccgctcct ttcgctttct tcccttcctt tctcgccacg ttcgccggct | | 5209 |
| ttccccgtca gctctaaat cggggctcc ctttagggtt ccgatttagt gctttacggc | | 5269 |
| acctcgaccc caaaaaactt gattagggtg atggttcacg tagtgggcca tcgccctgat | | 5329 |
| agacggtttt tcgcccttg acgttggagt ccacgttctt taatagtgga ctcttgttcc | | 5389 |
| aaactggaac aacactcaac cctatctcgg tctattcttt tgatttataa gggattttgc | | 5449 |
| cgatttcggc ctattggtta aaaatgagc tgatttaaca aaaatttaac gcgaatttta | | 5509 |

```
acaaaatatt aacgcttaca atttaggtgg cacttttcgg ggaaatgtgc gcggaacccc    5569
tatttgttta ttttttctaaa tacattcaaa tatgtatccg ctcatgagac aataaccctg   5629
ataaatgctt caataatatt gaaaaaggaa gagtatgagt attcaacatt tccgtgtcgc    5689
ccttattccc ttttttgcgg cattttgcct tcctgttttt gctcacccag aaacgctggt    5749
gaaagtaaaa gatgctgaag atcagttggg tgcacgagtg ggttacatcg aactggatct    5809
caacagcggt aagatccttg agagttttcg ccccgaagaa cgttttccaa tgatgagcac    5869
ttttaaagtt ctgctatgtg gcgcggtatt atcccgtatt gacgccgggc aagagcaact    5929
cggtcgccgc atacactatt ctcagaatga cttggttgag tactcaccag tcacagaaaa    5989
gcatcttacg gatggcatga cagtaagaga attatgcagt gctgccataa ccatgagtga    6049
taacactgcg gccaacttac ttctgacaac gatcggagga ccgaaggagc taaccgcttt    6109
tttgcacaac atgggggatc atgtaactcg ccttgatcgt tgggaaccgg agctgaatga    6169
agccatacca aacgacgagc gtgacaccac gatgcctgta gcaatggcaa caacgttgcg    6229
caaactatta actggcgaac tacttactct agcttcccgg caacaattaa tagactggat    6289
ggaggcggat aaagttgcag gaccacttct gcgctcggcc cttccggctg gctggtttat    6349
tgctgataaa tctggagccg gtgagcgtgg gtctcgcggt atcattgcag cactggggcc    6409
agatggtaag ccctcccgta tcgtagttat ctacacgacg gggagtcagg caactatgga    6469
tgaacgaaat agacagatcg ctgagatagg tgcctcactg attaagcatt ggtaactgtc    6529
agaccaagtt tactcatata tactttagat tgatttaaaa cttcattttt aatttaaaag    6589
gatctaggtg aagatccttt ttgataatct catgaccaaa atcccttaac gtgagttttc    6649
gttccactga gcgtcagacc ccgtagaaaa gatcaaagga tcttcttgag atccttttttt   6709
tctgcgcgta atctgctgct tgcaaacaaa aaaaccaccg ctaccagcgg tggtttgttt    6769
gccggatcaa gagctaccaa ctctttttcc gaaggtaact ggcttcagca gagcgcagat    6829
accaaatact gttcttctag tgtagccgta gttaggccac cacttcaaga actctgtagc    6889
accgcctaca tacctcgctc tgctaatcct gttaccagtg gctgctgcca gtggcgataa    6949
gtcgtgtctt accgggttgg actcaagacg atagttaccg gataaggcgc agcggtcggg    7009
ctgaacgggg ggttcgtgca cacagcccag cttggagcga acgacctaca ccgaactgag    7069
atacctacag cgtgagctat gagaaagcgc cacgcttccc gaagggagaa aggcggacag    7129
gtatccggta agcggcaggg tcggaacagg agagcgcacg agggagcttc caggggggaaa   7189
cgcctggtat ctttatagtc ctgtcgggtt tcgccacctc tgacttgagc gtcgattttt    7249
gtgatgctcg tcagggggggc ggagcctatg gaaaaacgcc agcaacgcgg cctttttacg    7309
gttcctggcc ttttgctggc cttttgctca catgttcttt cctgcgttat ccctgattc     7369
tgtggataac cgtattaccg cctttgagtg agctgatacc gctcgccgca gccgaacgac    7429
cgagcgcagc gagtcagtga gcgaggaagc ggaagagcgc ccaatacgca aaccgcctct    7489
ccccgcgcgt tggccgattc attaatgcag ctggcacgac aggtttcccg actggaaagc    7549
gggcagtgag cgcaacgcaa ttaatgtgag ttagctcact cattaggcac cccaggcttt    7609
acactttatg cttccggctc gtatgttgtg tggaattgtg agcggataac aatttcacac    7669
aggaaacagc tatgaccatg attacgccag atttaattaa ggccttaatt agg          7722
```

<210> SEQ ID NO 4
<211> LENGTH: 111
<212> TYPE: PRT
<213> ORGANISM: Artificial sequence
<220> FEATURE:
<223> OTHER INFORMATION: Synthetic Construct

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 5
<211> LENGTH: 129
<212> TYPE: PRT
<213> ORGANISM: Artificial sequence
<220> FEATURE:
<223> OTHER INFORMATION: Synthetic Construct

<400> SEQUENCE: 5

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 6
<211> LENGTH: 107
<212> TYPE: PRT
<213> ORGANISM: Artificial sequence
<220> FEATURE:
<223> OTHER INFORMATION: Synthetic Construct

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His
            100                 105

<210> SEQ ID NO 7
<211> LENGTH: 223
<212> TYPE: PRT
<213> ORGANISM: Artificial sequence
<220> FEATURE:
<223> OTHER INFORMATION: Synthetic Construct

<400> SEQUENCE: 7

Thr Cys Pro Pro Cys Pro Ala Pro Glu Leu Leu Gly Gly Pro Ser Val
  1               5                  10                  15

Phe Leu Phe Pro Pro Lys Pro Lys Asp Thr Leu Met Ile Ser Arg Thr
             20                  25                  30

Pro Glu Val Thr Cys Val Val Val Asp Val Ser His Glu Glu Pro Asp
         35                  40                  45

Val Lys Phe Asn Trp Tyr Val Asp Gly Val Glu Val His Asn Ala Lys
     50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 8
<211> LENGTH: 7773
<212> TYPE: DNA
<213> ORGANISM: Artificial sequence
<220> FEATURE:
<223> OTHER INFORMATION: Plasmid encoding FI6 and C05 monoclonal
      antibodies
<220> FEATURE:
<221> NAME/KEY: polyA_signal
<222> LOCATION: (204)..(252)
<223> OTHER INFORMATION: synthetic\polyA
```

```
<220> FEATURE:
<221> NAME/KEY: misc_feature
<222> LOCATION: (259)..(927)
<223> OTHER INFORMATION: complement - CH'2-3
<220> FEATURE:
<221> NAME/KEY: misc_feature
<222> LOCATION: (928)..(1248)
<223> OTHER INFORMATION: complement - CH'1
<220> FEATURE:
<221> NAME/KEY: misc_feature
<222> LOCATION: (1251)..(1668)
<223> OTHER INFORMATION: complement - C05\VH
<220> FEATURE:
<221> NAME/KEY: misc_feature
<222> LOCATION: (1669)..(1719)
<223> OTHER INFORMATION: complement - leader
<220> FEATURE:
<221> NAME/KEY: misc_feature
<222> LOCATION: (1729)..(1979)
<223> OTHER INFORMATION: complement - CMV\mp2
<220> FEATURE:
<221> NAME/KEY: misc_feature
<222> LOCATION: (1798)..(2266)
<223> OTHER INFORMATION: Enhancer
<220> FEATURE:
<221> NAME/KEY: misc_feature
<222> LOCATION: (2267)..(2392)
<223> OTHER INFORMATION: CMV\mp2
<220> FEATURE:
<221> NAME/KEY: CDS
<222> LOCATION: (2509)..(2841)
<223> OTHER INFORMATION: FI6\VL
<220> FEATURE:
<221> NAME/KEY: CDS
<222> LOCATION: (2842)..(3162)
<223> OTHER INFORMATION: CL
<220> FEATURE:
<221> NAME/KEY: misc_feature
<222> LOCATION: (3247)..(3306)
<223> OTHER INFORMATION: leader
<220> FEATURE:
<221> NAME/KEY: CDS
<222> LOCATION: (3307)..(3693)
<223> OTHER INFORMATION: FI6\VH
<220> FEATURE:
<221> NAME/KEY: CDS
<222> LOCATION: (3694)..(4014)
<223> OTHER INFORMATION: CH1
<220> FEATURE:
<221> NAME/KEY: CDS
<222> LOCATION: (4015)..(4683)
<223> OTHER INFORMATION: CH2-3
<220> FEATURE:
<221> NAME/KEY: polyA_signal
<222> LOCATION: (4690)..(4767)
<223> OTHER INFORMATION: TKpAshort

<400> SEQUENCE: 8
ggccttaatt aggctgcgcg ctcgctcgct cactgaggcc gcccgggcaa agcccgggcg      60
tcgggcgacc tttggtcgcc cggcctcagt gagcgagcga gcgcgcagag agggagtggc     120
caactccatc actaggggtt ccttgtagtt aatgattaac ccgccatgct acttatctac     180
gtagccatgc tctaggaaga tctcacacaa aaaaccaaca cacagatgta atgaaaataa     240
agatatttta ttttatcact tcccggggct caggctcagg gacttctggg tgtagtggtt     300
gtgcagggcc tcgtgcatca cgctgcagct gaacacgttg ccctgctgcc accggctctt     360
gtccacggtc agcttgctat acaggaagaa tgagccgtcg ctgtccagca caggggggt     420 ggtcttgtag ttgttctcgg gctggccgtt gctctcccat tccacggcga tctcgctggg     480
gtagaagccc ttgaccaggc aggtcaggga cacctggttc ttggtcatct cttcccggct     540 gggggggcagt gtgtagacct gaggctcgcg gggctggccc ttggccttgc tgatggtttt     600
```

-continued

| | |
|---|---|
| ctcgatgggg gcaggcaggg ccttgttgga caccttgcac ttgtactctt tgccgttcag | 660 |
| ccagtcctgg tgcagcacgg tcagcacgga caccacccgg taggtgctgt tgtactgttc | 720 |
| ctctctgggc ttggtcttgg cgttgtgcac ttccacgccg tccacgtacc aattgaactt | 780 |
| cacttcaggt tcctcgtggg acacgtccac caccacgcag gtcacttcgg gggtccggct | 840 |
| gatcatcagg gtgtccttgg gctttggggg gaacaggaac acgctggggc ctcccagcag | 900 |
| ttcaggggca gggcagggg gacacgtgtg ggtcttgtcg cagctcttag gttccacccg | 960 |
| cttgtccacc ttggtgttgc tgggcttgtg gttcacgttg cagatgtagg tctgggtgcc | 1020 |
| caggctgctg ctgggcacgg tgaccacgct gctcaggcta acaggccgc tgctctgcag | 1080 |
| cacggctgga aggtgtgca cgccgctggt cagggcgcca gagttccagg acacggtcac | 1140 |
| gggctcgggg aagtagtcct tgaccaggca gcccagggcg gctgttccgc cagaggtgct | 1200 |
| cttgctgcta ggggccagag ggaacacgct tggtcccttg gtgctggcgc tcgagacggt | 1260 |
| caccagggtt ccctgtcccc acacatcgaa ggcatctccc accagatcgg cccgctccca | 1320 |
| tccggcgctc accacctgct gcatggacat gtgcttggcg cagtagtaca ctccggtatc | 1380 |
| ctccacccgc aggttggtca tctgcaggta cagggtctcc ttgctgttat cccggctgat | 1440 |
| ggtgaaccgt ccctccacgc tatcggcgta atcaatgtct cctcctccgg cgttgatgat | 1500 |
| gctcagccac tccagtccct ttcctggggc ctgccgcacc cagctcacgg cgtagtagct | 1560 |
| cagggtgctc tctccgaagc tgcttccgct tcccacgcag ctcagccgca ggctctctcc | 1620 |
| tggctgcacc agtcctcctc cgctctcctg cagctgcacc tgtgaattcg tcaccagggc | 1680 |
| caggctcagg gcgatcagca gcagcagctg catgcgcatg gtggcggcgc gatctgacgg | 1740 |
| ttcactaaac gagctctgct tatataggcc tcccaccgta cacgccacct cgacatacct | 1800 |
| agttattaat agtaatcaat tacggggtca ttagttcata gcccatatat ggagttccgc | 1860 |
| gttacataac ttacggtaaa tggcccgcct ggctgaccgc ccaacgaccc ccgcccattg | 1920 |
| acgtcaataa tgacgtatgt tcccatagta acgccaatag ggactttcca ttgacgtcaa | 1980 |
| tgggtggagt atttacggta aactgcccac ttggcagtac atcaagtgta tcatatgcca | 2040 |
| agtacgcccc ctattgacgt caatgacggt aaatggcccg cctggcatta tgcccagtac | 2100 |
| atgaccttat gggactttcc tacttggcag tacatctacg tattagtcat cgctattacc | 2160 |
| atggtgatgc ggttttggca gtacatcaat gggcgtggat agcggtttga ctcacgggga | 2220 |
| tttccaagtc tccaccccat tgacgtcaat gggagtttgt tttggcacca aaatcaacgg | 2280 |
| gactttccaa aatgtcgtaa caactccgcc ccattgacgc aaatgggcgg taggcgtgta | 2340 |
| cggtgggagg tctatataag cagagctggt ttagtgaacc gtcagatccg ctgggcactt | 2400 |
| tgcactggaa cttacaacac ccgagcaagg acgcgactct gccgccccac catgcgcatg | 2460 |
| cagctgctgc tgctgatcgc cctgagcctg gccctggtga ccaacagc gat atc gtc | 2517 |
| | Asp Ile Val |
| | 1 |
| atg acc cag agc cca gat agc ctg gcc gtg agc ctg gga gag cgg gcc | 2565 |
| Met Thr Gln Ser Pro Asp Ser Leu Ala Val Ser Leu Gly Glu Arg Ala | |
| 5 10 15 | |
| acc atc aac tgc aag agc agc cag agc gtg acc ttc aac tac aag aac | 2613 |
| Thr Ile Asn Cys Lys Ser Ser Gln Ser Val Thr Phe Asn Tyr Lys Asn | |
| 20 25 30 35 | |
| tac ctg gcc tgg tac cag cag aag cca gga cag cca cca aag ctg ctg | 2661 |
| Tyr Leu Ala Trp Tyr Gln Gln Lys Pro Gly Gln Pro Pro Lys Leu Leu | |
| 40 45 50 | |

-continued

| | |
|---|---|
| atc tac tgg gcc agc acc cgg gag agc gga gtg cca gat cgg ttc agc<br>Ile Tyr Trp Ala Ser Thr Arg Glu Ser Gly Val Pro Asp Arg Phe Ser<br>                   55                  60                  65 | 2709 |
| gga agc gga agc gga acc gat ttc acc ctg acc atc agc agc ctg cag<br>Gly Ser Gly Ser Gly Thr Asp Phe Thr Leu Thr Ile Ser Ser Leu Gln<br>    70                  75                  80 | 2757 |
| gcc gag gat gtg gcc gtg tac tac tgc cag cag cac tac cgg acc cca<br>Ala Glu Asp Val Ala Val Tyr Tyr Cys Gln Gln His Tyr Arg Thr Pro<br>85                  90                  95 | 2805 |
| cca acc ttc gga cag gga acc aag gtg gag atc aag cgt acg gtg gcc<br>Pro Thr Phe Gly Gln Gly Thr Lys Val Glu Ile Lys Arg Thr Val Ala<br>100               105               110               115 | 2853 |
| gcc cca agc gtg ttc atc ttc cca cca agc gat gag cag ctg aag agc<br>Ala Pro Ser Val Phe Ile Phe Pro Pro Ser Asp Glu Gln Leu Lys Ser<br>                   120               125               130 | 2901 |
| gga acc gcc agc gtg gtg tgc ctg ctg aac aac ttc tac cca cgg gag<br>Gly Thr Ala Ser Val Val Cys Leu Leu Asn Asn Phe Tyr Pro Arg Glu<br>         135                 140               145 | 2949 |
| gcc aag gtg cag tgg aag gtg gat aac gcc ctg cag agc gga aac agc<br>Ala Lys Val Gln Trp Lys Val Asp Asn Ala Leu Gln Ser Gly Asn Ser<br>               150               155               160 | 2997 |
| cag gag agc gtg acc gag cag gat agc aag gat agc acc tac agc ctg<br>Gln Glu Ser Val Thr Glu Gln Asp Ser Lys Asp Ser Thr Tyr Ser Leu<br>165               170               175 | 3045 |
| agc agc acc ctg acc ctg agc aag gcc gat tac gag aag cac aag gtg<br>Ser Ser Thr Leu Thr Leu Ser Lys Ala Asp Tyr Glu Lys His Lys Val<br>180               185               190               195 | 3093 |
| tac gcc tgc gag gtg acc cac cag gga ctg agc agc cca gtg acc aag<br>Tyr Ala Cys Glu Val Thr His Gln Gly Leu Ser Ser Pro Val Thr Lys<br>               200               205               210 | 3141 |
| agc ttc aac cgc gga gag tgc cggaagcggc gggccccagt gaagcagacc<br>Ser Phe Asn Arg Gly Glu Cys<br>215 | 3192 |
| ctgaacttcg atctgctgaa gctggccgga gatgtggaga gcaacccagg accaatgtac | 3252 |
| agaatgcagc tgctgagctg catcgccctg agcctggccc tggtgaccaa cagc cag<br>                                                                                                              Gln | 3309 |
| gtg caa cta gtg gag agc gga gga gga gtg gtg cag cca gga cgg agc<br>Val Gln Leu Val Glu Ser Gly Gly Gly Val Val Gln Pro Gly Arg Ser<br>220               225               230               235 | 3357 |
| ctg cgg ctg agc tgc gcc gcc agc gga ttc acc ttc agc acc tac gcc<br>Leu Arg Leu Ser Cys Ala Ala Ser Gly Phe Thr Phe Ser Thr Tyr Ala<br>               240               245               250 | 3405 |
| atg cac tgg gtg cgg cag gcc cca gga aag gga ctg gag tgg gtg gcc<br>Met His Trp Val Arg Gln Ala Pro Gly Lys Gly Leu Glu Trp Val Ala<br>255               260               265 | 3453 |
| gtg atc agc tac gat gcc aac tac aag tac tac gcc gat agc gtg aag<br>Val Ile Ser Tyr Asp Ala Asn Tyr Lys Tyr Tyr Ala Asp Ser Val Lys<br>         270                 275               280 | 3501 |
| gga cgg ttc acc atc agc cgg gat aac agc aag aac acc ctg tac ctg<br>Gly Arg Phe Thr Ile Ser Arg Asp Asn Ser Lys Asn Thr Leu Tyr Leu<br>285               290               295 | 3549 |
| cag atg aac agc ctg cgg gcc gag gat acc gcc gtg tac tac tgc gcc<br>Gln Met Asn Ser Leu Arg Ala Glu Asp Thr Ala Val Tyr Tyr Cys Ala<br>300               305               310               315 | 3597 |
| aag gat agc cag ctg cgg agc ctg ctg tac ttc gag tgg ctg agc cag<br>Lys Asp Ser Gln Leu Arg Ser Leu Leu Tyr Phe Glu Trp Leu Ser Gln<br>               320               325               330 | 3645 |

```
gga tac ttc gat tac tgg gga cag gga acc ctg gtg acc gtg agc agc         3693
Gly Tyr Phe Asp Tyr Trp Gly Gln Gly Thr Leu Val Thr Val Ser Ser
            335                 340                 345 gct agc acc aag gga cca agc gtg ttc cca ctg gcc cca agc agc aag         3741
Ala Ser Thr Lys Gly Pro Ser Val Phe Pro Leu Ala Pro Ser Ser Lys
        350                 355                 360 agc acc agc gga gga acc gcc gcc ctg gga tgc ctg gtg aag gat tac         3789
Ser Thr Ser Gly Gly Thr Ala Ala Leu Gly Cys Leu Val Lys Asp Tyr
    365                 370                 375 ttc cca gag cca gtg acc gtg agc tgg aac agc gga gcc ctg acc agc         3837
Phe Pro Glu Pro Val Thr Val Ser Trp Asn Ser Gly Ala Leu Thr Ser
380                 385                 390                 395 gga gtg cac acc ttc cca gcc gtg ctg cag agc agc gga ctg tat agc         3885
Gly Val His Thr Phe Pro Ala Val Leu Gln Ser Ser Gly Leu Tyr Ser
            400                 405                 410 ctg agc agc gtg gtg acc gtg cca agc agc agc ctg gga acc cag acc         3933
Leu Ser Ser Val Val Thr Val Pro Ser Ser Ser Leu Gly Thr Gln Thr
        415                 420                 425 tac atc tgc aac gtg aac cac aag cca agc aac acc aag gtg gat aag         3981
Tyr Ile Cys Asn Val Asn His Lys Pro Ser Asn Thr Lys Val Asp Lys
    430                 435                 440 aag gtg gag cca aag agc tgc gat aag acc cac acg tgc cct cca tgt         4029
Lys Val Glu Pro Lys Ser Cys Asp Lys Thr His Thr Cys Pro Pro Cys
445                 450                 455 cca gcc ccc gaa ctg ctg ggc ggg cct agc gtg ttc ctg ttt ccc cct         4077
Pro Ala Pro Glu Leu Leu Gly Gly Pro Ser Val Phe Leu Phe Pro Pro
            460                 465                 470             475 aag cct aaa gat aca ctg atg att agt aga acc cca gag gtc aca tgc         4125
Lys Pro Lys Asp Thr Leu Met Ile Ser Arg Thr Pro Glu Val Thr Cys
        480                 485                 490 gtg gtc gtg gac gtg tcc cac gaa gag cct gac gtg aag ttc aac tgg         4173
Val Val Val Asp Val Ser His Glu Glu Pro Asp Val Lys Phe Asn Trp
    495                 500                 505 tac gtg gat ggc gtg gag gtg cac aat gct aag act aaa cca cgc gaa         4221
Tyr Val Asp Gly Val Glu Val His Asn Ala Lys Thr Lys Pro Arg Glu
510                 515                 520 gag cag tat aat agt aca tac cga gtc gtg tca gtc ctg aca gtg ctg         4269
Glu Gln Tyr Asn Ser Thr Tyr Arg Val Val Ser Val Leu Thr Val Leu
            525                 530                 535 cac cag gat tgg ctg aac ggc aag gag tat aag tgc aag gtg tct aac         4317
His Gln Asp Trp Leu Asn Gly Lys Glu Tyr Lys Cys Lys Val Ser Asn
540                 545                 550                 555 aag gcc ctg ccc gcc cct atc gag aaa aca att agc aag gcc aaa ggg         4365
Lys Ala Leu Pro Ala Pro Ile Glu Lys Thr Ile Ser Lys Ala Lys Gly
            560                 565                 570 cag cca cgg gaa ccc cag gtc tac act ctg cca ccc tca aga gat gaa         4413
Gln Pro Arg Glu Pro Gln Val Tyr Thr Leu Pro Pro Ser Arg Asp Glu
        575                 580                 585 ctg act aag aac cag gtc agc ctg acc tgt ctg gtg aaa ggc ttc tac         4461
Leu Thr Lys Asn Gln Val Ser Leu Thr Cys Leu Val Lys Gly Phe Tyr
    590                 595                 600 ccc agc gac atc gcc gtg gag tgg gaa agt aac ggc cag cct gag aat         4509
Pro Ser Asp Ile Ala Val Glu Trp Glu Ser Asn Gly Gln Pro Glu Asn
605                 610                 615 aac tac aag act acc cct cca gtg ctg gat agc gac ggg tcc ttc ttc         4557
Asn Tyr Lys Thr Thr Pro Pro Val Leu Asp Ser Asp Gly Ser Phe Phe
620                 625                 630                 635 ctg tat agc aag ctg aca gtg gac aaa tcc cgc tgg cag cag gga aac         4605
Leu Tyr Ser Lys Leu Thr Val Asp Lys Ser Arg Trp Gln Gln Gly Asn
            640                 645                 650
```

| | |
|---|---|
| gtc ttt tcc tgt tct gtg atg cat gag gcc ctg cac aat cat tac acc<br>Val Phe Ser Cys Ser Val Met His Glu Ala Leu His Asn His Tyr Thr<br>        655                 660                 665 | 4653 |
| cag aag agt ctg tca ctg agc ccc ggc aaa tgataaaagg aacccgcgct<br>Gln Lys Ser Leu Ser Leu Ser Pro Gly Lys<br>        670                 675 | 4703 |

| | |
|---|---|
| atgacggcaa taaaaagaca gaataaaaacc cacgggtgtt gggtcgtttg ttcataaacc | 4763 |
| cgggatcgat aaggatcttc ctagagcatg gctacgtaga taagtagcat ggcgggttaa | 4823 |
| tcattaacta caaggaaccc ctagtgatgg agttggccac tccctctctg cgcgctcgct | 4883 |
| cgctcactga ggccgggcga ccaaaggtcg cccgacgccc gggctttgcc cgggcggcct | 4943 |
| cagtgagcga gcgagcgcgc agccttaatt aacctaattc actggccgtc gttttacaac | 5003 |
| gtcgtgactg ggaaaaccct ggcgttaccc aacttaatcg ccttgcagca catccccctt | 5063 |
| tcgccagctg gcgtaatagc gaagaggccc gcaccgatcg cccttcccaa cagttgcgca | 5123 |
| gcctgaatgg cgaatgggac gcgccctgta gcggcgcatt aagcgcggcg ggtgtggtgg | 5183 |
| ttacgcgcag cgtgaccgct acacttgcca gcgccctagc gcccgctcct tcgcttttct | 5243 |
| tcccttcctt tctcgccacg ttcgccggct ttccccgtca gctctaaat cggggggctcc | 5303 |
| ctttagggtt ccgatttagt gctttacggc acctcgaccc caaaaaactt gattagggtg | 5363 |
| atggttcacg tagtgggcca tcgccctgat agacggtttt tcgccctttg acgttggagt | 5423 |
| ccacgttctt taatagtgga ctcttgttcc aaactggaac aacactcaac cctatctcgg | 5483 |
| tctattcttt tgatttataa gggattttgc cgatttcggc ctattggtta aaaaatgagc | 5543 |
| tgatttaaca aaaatttaac gcgaatttta caaaatatt aacgcttaca atttaggtgg | 5603 |
| cacttttcgg ggaaatgtgc gcggaacccc tatttgttta ttttttctaaa tacattcaaa | 5663 |
| tatgtatccg ctcatgagac aataaccctg ataaatgctt caataatatt gaaaaggaa | 5723 |
| gagtatgagt attcaacatt tccgtgtcgc ccttattccc ttttttgcgg cattttgcct | 5783 |
| tcctgttttt gctcacccag aaacgctggt gaaagtaaaa gatgctgaag atcagttggg | 5843 |
| tgcacgagtg ggttacatcg aactggatct caacagcggt aagatccttg agagttttcg | 5903 |
| ccccgaagaa cgttttccaa tgatgagcac ttttaaagtt ctgctatgtg gcgcggtatt | 5963 |
| atcccgtatt gacgccgggc aagagcaact cggtcgccgc atacactatt ctcagaatga | 6023 |
| cttggttgag tactcaccag tcacagaaaa gcatcttacg gatggcatga cagtaagaga | 6083 |
| attatgcagt gctgccataa ccatgagtga taacactgcg gccaacttac ttctgacaac | 6143 |
| gatcggagga ccgaaggagc taaccgcttt tttgcacaac atgggggatc atgtaactcg | 6203 |
| ccttgatcgt tgggaaccgg agctgaatga agccatacca aacgacgagc gtgacaccac | 6263 |
| gatgcctgta gcaatggcaa caacgttgcg caaactatta actggcgaac tacttactct | 6323 |
| agcttcccgg caacaattaa tagactggat ggaggcggat aaagttgcag gaccacttct | 6383 |
| gcgctcggcc cttccggctg gctggtttat tgctgataaa tctggagccg tgagcgtgg | 6443 |
| gtctcgcggt atcattgcag cactggggcc agatggtaag ccctcccgta tcgtagttat | 6503 |
| ctacacgacg gggagtcagg caactatgga tgaacgaaat agacagatcg ctgagatagg | 6563 |
| tgcctcactg attaagcatt ggtaactgtc agaccaagtt tactcatata cttttagat | 6623 |
| tgatttaaaa cttcattttt aatttaaaag gatctaggtg aagatccttt tgataatct | 6683 |
| catgaccaaa atcccttaac gtgagttttc gttccactga gcgtcagacc ccgtagaaaa | 6743 |
| gatcaaagga tcttcttgag atcctttttt tctgcgcgta atctgctgct tgcaaacaaa | 6803 |
| aaaaccaccg ctaccagcgg tggtttgttt gccggatcaa gagctaccaa ctctttttcc | 6863 |

```
gaaggtaact ggcttcagca gagcgcagat accaaatact gttcttctag tgtagccgta   6923
gttaggccac cacttcaaga actctgtagc accgcctaca tacctcgctc tgctaatcct   6983
gttaccagtg gctgctgcca gtggcgataa gtcgtgtctt accgggttgg actcaagacg   7043
atagttaccg gataaggcgc agcggtcggg ctgaacgggg ggttcgtgca cacagcccag   7103
cttggagcga acgacctaca ccgaactgag atacctacag cgtgagctat gagaaagcgc   7163
cacgcttccc gaagggagaa aggcggacag gtatccggta agcggcaggg tcggaacagg   7223
agagcgcacg agggagcttc caggggggaaa cgcctggtat ctttatagtc ctgtcgggtt   7283
tcgccacctc tgacttgagc gtcgattttt gtgatgctcg tcagggggc ggagcctatg   7343 gaaaaacgcc agcaacgcgg ccttttttacg gttcctggcc ttttgctggc cttttgctca   7403
catgttcttt cctgcgttat cccctgattc tgtggataac cgtattaccg cctttgagtg   7463
agctgatacc gctcgccgca gccgaacgac cgagcgcagc gagtcagtga gcgaggaagc   7523
ggaagagcgc ccaatacgca aaccgcctct ccccgcgcgt tggccgattc attaatgcag   7583
ctggcacgac aggtttcccg actggaaagc gggcagtgag cgcaacgcaa ttaatgtgag   7643
ttagctcact cattaggcac cccaggcttt acactttatg cttccggctc gtatgttgtg   7703
tggaattgtg agcggataac aatttcacac aggaaacagc tatgaccatg attacgccag   7763
atttaattaa                                                         7773

<210> SEQ ID NO 9
<211> LENGTH: 111
<212> TYPE: PRT
<213> ORGANISM: Artificial sequence
<220> FEATURE:
<223> OTHER INFORMATION: Synthetic Construct

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 10
<211> LENGTH: 107
<212> TYPE: PRT
<213> ORGANISM: Artificial sequence
<220> FEATURE:
<223> OTHER INFORMATION: Synthetic Construct

<400> SEQUENCE: 10

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105

<210> SEQ ID NO 11
<211> LENGTH: 129
<212> TYPE: PRT
<213> ORGANISM: Artificial sequence
<220> FEATURE:
<223> OTHER INFORMATION: Synthetic Construct

<400> SEQUENCE: 11

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Tyr
                 20                  25                  30

Ala Met His Trp Val Arg Gln Ala Pro Gly Lys Gly Leu Glu Trp Val
             35                  40                  45

Ala Val Ile Ser Tyr Asp Ala Asn Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Ser Leu Leu Tyr Phe Glu Trp Leu Ser
                100                 105                 110

Gln Gly Tyr Phe Asp Tyr Trp Gly Gln Gly Thr Leu Val Thr Val Ser
             115                 120                 125

Ser

<210> SEQ ID NO 12
<211> LENGTH: 107
<212> TYPE: PRT
<213> ORGANISM: Artificial sequence
<220> FEATURE:
<223> OTHER INFORMATION: Synthetic Construct

<400> SEQUENCE: 12

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 13
<211> LENGTH: 223
<212> TYPE: PRT
<213> ORGANISM: Artificial sequence
<220> FEATURE:
<223> OTHER INFORMATION: Synthetic Construct

<400> SEQUENCE: 13

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 14
<211> LENGTH: 7728
<212> TYPE: DNA
<213> ORGANISM: Artificial sequence
<220> FEATURE:
<223> OTHER INFORMATION: Plasmid encoding synthetic FI6 and 1A6
      monoconals
<220> FEATURE:
<221> NAME/KEY: polyA_signal
<222> LOCATION: (191)..(239)
<223> OTHER INFORMATION: synthetic\polyA
<220> FEATURE:
<221> NAME/KEY: misc_feature
<222> LOCATION: (246)..(914)
<223> OTHER INFORMATION: complement - CH'2-3
<220> FEATURE:
<221> NAME/KEY: misc_feature
<222> LOCATION: (915)..(1235)
<223> OTHER INFORMATION: complement - CH'1
```

```
<220> FEATURE:
<221> NAME/KEY: misc_feature
<222> LOCATION: (1236)..(1598)
<223> OTHER INFORMATION: complement - 1A6\VH
<220> FEATURE:
<221> NAME/KEY: misc_feature
<222> LOCATION: (1599)..(1655)
<223> OTHER INFORMATION: complement - leader
<220> FEATURE:
<221> NAME/KEY: misc_feature
<222> LOCATION: (1665)..(1733)
<223> OTHER INFORMATION: complement - CMV\mp2
<220> FEATURE:
<221> NAME/KEY: misc_feature
<222> LOCATION: (1732)..(2202)
<223> OTHER INFORMATION: Enhancer
<220> FEATURE:
<221> NAME/KEY: misc_feature
<222> LOCATION: (2203)..(2328)
<223> OTHER INFORMATION: CMV\mp1
<220> FEATURE:
<221> NAME/KEY: misc_feature
<222> LOCATION: (2388)..(2444)
<223> OTHER INFORMATION: leader
<220> FEATURE:
<221> NAME/KEY: misc_feature
<222> LOCATION: (2445)..(2789)
<223> OTHER INFORMATION: KGL
<220> FEATURE:
<221> NAME/KEY: CDS
<222> LOCATION: (2784)..(3104)
<223> OTHER INFORMATION: CL
<220> FEATURE:
<221> NAME/KEY: misc_feature
<222> LOCATION: (3189)..(3248)
<223> OTHER INFORMATION: leader
<220> FEATURE:
<221> NAME/KEY: CDS
<222> LOCATION: (3249)..(3635)
<223> OTHER INFORMATION: FI6\VH
<220> FEATURE:
<221> NAME/KEY: CDS
<222> LOCATION: (3636)..(3956)
<223> OTHER INFORMATION: CH1
<220> FEATURE:
<221> NAME/KEY: CDS
<222> LOCATION: (3957)..(4625)
<223> OTHER INFORMATION: CH2-3
<220> FEATURE:
<221> NAME/KEY: polyA_signal
<222> LOCATION: (4632)..(4709)
<223> OTHER INFORMATION: TKpAshort

<400> SEQUENCE: 14
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctacgta gccatgctct     180
aggaagatct cacacaaaaa accaacacac agatgtaatg aaaataaaga tattttattt     240
tatcacttcc cggggctcag gctcaggggac ttctgggtgt agtggttgtg cagggcctcg     300
tgcatcacgc tgcagctgaa cacgttgccc tgctgccacc ggctcttgtc cacggtcagc     360
ttgctataca ggaagaatga gccgtcgctg tccagcacag gggggggtggt cttgtagttg     420 ttctcgggct ggccgttgct ctcccattcc acggcgatct cgctgggta gaagcccttg     480 accaggcagg tcaggggacac ctggttcttg gtcatctctt cccggctggg gggcagtgtg     540
tagacctgag gctcgcgggg ctggcccttg gccttgctga tggttttctc gatgggggca     600
ggcagggcct tgttggacac cttgcacttg tactctttgc cgttcagcca gtcctggtgc     660
agcacggtca gcacggacac caccccggtag gtgctgttgt actgttcctc tctgggcttg     720
```

```
gtcttggcgt tgtgcacttc cacgccgtcc acgtaccaat tgaacttcac ttcagggtcc      780
tcgtgggaca cgtccaccac cacgcaggtc acttcggggg tccggctgat catcagggtg      840
tccttgggct ttgggggggaa caggaacacg ctggggcctc ccagcagttc aggggcaggg     900
caggggggac acgtgtgggt cttgtcgcag ctcttaggtt ccacccgctt gtccaccttg     960
gtgttgctgg gcttgtggtt cacgttgcag atgtaggtct gggtgcccag gctgctgctg    1020
ggcacggtga ccacgctgct caggctatac aggccgctgc tctgcagcac ggctggaaag    1080
gtgtgcacgc cgctggtcag ggcgccagag ttccaggaca cggtcacggg ctcggggaag    1140
tagtccttga ccaggcagcc cagggcggct gttccgccag aggtgctctt gctgctaggg    1200
gccagaggga acacgcttgg tcccttggtg ctggcgctcg acggtcac cagggttccc      1260 tgtccccagt aatccattcc tccgctggcg attccgctcc gatccttggc gcagtagtac    1320
acggcggtat cctcggcccg caggctgttc atctgcaggt acagggtgtt cttgctgttg    1380
gcccggctga tggtgaaccg tcccttcacg ctatcggcgt agtacttgtt gtttccatcg    1440
tagctgatca cggccaccca ctccagtccc tttcctgggg cctgccgcac ccagtgcatt    1500
ccgtaatcgc tgaaggtgaa tccgctggcg gcgcagctca gccgcaggct ccgtcctggc    1560
tgcaccactc ctcctccgct ctcctgcagc tgcacctgtg aattcgtcac cagggccagg    1620
ctcagggcga tcagcagcag cagctgcatg cgcatggtgg cggcgcgatc tgacggttca    1680
ctaaacgagc tctgcttata taggcctccc accgtacacg ccacctcgac atacctagtt    1740
attaatagta atcaattacg gggtcattag ttcatagccc atatatggag ttccgcgtta    1800
cataacttac ggtaaatggc ccgcctggct gaccgcccaa cgaccccgc ccattgacgt     1860 caataatgac gtatgttccc atagtaacgc caatagggac tttccattga cgtcaatggg    1920
tggagtattt acggtaaact gcccacttgg cagtacatca agtgtatcat atgccaagta    1980
cgccccctat tgacgtcaat gacggtaaat ggcccgcctg gcattatgcc cagtacatga    2040
ccttatggga ctttcctact tggcagtaca tctacgtatt agtcatcgct attaccatgg    2100
tgatgcggtt ttggcagtac atcaatgggc gtggatagcg gtttgactca cggggatttc    2160
caagtctcca ccccattgac gtcaatggga gtttgttttg gcaccaaaat caacgggact    2220
ttccaaaatg tcgtaacaac tccgccccat tgacgcaaat gggcggtagg cgtgtacggt    2280
gggaggtcta tataagcaga gctggtttag tgaaccgtca gatccgctgg cactttgca    2340 ctggaactta caacacccga gcaaggacgc gactctgccg ccccaccatg cgcatgcagc    2400
tgctgctgct gatcgccctg agcctggccc tggtgaccaa cagcgatatc gtcatgaccc    2460
agagcccaga tagcctggcc gtgagcctgg agagcgggc caccatcaac tgcaagagca    2520
gccagagcgt gctgtacagc agcaacaaca gaaactacct ggcctggtac cagcagaagc    2580
caggacagcc accaaagctg ctgatctact gggccagcac ccgggagagc ggagtgccag    2640
atcggttcag cggaagcgga agcggaaccg atttcacccT gaccatcagc agcctgcagg    2700
ccgaggatgt ggccgtgtac tactgccagc agtactacag cacccactg accttcggac    2760
```

| aggga accaa ggtggagatc aag cgt acg gtg gcc gcc cca agc gtg ttc atc | 2813 |
|---|---|
| Arg Thr Val Ala Ala Pro Ser Val Phe Ile | |
| 1 5 10 | |

| ttc cca cca agc gat gag cag ctg aag agc gga acc gcc agc gtg gtg | 2861 |
|---|---|
| Phe Pro Pro Ser Asp Glu Gln Leu Lys Ser Gly Thr Ala Ser Val Val | |
| 15 20 25 | |

| tgc ctg ctg aac aac ttc tac cca cgg gag gcc aag gtg cag tgg aag | 2909 |
|---|---|
| Cys Leu Leu Asn Asn Phe Tyr Pro Arg Glu Ala Lys Val Gln Trp Lys | |
| 30 35 40 | |

```
                                          -continued gtg gat aac gcc ctg cag agc gga aac agc cag gag agc gtg acc gag    2957
Val Asp Asn Ala Leu Gln Ser Gly Asn Ser Gln Glu Ser Val Thr Glu
         45                  50                  55 cag gat agc aag gat agc acc tac agc ctg agc agc acc ctg acc ctg    3005
Gln Asp Ser Lys Asp Ser Thr Tyr Ser Leu Ser Ser Thr Leu Thr Leu
 60                  65                  70 agc aag gcc gat tac gag aag cac aag gtg tac gcc tgc gag gtg acc    3053
Ser Lys Ala Asp Tyr Glu Lys His Lys Val Tyr Ala Cys Glu Val Thr
 75                  80                  85                  90 cac cag gga ctg agc agc cca gtg acc aag agc ttc aac cgc gga gag    3101
His Gln Gly Leu Ser Ser Pro Val Thr Lys Ser Phe Asn Arg Gly Glu
                 95                 100                 105 tgc cggaagcggc gggcccagt gaagcagacc ctgaacttcg atctgctgaa          3154
Cys gctggccgga gatgtggaga gcaacccagg accaatgtac agaatgcagc tgctgagctg  3214
catcgccctg agcctggccc tggtgaccaa cagc cag gtg caa cta gtg gag agc  3269
                                 Gln Val Gln Leu Val Glu Ser
                                                 110 gga gga gga gtg gtg cag cca gga cgg agc ctg cgg ctg agc tgc gcc    3317
Gly Gly Gly Val Val Gln Pro Gly Arg Ser Leu Arg Leu Ser Cys Ala
115                 120                 125                 130 gcc agc gga ttc acc ttc agc acc tac gcc atg cac tgg gtg cgg cag    3365
Ala Ser Gly Phe Thr Phe Ser Thr Tyr Ala Met His Trp Val Arg Gln
                135                 140                 145 gcc cca gga aag gga ctg gag tgg gtg gcc gtg atc agc tac gat gcc    3413
Ala Pro Gly Lys Gly Leu Glu Trp Val Ala Val Ile Ser Tyr Asp Ala
            150                 155                 160 aac tac aag tac tac gcc gat agc gtg aag gga cgg ttc acc atc agc    3461
Asn Tyr Lys Tyr Tyr Ala Asp Ser Val Lys Gly Arg Phe Thr Ile Ser
        165                 170                 175 cgg gat aac agc aag aac acc ctg tac ctg cag atg aac agc ctg cgg    3509
Arg Asp Asn Ser Lys Asn Thr Leu Tyr Leu Gln Met Asn Ser Leu Arg
180                 185                 190 gcc gag gat acc gcc gtg tac tac tgc gcc aag gat agc cag ctg cgg    3557
Ala Glu Asp Thr Ala Val Tyr Tyr Cys Ala Lys Asp Ser Gln Leu Arg
195                 200                 205                 210 agc ctg ctg tac ttc gag tgg ctg agc cag gga tac ttc gat tac tgg    3605
Ser Leu Leu Tyr Phe Glu Trp Leu Ser Gln Gly Tyr Phe Asp Tyr Trp
                215                 220                 225 gga cag gga acc ctg gtg acc gtg agc agc gct agc acc aag gga cca    3653
Gly Gln Gly Thr Leu Val Thr Val Ser Ser Ala Ser Thr Lys Gly Pro
            230                 235                 240 agc gtg ttc cca ctg gcc cca agc agc aag agc acc agc gga gga acc    3701
Ser Val Phe Pro Leu Ala Pro Ser Ser Lys Ser Thr Ser Gly Gly Thr
        245                 250                 255 gcc gcc ctg gga tgc ctg gtg aag gat tac ttc cca gag cca gtg acc    3749
Ala Ala Leu Gly Cys Leu Val Lys Asp Tyr Phe Pro Glu Pro Val Thr
260                 265                 270 gtg agc tgg aac agc gga gcc ctg acc agc gga gtg cac acc ttc cca    3797
Val Ser Trp Asn Ser Gly Ala Leu Thr Ser Gly Val His Thr Phe Pro
275                 280                 285                 290 gcc gtg ctg cag agc agc gga ctg tat agc ctg agc agc gtg gtg acc    3845
Ala Val Leu Gln Ser Ser Gly Leu Tyr Ser Leu Ser Ser Val Val Thr
                295                 300                 305 gtg cca agc agc agc ctg gga acc cag acc tac atc tgc aac gtg aac    3893
Val Pro Ser Ser Ser Leu Gly Thr Gln Thr Tyr Ile Cys Asn Val Asn
            310                 315                 320
```

-continued

| | |
|---|---|
| cac aag cca agc aac acc aag gtg gat aag aag gtg gag cca aag agc<br>His Lys Pro Ser Asn Thr Lys Val Asp Lys Lys Val Glu Pro Lys Ser<br>325              330                 335 | 3941 |
| tgc gat aag acc cac acg tgc cct cct tgt cca gcc ccc gaa ctg ctg<br>Cys Asp Lys Thr His Thr Cys Pro Pro Cys Pro Ala Pro Glu Leu Leu<br>340              345                 350 | 3989 |
| ggc ggg cct agc gtg ttc ctg ttt ccc cct aag cct aaa gat aca ctg<br>Gly Gly Pro Ser Val Phe Leu Phe Pro Pro Lys Pro Lys Asp Thr Leu<br>355              360                 365                 370 | 4037 |
| atg att agt aga acc cca gag gtc aca tgc gtg gtg gtg gac gtg tcc<br>Met Ile Ser Arg Thr Pro Glu Val Thr Cys Val Val Val Asp Val Ser<br>375              380                 385 | 4085 |
| cac gaa gag cct gac gtg aag ttc aac tgg tac gtg gat ggc gtg gag<br>His Glu Glu Pro Asp Val Lys Phe Asn Trp Tyr Val Asp Gly Val Glu<br>390              395                 400 | 4133 |
| gtg cac aat gct aag act aaa cca cgc gaa gag cag tat aat agt aca<br>Val His Asn Ala Lys Thr Lys Pro Arg Glu Glu Gln Tyr Asn Ser Thr<br>405              410                 415 | 4181 |
| tac cga gtc gtg tca gtc ctg aca gtg ctg cac cag gat tgg ctg aac<br>Tyr Arg Val Val Ser Val Leu Thr Val Leu His Gln Asp Trp Leu Asn<br>420              425                 430 | 4229 |
| ggc aag gag tat aag tgc aag gtg tct aac aag gcc ctg ccc gcc cct<br>Gly Lys Glu Tyr Lys Cys Lys Val Ser Asn Lys Ala Leu Pro Ala Pro<br>435              440                 445                 450 | 4277 |
| atc gag aaa aca att agc aag gcc aaa ggg cag cca cgg gaa ccc cag<br>Ile Glu Lys Thr Ile Ser Lys Ala Lys Gly Gln Pro Arg Glu Pro Gln<br>455              460                 465 | 4325 |
| gtc tac act ctg cca ccc tca aga gat gaa ctg act aag aac cag gtc<br>Val Tyr Thr Leu Pro Pro Ser Arg Asp Glu Leu Thr Lys Asn Gln Val<br>470              475                 480 | 4373 |
| agc ctg acc tgt ctg gtg aaa ggc ttc tac ccc agc gac atc gcc gtg<br>Ser Leu Thr Cys Leu Val Lys Gly Phe Tyr Pro Ser Asp Ile Ala Val<br>485              490                 495 | 4421 |
| gag tgg gaa agt aac ggc cag cct gag aat aac tac aag act acc cct<br>Glu Trp Glu Ser Asn Gly Gln Pro Glu Asn Asn Tyr Lys Thr Thr Pro<br>500              505                 510 | 4469 |
| cca gtg ctg gat agc gac ggg tcc ttc ttc ctg tat agc aag ctg aca<br>Pro Val Leu Asp Ser Asp Gly Ser Phe Phe Leu Tyr Ser Lys Leu Thr<br>515              520                 525                 530 | 4517 |
| gtg gac aaa tcc cgc tgg cag cag gga aac gtc ttt tcc tgt tct gtg<br>Val Asp Lys Ser Arg Trp Gln Gln Gly Asn Val Phe Ser Cys Ser Val<br>535              540                 545 | 4565 |
| atg cat gag gcc ctg cac aat cat tac acc cag aag agt ctg tca ctg<br>Met His Glu Ala Leu His Asn His Tyr Thr Gln Lys Ser Leu Ser Leu<br>550              555                 560 | 4613 |
| agc ccc ggc aaa tgataaaagg aacccgcgct atgacggcaa taaaaagaca<br>Ser Pro Gly Lys<br>565 | 4665 |
| gaataaaacc cacgggtgtt gggtcgtttg ttcataaacc cgggatcgat aaggatcttc | 4725 |
| ctagagcatg gctacgtaga taagtagcat ggcgggttaa tcattaacta caaggaaccc | 4785 |
| ctagtgatgg agttggccac tccctctctg cgcgctcgct cgctcactga ggccgggcga | 4845 |
| ccaaaggtcg cccgacgccc gggctttgcc cgggcggcct cagtgagcga gcgagcgcgc | 4905 |
| agccttaatt aacctaattc actggccgtc gttttacaac gtcgtgactg ggaaaaccct | 4965 |
| ggcgttaccc aacttaatcg ccttgcagca catccccctt tcgccagctg gcgtaatagc | 5025 |
| gaagaggccc gcaccgatcg cccttcccaa cagttgcgca gcctgaatgg cgaatgggac | 5085 |
| gcgccctgta gcggcgcatt aagcgcggcg ggtgtggtgg ttacgcgcag cgtgaccgct | 5145 |

```
acacttgcca gcgccctagc gcccgctcct ttcgctttct tcccttcctt tctcgccacg    5205
ttcgccggct ttccccgtca agctctaaat cggggggctcc ctttagggtt ccgatttagt    5265
gctttacggc acctcgaccc caaaaaactt gattaggggtg atggttcacg tagtgggcca    5325
tcgccctgat agacggtttt tcgcccttttg acgttggagt ccacgttctt taatagtgga    5385
ctcttgttcc aaactggaac aacactcaac cctatctcgg tctattcttt tgatttataa    5445
gggattttgc cgatttcggc ctattggtta aaaatgagc tgatttaaca aaaatttaac    5505
gcgaatttta acaaaatatt aacgcttaca atttaggtgg cacttttcgg ggaaatgtgc    5565
gcggaacccc tatttgttta ttttttctaaa tacattcaaa tatgtatccg ctcatgagac    5625
aataaccctg ataaatgctt caataatatt gaaaaaggaa gagtatgagt attcaacatt    5685
tccgtgtcgc ccttattccc ttttttgcgg cattttgcct tcctgttttt gctcacccag    5745
aaacgctggt gaaagtaaaa gatgctgaag atcagttggg tgcacgagtg ggttacatcg    5805
aactggatct caacagcggt aagatccttg agagttttcg ccccgaagaa cgttttccaa    5865
tgatgagcac ttttaaagtt ctgctatgtg gcgcggtatt atcccgtatt gacgccgggc    5925
aagagcaact cggtcgccgc atacactatt ctcagaatga cttggttgag tactcaccag    5985
tcacagaaaa gcatcttacg gatggcatga cagtaagaga attatgcagt gctgccataa    6045
ccatgagtga taacactgcg gccaacttac ttctgacaac gatcggagga ccgaaggagc    6105
taaccgcttt tttgcacaac atgggggatc atgtaactcg ccttgatcgt tgggaaccgg    6165
agctgaatga agccatacca aacgacgagc gtgacaccac gatgcctgta gcaatggcaa    6225
caacgttgcg caaactatta actggcgaac tacttactct agcttcccgg caacaattaa    6285
tagactggat ggaggcggat aaagttgcag gaccacttct gcgctcggcc cttccggctg    6345
gctggtttat tgctgataaa tctggagccg gtgagcgtgg gtctcgcggt atcattgcag    6405
cactggggcc agatggtaag ccctcccgta tcgtagttat ctacacgacg gggagtcagg    6465
caactatgga tgaacgaaat agacagatcg ctgagatagg tgcctcactg attaagcatt    6525
ggtaactgtc agaccaagtt tactcatata ctttagat tgatttaaaa cttcattttt    6585
aatttaaaag gatctaggtg aagatccttt ttgataatct catgaccaaa atcccttaac    6645
gtgagttttc gttccactga gcgtcagacc ccgtagaaaa gatcaaagga tcttcttgag    6705 atccttttttt tctgcgcgta atctgctgct tgcaaacaaa aaaaccaccg ctaccagcgg    6765
tggtttgttt gccggatcaa gagctaccaa ctctttttcc gaaggtaact ggcttcagca    6825
gagcgcagat accaaatact gttcttctag tgtagccgta gttaggccac cacttcaaga    6885
actctgtagc accgcctaca tacctcgctc tgctaatcct gttaccagtg gctgctgcca    6945
gtggcgataa gtcgtgtctt accgggttgg actcaagacg atagttaccg gataaggcgc    7005
agcggtcggg ctgaacgggg ggttcgtgca cacagcccag cttggagcga acgacctaca    7065
ccgaactgag atacctacag cgtgagctat gagaaagcgc cacgcttccc gaagggagaa    7125
aggcggacag gtatccggta agcggcaggg tcggaacagg agagcgcacg agggagcttc    7185
cagggggaaa cgcctggtat ctttatagtc ctgtcgggtt tcgccacctc tgacttgagc    7245
gtcgattttt gtgatgctcg tcagggggggc ggagcctatg gaaaaacgcc agcaacgcgg    7305
cctttttacg gttcctggcc ttttgctggc cttttgctca catgttcttt cctgcgttat    7365
cccctgattc tgtggataac cgtattaccg ccttttgagtg agctgatacc gctcgccgca    7425
gccgaacgac cgagcgcagc gagtcagtga gcgaggaagc ggaagagcgc ccaatacgca    7485
aaccgcctct ccccgcgcgt tggccgattc attaatgcag ctggcacgac aggtttcccg    7545
```

```
actggaaagc gggcagtgag cgcaacgcaa ttaatgtgag ttagctcact cattaggcac    7605
cccaggcttt acactttatg cttccggctc gtatgttgtg tggaattgtg agcggataac    7665
aatttcacac aggaaacagc tatgaccatg attacgccag atttaattaa ggccttaatt    7725
agg                                                                 7728
```

<210> SEQ ID NO 15
<211> LENGTH: 107
<212> TYPE: PRT
<213> ORGANISM: Artificial sequence
<220> FEATURE:
<223> OTHER INFORMATION: Synthetic Construct

<400> SEQUENCE: 15

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 16
<211> LENGTH: 129
<212> TYPE: PRT
<213> ORGANISM: Artificial sequence
<220> FEATURE:
<223> OTHER INFORMATION: Synthetic Construct

<400> SEQUENCE: 16

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser
```

```
<210> SEQ ID NO 17
<211> LENGTH: 107
<212> TYPE: PRT
<213> ORGANISM: Artificial sequence
<220> FEATURE:
<223> OTHER INFORMATION: Synthetic Construct

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 18
<211> LENGTH: 223
<212> TYPE: PRT
<213> ORGANISM: Artificial sequence
<220> FEATURE:
<223> OTHER INFORMATION: Synthetic Construct

<400> SEQUENCE: 18

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190
```

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 19
<211> LENGTH: 7746
<212> TYPE: DNA
<213> ORGANISM: Artificial sequence
<220> FEATURE:
<223> OTHER INFORMATION: Plasmid carrying FI6 and CR8033 monoclonals
<220> FEATURE:
<221> NAME/KEY: polyA_signal
<222> LOCATION: (173)..(221)
<223> OTHER INFORMATION: synthetic\polyA
<220> FEATURE:
<221> NAME/KEY: misc_feature
<222> LOCATION: (228)..(896)
<223> OTHER INFORMATION: complement - CH'2-3
<220> FEATURE:
<221> NAME/KEY: misc_feature
<222> LOCATION: (897)..(1217)
<223> OTHER INFORMATION: complement - CH'1
<220> FEATURE:
<221> NAME/KEY: misc_feature
<222> LOCATION: (1218)..(1604)
<223> OTHER INFORMATION: complement - CR8033\VH
<220> FEATURE:
<221> NAME/KEY: misc_feature
<222> LOCATION: (1605)..(1655)
<223> OTHER INFORMATION: complement - leader
<220> FEATURE:
<221> NAME/KEY: misc_feature
<222> LOCATION: (1665)..(1733)
<223> OTHER INFORMATION: complement - CMV\mp2
<220> FEATURE:
<221> NAME/KEY: misc_feature
<222> LOCATION: (1734)..(2202)
<223> OTHER INFORMATION: Enhancer
<220> FEATURE:
<221> NAME/KEY: misc_feature
<222> LOCATION: (2203)..(2328)
<223> OTHER INFORMATION: CMV\mp1
<220> FEATURE:
<221> NAME/KEY: misc_feature
<222> LOCATION: (2445)..(2789)
<223> OTHER INFORMATION: KGL
<220> FEATURE:
<221> NAME/KEY: CDS
<222> LOCATION: (2784)..(3104)
<223> OTHER INFORMATION: CL
<220> FEATURE:
<221> NAME/KEY: misc_feature
<222> LOCATION: (3189)..(3248)
<223> OTHER INFORMATION: leader
<220> FEATURE:
<221> NAME/KEY: CDS
<222> LOCATION: (3249)..(3635)
<223> OTHER INFORMATION: FI6\VH
<220> FEATURE:
<221> NAME/KEY: CDS
<222> LOCATION: (3636)..(3956)
<223> OTHER INFORMATION: CH1
<220> FEATURE:
<221> NAME/KEY: CDS
<222> LOCATION: (3957)..(4625)
<223> OTHER INFORMATION: CH2-3
<220> FEATURE:
<221> NAME/KEY: misc_feature
<222> LOCATION: (3968)..(3968)
<223> OTHER INFORMATION: A -> T
<220> FEATURE:
<221> NAME/KEY: polyA_signal
<222> LOCATION: (4632)..(4709)
<223> OTHER INFORMATION: TKpAshort

<400> SEQUENCE: 19

```
actgaggccg cccgggcaaa gcccgggcgt cgggcgacct ttggtcgccc ggcctcagtg    60
agcgagcgag cgcgcagaga gggagtggcc aactccatca ctaggggttc cttgtagtta   120
atgattaacc cgccatgcta cttatctacg tagccatgct ctaggaagat ctcacacaaa   180
aaaccaacac acagatgtaa tgaaaataaa gatattttat tttatcactt cccggggctc   240
aggctcaggg acttctgggt gtagtggttg tgcagggcct cgtgcatcac gctgcagctg   300
aacacgttgc cctgctgcca ccggctcttg tccacggtca gcttgctata caggaagaat   360
gagccgtcgc tgtccagcac aggggggtg gtcttgtagt tgttctcggg ctggccgttg   420
ctctcccatt ccacggcgat ctcgctgggg tagaagccct tgaccaggca ggtcagggac   480
acctggttct tggtcatctc ttcccggctg ggggcagtg tgtagacctg aggctcgcgg   540
ggctggccct tggccttgct gatggttttc tcgatggggg caggcagggc cttgttggac   600
accttgcact tgtactcttt gccgttcagc cagtcctggt gcagcacggt cagcacggac   660
accacccggt aggtgctgtt gtactgttcc tctctgggct tggtcttggc gttgtgcact   720
tccacgccgt ccacgtacca attgaacttc acttcagggt cctcgtggga cacgtccacc   780
accacgcagg tcacttcggg ggtccggctg atcatcaggg tgtccttggg cttgggggg    840
aacaggaaca cgctggggcc tcccagcagt tcagggcag gcaggggg acacgtgtgg      900
gtcttgtcgc agctcttagg ttccacccgc ttgtccacct tggtgttgct gggcttgtgg   960
ttcacgttgc agatgtaggt ctgggtgccc aggctgctgc tgggcacggt gaccacgctg  1020
ctcaggctat acaggccgct gctctgcagc acggctggaa aggtgtgcac gccgctggtc  1080
agggcgccag agttccagga cacggtcacg ggctcgggga agtagtcctt gaccaggcag  1140
cccagggcgg ctgttccgcc agaggtgctc ttgctgctag gggccagagg gaacacgctt  1200
ggtcccttgg tgctggcgct cgagacggtc accatggttc cctgtcccca gatatcgaag  1260
gttcctccct ccaggatatc catggcgctg ctctccagcc gatccttggc gcagtagtac  1320
agggcggtat cctcggcccg caggctgttc atctgcaggt acaggctgtt ctttccgtta  1380
tcccggctga tggtgaaccg tccctgcacg ctatcggcgt atcccatgaa gtttcccttc  1440
cagttgattc cggccaccca ctccagtccc tttcctgggg cctgccgcac ccagtgcatg  1500
gtgtactcat cgaagctgaa tccgctgcg gcgcagctca gccgcaggct ccgtcctggc  1560
tgcaccagtc ctcctccggt ctccaccagc tgcacctctg aattcgtcac cagggccagg  1620
ctcagggcga tcagcagcag cagctgcatg cgcatggtgg cggcgcgatc tgacggttca  1680
ctaaacgagc tctgcttata taggcctccc accgtacacg ccacctcgac atacctagtt  1740
attaatagta atcaattacg gggtcattag ttcatagccc atatatggag ttccgcgtta  1800
cataacttac ggtaaatggc ccgcctggct gaccgcccaa cgaccccgc ccattgacgt   1860
caataatgac gtatgttccc atagtaacgc caatagggac tttccattga cgtcaatggg  1920
tggagtattt acggtaaact gcccacttgg cagtacatca agtgtatcat atgccaagta  1980
cgccccctat tgacgtcaat gacggtaaat ggcccgcctg gcattatgcc cagtacatga  2040
ccttatggga ctttcctact tggcagtaca tctacgtatt agtcatcgct attaccatgg  2100
tgatgcggtt ttggcagtac atcaatgggc gtggatagcg gtttgactca cggggatttc  2160
caagtctcca ccccattgac gtcaatggga gtttgttttg gcaccaaaat caacgggact  2220
ttccaaaatg tcgtaacaac tccgccccat tgacgcaaat gggcggtagg cgtgtacggt  2280
gggaggtcta tataagcaga gctggtttag tgaaccgtca gatccgctgg gcactttgca  2340
```

-continued

```
ctggaactta caacacccga gcaaggacgc gactctgccg ccccaccatg cgcatgcagc    2400
tgctgctgct gatcgccctg agcctggccc tggtgaccaa cagcgatatc gtcatgaccc    2460
agagcccaga tagcctggcc gtgagcctgg agagcgggc caccatcaac tgcaagagca    2520
gccagagcgt gctgtacagc agcaacaaca gaaactacct ggcctggtac agcagaagc    2580 caggacagcc accaaagctg ctgatctact gggccagcac ccgggagagc ggagtgccag    2640
atcggttcag cggaagcgga agcggaaccg atttcaccct gaccatcagc agcctgcagg    2700
ccgaggatgt ggccgtgtac tactgccagc agtactacag caccccactg accttcggac    2760
agggaaccaa ggtggagatc aag cgt acg gtg gcc gcc cca agc gtg ttc atc    2813
                        Arg Thr Val Ala Ala Pro Ser Val Phe Ile
                         1               5                  10 ttc cca cca agc gat gag cag ctg aag agc gga acc gcc agc gtg gtg    2861
Phe Pro Pro Ser Asp Glu Gln Leu Lys Ser Gly Thr Ala Ser Val Val
             15                  20                  25 tgc ctg ctg aac aac ttc tac cca cgg gag gcc aag gtg cag tgg aag    2909
Cys Leu Leu Asn Asn Phe Tyr Pro Arg Glu Ala Lys Val Gln Trp Lys
         30                  35                  40 gtg gat aac gcc ctg cag agc gga aac agc cag gag agc gtg acc gag    2957
Val Asp Asn Ala Leu Gln Ser Gly Asn Ser Gln Glu Ser Val Thr Glu
     45                  50                  55 cag gat agc aag gat agc acc tac agc ctg agc agc acc ctg acc ctg    3005
Gln Asp Ser Lys Asp Ser Thr Tyr Ser Leu Ser Ser Thr Leu Thr Leu
 60                  65                  70 agc aag gcc gat tac gag aag cac aag gtg tac gcc tgc gag gtg acc    3053
Ser Lys Ala Asp Tyr Glu Lys His Lys Val Tyr Ala Cys Glu Val Thr
 75                  80                  85                  90 cac cag gga ctg agc agc cca gtg acc aag agc ttc aac cgc gga gag    3101
His Gln Gly Leu Ser Ser Pro Val Thr Lys Ser Phe Asn Arg Gly Glu
                 95                 100                 105 tgc cggaagcggc gggccccagt gaagcagacc ctgaacttcg atctgctgaa         3154
Cys gctggccgga gatgtggaga gcaacccagg accaatgtac agaatgcagc tgctgagctg    3214
catcgccctg agcctggccc tggtgaccaa cagc cag gtg caa cta gtg gag agc    3269
                                     Gln Val Gln Leu Val Glu Ser
                                                     110 gga gga gga gtg gtg cag cca gga cgg agc ctg cgg ctg agc tgc gcc    3317
Gly Gly Gly Val Val Gln Pro Gly Arg Ser Leu Arg Leu Ser Cys Ala
115                 120                 125                 130 gcc agc gga ttc acc ttc agc acc tac gcc atg cac tgg gtg cgg cag    3365
Ala Ser Gly Phe Thr Phe Ser Thr Tyr Ala Met His Trp Val Arg Gln
                135                 140                 145 gcc cca gga aag gga ctg gag tgg gtg gcc gtg atc agc tac gat gcc    3413
Ala Pro Gly Lys Gly Leu Glu Trp Val Ala Val Ile Ser Tyr Asp Ala
            150                 155                 160 aac tac aag tac tac gcc gat agc gtg aag gga cgg ttc acc atc agc    3461
Asn Tyr Lys Tyr Tyr Ala Asp Ser Val Lys Gly Arg Phe Thr Ile Ser
        165                 170                 175 cgg gat aac agc aag aac acc ctg tac ctg cag atg aac agc ctg cgg    3509
Arg Asp Asn Ser Lys Asn Thr Leu Tyr Leu Gln Met Asn Ser Leu Arg
    180                 185                 190 gcc gag gat acc gcc gtg tac tac tgc gcc aag gat agc cag ctg cgg    3557
Ala Glu Asp Thr Ala Val Tyr Tyr Cys Ala Lys Asp Ser Gln Leu Arg
195                 200                 205                 210 agc ctg ctg tac ttc gag tgg ctg agc cag gga tac ttc gat tac tgg    3605
Ser Leu Leu Tyr Phe Glu Trp Leu Ser Gln Gly Tyr Phe Asp Tyr Trp
                215                 220                 225
```

-continued

| | | |
|---|---|---|
| gga cag gga acc ctg gtg acc gtg agc agc gct agc acc aag gga cca<br>Gly Gln Gly Thr Leu Val Thr Val Ser Ser Ala Ser Thr Lys Gly Pro<br>230 235 240 | 3653 | |
| agc gtg ttc cca ctg gcc cca agc agc aag agc acc agc gga gga acc<br>Ser Val Phe Pro Leu Ala Pro Ser Ser Lys Ser Thr Ser Gly Gly Thr<br>245 250 255 | 3701 | |
| gcc gcc ctg gga tgc ctg gtg aag gat tac ttc cca gag cca gtg acc<br>Ala Ala Leu Gly Cys Leu Val Lys Asp Tyr Phe Pro Glu Pro Val Thr<br>260 265 270 | 3749 | |
| gtg agc tgg aac agc gga gcc ctg acc agc gga gtg cac acc ttc cca<br>Val Ser Trp Asn Ser Gly Ala Leu Thr Ser Gly Val His Thr Phe Pro<br>275 280 285 290 | 3797 | |
| gcc gtg ctg cag agc agc gga ctg tat agc ctg agc agc gtg gtg acc<br>Ala Val Leu Gln Ser Ser Gly Leu Tyr Ser Leu Ser Ser Val Val Thr<br>295 300 305 | 3845 | |
| gtg cca agc agc agc ctg gga acc cag acc tac atc tgc aac gtg aac<br>Val Pro Ser Ser Ser Leu Gly Thr Gln Thr Tyr Ile Cys Asn Val Asn<br>310 315 320 | 3893 | |
| cac aag cca agc aac acc aag gtg gat aag aag gtg gag cca aag agc<br>His Lys Pro Ser Asn Thr Lys Val Asp Lys Lys Val Glu Pro Lys Ser<br>325 330 335 | 3941 | |
| tgc gat aag acc cac acg tgc cct cct tgt cca gcc ccc gaa ctg ctg<br>Cys Asp Lys Thr His Thr Cys Pro Pro Cys Pro Ala Pro Glu Leu Leu<br>340 345 350 | 3989 | |
| ggc ggg cct agc gtg ttc ctg ttt ccc cct aag cct aaa gat aca ctg<br>Gly Gly Pro Ser Val Phe Leu Phe Pro Pro Lys Pro Lys Asp Thr Leu<br>355 360 365 370 | 4037 | |
| atg att agt aga acc cca gag gtc aca tgc gtg gtc gtg gac gtg tcc<br>Met Ile Ser Arg Thr Pro Glu Val Thr Cys Val Val Val Asp Val Ser<br>375 380 385 | 4085 | |
| cac gaa gag cct gac gtg aag ttc aac tgg tac gtg gat ggc gtg gag<br>His Glu Glu Pro Asp Val Lys Phe Asn Trp Tyr Val Asp Gly Val Glu<br>390 395 400 | 4133 | |
| gtg cac aat gct aag act aaa cca cgc gaa gag cag tat aat agt aca<br>Val His Asn Ala Lys Thr Lys Pro Arg Glu Glu Gln Tyr Asn Ser Thr<br>405 410 415 | 4181 | |
| tac cga gtc gtg tca gtc ctg aca gtg ctg cac cag gat tgg ctg aac<br>Tyr Arg Val Val Ser Val Leu Thr Val Leu His Gln Asp Trp Leu Asn<br>420 425 430 | 4229 | |
| ggc aag gag tat aag tgc aag gtg tct aac aag gcc ctg ccc gcc cct<br>Gly Lys Glu Tyr Lys Cys Lys Val Ser Asn Lys Ala Leu Pro Ala Pro<br>435 440 445 450 | 4277 | |
| atc gag aaa aca att agc aag gcc aaa ggg cag cca cgg gaa ccc cag<br>Ile Glu Lys Thr Ile Ser Lys Ala Lys Gly Gln Pro Arg Glu Pro Gln<br>455 460 465 | 4325 | |
| gtc tac act ctg cca ccc tca aga gat gaa ctg act aag aac cag gtc<br>Val Tyr Thr Leu Pro Pro Ser Arg Asp Glu Leu Thr Lys Asn Gln Val<br>470 475 480 | 4373 | |
| agc ctg acc tgt ctg gtg aaa ggc ttc tac ccc agc gac atc gcc gtg<br>Ser Leu Thr Cys Leu Val Lys Gly Phe Tyr Pro Ser Asp Ile Ala Val<br>485 490 495 | 4421 | |
| gag tgg gaa agt aac ggc cag cct gag aat aac tac aag act acc cct<br>Glu Trp Glu Ser Asn Gly Gln Pro Glu Asn Asn Tyr Lys Thr Thr Pro<br>500 505 510 | 4469 | |
| cca gtg ctg gat agc gac ggg tcc ttc ttc ctg tat agc aag ctg aca<br>Pro Val Leu Asp Ser Asp Gly Ser Phe Phe Leu Tyr Ser Lys Leu Thr<br>515 520 525 530 | 4517 | |
| gtg gac aaa tcc cgc tgg cag cag gga aac gtc ttt tcc tgt tct gtg<br>Val Asp Lys Ser Arg Trp Gln Gln Gly Asn Val Phe Ser Cys Ser Val<br>535 540 545 | 4565 | |

```
atg cat gag gcc ctg cac aat cat tac acc cag aag agt ctg tca ctg         4613
Met His Glu Ala Leu His Asn His Tyr Thr Gln Lys Ser Leu Ser Leu
            550                 555                 560 agc ccc ggc aaa tgataaaagg aacccgcgct atgacggcaa taaaaagaca              4665
Ser Pro Gly Lys
            565 gaataaaacc cacgggtgtt gggtcgtttg ttcataaacc cgggatcgat aaggatcttc        4725
ctagagcatg gctacgtaga taagtagcat ggcgggttaa tcattaacta caaggaaccc        4785
ctagtgatgg agttggccac tccctctctg cgcgctcgct cgctcactga ggccgggcga       4845
ccaaaggtcg cccgacgccc gggctttgcc cgggcggcct cagtgagcga gcgagcgcgc        4905
agccttaatt aacctaattc actggccgtc gttttacaac gtcgtgactg ggaaaaccct        4965
ggcgttaccc aacttaatcg ccttgcagca catcccccttt cgccagctg gcgtaatagc         5025
gaagaggccc gcaccgatcg cccttcccaa cagttgcgca gcctgaatgg cgaatgggac        5085
gcgccctgta gcggcgcatt aagcgcggcg ggtgtggtgg ttacgcgcag cgtgaccgct        5145
acacttgcca gcgccctagc gcccgctcct ttcgctttct tcccttcctt tctcgccacg        5205
ttcgccggct ttccccgtca agctctaaat cggggctcc ctttagggtt ccgatttagt         5265
gctttacggc acctcgaccc caaaaaactt gattagggtg atggttcacg tagtgggcca        5325
tcgccctgat agacggtttt cgccctttg acgttggagt ccacgttctt taatagtgga        5385
ctcttgttcc aaactggaac aacactcaac cctatctcgg tctattcttt tgatttataa        5445
gggattttgc cgatttcggc ctattggtta aaaaatgagc tgatttaaca aaaatttaac        5505
gcgaatttta acaaaatatt aacgcttaca atttaggtgg cacttttcgg ggaaatgtgc        5565
gcggaacccc tatttgttta tttttctaaa tacattcaaa tatgtatccg ctcatgagac        5625
aataaccctg ataaatgctt caataatatt gaaaaggaa gagtatgagt attcaacatt        5685
tccgtgtcgc ccttattccc ttttttgcgg cattttgcct tcctgttttt gctcacccag        5745
aaacgctggt gaaagtaaaa gatgctgaag atcagttggg tgcacgagtg ggttacatcg        5805
aactggatct caacagcggt aagatccttg agagttttcg ccccgaagaa cgttttccaa        5865
tgatgagcac ttttaaagtt ctgctatgtg gcgcggtatt atcccgtatt gacgccgggc        5925
aagagcaact cggtcgccgc atacactatt ctcagaatga cttggttgag tactcaccag        5985
tcacagaaaa gcatcttacg gatggcatga cagtaagaga attatgcagt gctgccataa        6045
ccatgagtga taacactgcg gccaacttac ttctgacaac gatcggagga ccgaaggagc        6105
taaccgcttt tttgcacaac atgggggatc atgtaactcg ccttgatcgt tgggaaccgg        6165
agctgaatga agccatacca aacgacgagc gtgacaccac gatgcctgta gcaatggcaa        6225
caacgttgcg caaactatta actggcgaac tacttactct agcttcccgg caacaattaa        6285
tagactggat ggaggcggat aaagttgcag gaccacttct gcgctcggcc cttccggctg        6345
gctggtttat tgctgataaa tctggagccg gtgagcgtgg gtctcgcggt atcattgcag        6405
cactggggcc agatggtaag ccctcccgta tcgtagttat ctacacgacg gggagtcagg        6465
caactatgga tgaacgaaat agacagatcg ctgagatagg tgcctcactg attaagcatt        6525
ggtaactgtc agaccaagtt tactcatata ctttagat tgatttaaaa cttcattttt         6585
aatttaaaag gatctaggtg aagatccttt ttgataatct catgaccaaa atcccttaac        6645
gtgagttttc gttccactga gcgtcagacc ccgtagaaaa gatcaaagga tcttcttgag        6705
atcctttttt tctgcgcgta atctgctgct tgcaaacaaa aaaaccaccg ctaccagcgg        6765
tggtttgttt gccggatcaa gagctaccaa ctcttttccc gaaggtaact ggcttcagca        6825
```

```
gagcgcagat accaaatact gttcttctag tgtagccgta gttaggccac cacttcaaga    6885
actctgtagc accgcctaca tacctcgctc tgctaatcct gttaccagtg gctgctgcca    6945
gtggcgataa gtcgtgtctt accgggttgg actcaagacg atagttaccg gataaggcgc    7005
agcggtcggg ctgaacgggg ggttcgtgca cacagcccag cttggagcga acgacctaca    7065
ccgaactgag atacctacag cgtgagctat gagaaagcgc cacgcttccc gaagggagaa    7125
aggcggacag gtatccggta agcggcaggg tcggaacagg agagcgcacg agggagcttc    7185 caggggaaa cgcctggtat ctttatagtc ctgtcgggtt tcgccacctc tgacttgagc     7245
gtcgattttt gtgatgctcg tcagggggc ggagcctatg gaaaaacgcc agcaacgcgg     7305 ccttttacg gttcctggcc ttttgctggc cttttgctca catgttcttt cctgcgttat      7365
cccctgattc tgtggataac cgtattaccg cctttgagtg agctgatacc gctcgccgca    7425
gccgaacgac cgagcgcagc gagtcagtga gcgaggaagc ggaagagcgc ccaatacgca    7485
aaccgcctct ccccgcgcgt tggccgattc attaatgcag ctggcacgac aggtttcccg    7545
actggaaagc gggcagtgag cgcaacgcaa ttaatgtgag ttagctcact cattaggcac    7605
cccaggcttt acactttatg cttccggctc gtatgttgtg tggaattgtg agcggataac    7665
aatttcacac aggaaacagc tatgaccatg attacgccag atttaattaa ggccttaatt    7725
aggctgcgcg ctcgctcgct c                                              7746
```

<210> SEQ ID NO 20
<211> LENGTH: 107
<212> TYPE: PRT
<213> ORGANISM: Artificial sequence
<220> FEATURE:
<223> OTHER INFORMATION: Synthetic Construct

<400> SEQUENCE: 20

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 21
<211> LENGTH: 129
<212> TYPE: PRT
<213> ORGANISM: Artificial sequence
<220> FEATURE:
<223> OTHER INFORMATION: Synthetic Construct

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

```
Ala Met His Trp Val Arg Gln Ala Pro Gly Lys Gly Leu Glu Trp Val
            35                  40                  45

Ala Val Ile Ser Tyr Asp Ala Asn Tyr Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Ser Leu Leu Tyr Phe Glu Trp Leu Ser
                100                 105                 110

Gln Gly Tyr Phe Asp Tyr Trp Gly Gln Gly Thr Leu Val Thr Val Ser
                115                 120                 125

Ser

<210> SEQ ID NO 22
<211> LENGTH: 107
<212> TYPE: PRT
<213> ORGANISM: Artificial sequence
<220> FEATURE:
<223> OTHER INFORMATION: Synthetic Construct

<400> SEQUENCE: 22

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His
            100                 105

<210> SEQ ID NO 23
<211> LENGTH: 223
<212> TYPE: PRT
<213> ORGANISM: Artificial sequence
<220> FEATURE:
<223> OTHER INFORMATION: Synthetic Construct

<400> SEQUENCE: 23

Thr Cys Pro Pro Cys Pro Ala Pro Glu Leu Leu Gly Gly Pro Ser Val
 1               5                  10                  15

Phe Leu Phe Pro Pro Lys Pro Lys Asp Thr Leu Met Ile Ser Arg Thr
                 20                  25                  30

Pro Glu Val Thr Cys Val Val Val Asp Val Ser His Glu Glu Pro Asp
             35                  40                  45

Val Lys Phe Asn Trp Tyr Val Asp Gly Val Glu Val His Asn Ala Lys
         50                  55                  60

Thr Lys Pro Arg Glu Glu Gln Tyr Asn Ser Thr Tyr Arg Val Val Ser
 65                  70                  75                  80

Val Leu Thr Val Leu His Gln Asp Trp Leu Asn Gly Lys Glu Tyr Lys
                 85                  90                  95
```

```
        Cys Lys Val Ser Asn Lys Ala Leu Pro Ala Pro Ile Glu Lys Thr Ile
                        100                 105                 110

Ser Lys Ala Lys Gly Gln Pro Arg Glu Pro Gln Val Tyr Thr Leu Pro
                    115                 120                 125

Pro Ser Arg Asp Glu Leu Thr Lys Asn Gln Val Ser Leu Thr Cys Leu
                130                 135                 140

Val Lys Gly Phe Tyr Pro Ser Asp Ile Ala Val Glu Trp Glu Ser Asn
        145                 150                 155                 160

Gly Gln Pro Glu Asn Asn Tyr Lys Thr Thr Pro Pro Val Leu Asp Ser
                        165                 170                 175

Asp Gly Ser Phe Phe Leu Tyr Ser Lys Leu Thr Val Asp Lys Ser Arg
                    180                 185                 190

Trp Gln Gln Gly Asn Val Phe Ser Cys Ser Val Met His Glu Ala Leu
                195                 200                 205

His Asn His Tyr Thr Gln Lys Ser Leu Ser Leu Ser Pro Gly Lys
                    210                 215                 220

<210> SEQ ID NO 24
<211> LENGTH: 7740
<212> TYPE: DNA
<213> ORGANISM: Artificial sequence
<220> FEATURE:
<223> OTHER INFORMATION: Plasmid carrying FI6 and CR8033 monoclonal
      antibodies
<220> FEATURE:
<221> NAME/KEY: polyA_signal
<222> LOCATION: (191)..(239)
<223> OTHER INFORMATION: synthetic polyA
<220> FEATURE:
<221> NAME/KEY: misc_feature
<222> LOCATION: (246)..(914)
<223> OTHER INFORMATION: complement - CH'2-3
<220> FEATURE:
<221> NAME/KEY: misc_feature
<222> LOCATION: (915)..(1235)
<223> OTHER INFORMATION: complement - CH'1
<220> FEATURE:
<221> NAME/KEY: misc_feature
<222> LOCATION: (1236)..(1622)
<223> OTHER INFORMATION: complement - CR8033\VH
<220> FEATURE:
<221> NAME/KEY: misc_feature
<222> LOCATION: (1623)..(1673)
<223> OTHER INFORMATION: complement - leader
<220> FEATURE:
<221> NAME/KEY: misc_feature
<222> LOCATION: (1683)..(1751)
<223> OTHER INFORMATION: CMV\mp2
<220> FEATURE:
<221> NAME/KEY: misc_feature
<222> LOCATION: (1752)..(2220)
<223> OTHER INFORMATION: Enhancer
<220> FEATURE:
<221> NAME/KEY: misc_feature
<222> LOCATION: (2221)..(2346)
<223> OTHER INFORMATION: CMV\mp1
<220> FEATURE:
<221> NAME/KEY: misc_feature
<222> LOCATION: (2406)..(2462)
<223> OTHER INFORMATION: leader
<220> FEATURE:
<221> NAME/KEY: CDS
<222> LOCATION: (2463)..(2795)
<223> OTHER INFORMATION: FI6\VL
<220> FEATURE:
<221> NAME/KEY: CDS
<222> LOCATION: (2796)..(3116)
<223> OTHER INFORMATION: CL
```

```
<220> FEATURE:
<221> NAME/KEY: misc_feature
<222> LOCATION: (3201)..(3260)
<223> OTHER INFORMATION: leader
<220> FEATURE:
<221> NAME/KEY: CDS
<222> LOCATION: (3261)..(3647)
<223> OTHER INFORMATION: FI6\VH
<220> FEATURE:
<221> NAME/KEY: CDS
<222> LOCATION: (3648)..(3968)
<223> OTHER INFORMATION: CH1
<220> FEATURE:
<221> NAME/KEY: CDS
<222> LOCATION: (3969)..(4637)
<223> OTHER INFORMATION: CH2-3
<220> FEATURE:
<221> NAME/KEY: misc_feature
<222> LOCATION: (3980)..(3980)
<223> OTHER INFORMATION: A -> T
<220> FEATURE:
<221> NAME/KEY: polyA_signal
<222> LOCATION: (4644)..(4721)
<223> OTHER INFORMATION: TKpAshort

<400> SEQUENCE: 24
```

| | | | | |
|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | tgtagttaat | gattaacccg | ccatgctact | tatctacgta | gccatgctct | 180 |
| aggaagatct | cacacaaaaa | accaacacac | agatgtaatg | aaaataaaga | tattttattt | 240 |
| tatcacttcc | cggggctcag | gctcaggac | ttctgggtgt | agtggttgtg | cagggcctcg | 300 |
| tgcatcacgc | tgcagctgaa | cacgttgccc | tgctgccacc | ggctcttgtc | cacggtcagc | 360 |
| ttgctataca | ggaagaatga | gccgtcgctg | tccagcacag | ggggggtggt | cttgtagttg | 420 |
| ttctcgggct | ggccgttgct | ctcccattcc | acggcgatct | cgctggggta | gaagcccttg | 480 |
| accaggcagg | tcaggacac | ctggttcttg | gtcatctctt | cccggctggg | gggcagtgtg | 540 |
| tagacctgag | gctcgcgggg | ctggcccttg | gccttgctga | tggttttctc | gatgggggca | 600 |
| ggcagggcct | tgttggacac | cttgcacttg | tactctttgc | cgttcagcca | gtcctggtgc | 660 |
| agcacggtca | gcacggacac | cacccggtag | gtgctgttgt | actgttcctc | tctgggcttg | 720 |
| gtcttggcgt | tgtgcacttc | cacgccgtcc | acgtaccaat | tgaacttcac | ttcagggtcc | 780 |
| tcgtgggaca | cgtccaccac | cacgcaggtc | acttcggggg | tccggctgat | catcagggtg | 840 |
| tccttgggct | ttgggggaa | caggaacacg | ctggggcctc | ccagcagttc | aggggcaggg | 900 |
| caggggggac | acgtgtgggt | cttgtcgcag | ctcttaggtt | ccacccgctt | gtccaccttg | 960 |
| gtgttgctgg | gcttgtggtt | cacgttgcag | atgtaggtct | gggtgcccag | gctgctgctg | 1020 |
| ggcacggtga | ccacgctgct | caggctatac | aggccgctgc | tctgcagcac | ggctggaaag | 1080 |
| gtgtgcacgc | cgctggtcag | ggcgccagag | ttccaggaca | cggtcacggg | ctcggggaag | 1140 |
| tagtccttga | ccaggcagcc | cagggcggct | gttccgccag | aggtgctctt | gctgctaggg | 1200 |
| gccagaggga | acacgcttgg | tcccttggtg | ctggcgctcg | agacggtcac | catggttccc | 1260 |
| tgtccccaga | tatcgaaggt | tcctccctcc | aggatatcca | tggcgctgct | ctccagccga | 1320 |
| tccttggcgc | agtagtacag | ggcggtatcc | tcggcccgca | ggctgttcat | ctgcaggtac | 1380 |
| aggctgttct | ttccgttatc | ccggctgatg | gtgaaccgtc | cctgcacgct | atcggcgtat | 1440 |
| cccatgaagt | ttcccttcca | gttgattccg | gccacccact | ccagtccctt | tcctggggcc | 1500 |
| tgccgcaccc | agtgcatggt | gtactcatcg | aagctgaatc | cgctggcggc | gcagctcagc | 1560 |

-continued

```
cgcaggctcc gtcctggctg caccagtcct cctccggtct ccaccagctg cacctctgaa    1620
ttcgtcacca gggccaggct cagggcgatc agcagcagca gctgcatgcg catggtggcg    1680
gcgcgatctg acggttcact aaacgagctc tgcttatata ggcctccac cgtacacgcc     1740 acctcgacat acctagttat taatagtaat caattacggg gtcattagtt catagcccat    1800
atatggagtt ccgcgttaca taacttacgg taaatggccc gcctggctga ccgcccaacg    1860
acccccgccc attgacgtca ataatgacgt atgttcccat agtaacgcca atagggactt    1920
tccattgacg tcaatgggtg gagtatttac ggtaaactgc ccacttggca gtacatcaag    1980
tgtatcatat gccaagtacg cccctattg acgtcaatga cggtaaatgg cccgcctggc     2040
attatgccca gtacatgacc ttatgggact ttcctacttg gcagtacatc tacgtattag    2100
tcatcgctat taccatggtg atgcggtttt ggcagtacat caatgggcgt ggatagcggt    2160
ttgactcacg gggatttcca gtctccacc ccattgacgt caatgggagt ttgttttggc     2220
accaaaatca acgggacttt ccaaaatgtc gtaacaactc cgccccattg acgcaaatgg    2280
gcggtaggcg tgtacggtgg gaggtctata taagcagagc tggtttagtg aaccgtcaga    2340
tccgctgggc actttgcact ggaacttaca cacccgagc aaggacgcga ctctgccgcc     2400
ccaccatgcg catgcagctg ctgctgctga tcgccctgag cctggccctg gtgaccaaca    2460 gc gat atc gtc atg acc cag agc cca gat agc ctg gcc gtg agc ctg       2507
   Asp Ile Val Met Thr Gln Ser Pro Asp Ser Leu Ala Val Ser Leu
    1               5                  10                  15 gga gag cgg gcc acc atc aac tgc aag agc agc cag agc gtg acc ttc      2555
Gly Glu Arg Ala Thr Ile Asn Cys Lys Ser Ser Gln Ser Val Thr Phe
                20                  25                  30 aac tac aag aac tac ctg gcc tgg tac cag cag aag cca gga cag cca      2603
Asn Tyr Lys Asn Tyr Leu Ala Trp Tyr Gln Gln Lys Pro Gly Gln Pro
            35                  40                  45 cca aag ctg ctg atc tac tgg gcc agc acc cgg gag agc gga gtg cca      2651
Pro Lys Leu Leu Ile Tyr Trp Ala Ser Thr Arg Glu Ser Gly Val Pro
        50                  55                  60 gat cgg ttc agc gga agc gga agc gga acc gat ttc acc ctg acc atc      2699
Asp Arg Phe Ser Gly Ser Gly Ser Gly Thr Asp Phe Thr Leu Thr Ile
    65                  70                  75 agc agc ctg cag gcc gag gat gtg gcc gtg tac tac tgc cag cag cac      2747
Ser Ser Leu Gln Ala Glu Asp Val Ala Val Tyr Tyr Cys Gln Gln His
80                  85                  90                  95 tac cgg acc cca cca acc ttc gga cag gga acc aag gtg gag atc aag      2795
Tyr Arg Thr Pro Pro Thr Phe Gly Gln Gly Thr Lys Val Glu Ile Lys
                100                 105                 110 cgt acg gtg gcc gcc cca agc gtg ttc atc ttc cca cca agc gat gag      2843
Arg Thr Val Ala Ala Pro Ser Val Phe Ile Phe Pro Pro Ser Asp Glu
            115                 120                 125 cag ctg aag agc gga acc gcc agc gtg gtg tgc ctg ctg aac aac ttc      2891
Gln Leu Lys Ser Gly Thr Ala Ser Val Val Cys Leu Leu Asn Asn Phe
        130                 135                 140 tac cca cgg gag gcc aag gtg cag tgg aag gtg gat aac gcc ctg cag      2939
Tyr Pro Arg Glu Ala Lys Val Gln Trp Lys Val Asp Asn Ala Leu Gln
    145                 150                 155 agc gga aac agc cag gag agc gtg acc gag cag gat agc aag gat agc      2987
Ser Gly Asn Ser Gln Glu Ser Val Thr Glu Gln Asp Ser Lys Asp Ser
160                 165                 170                 175 acc tac agc ctg agc agc acc ctg acc ctg agc aag gcc gat tac gag      3035
Thr Tyr Ser Leu Ser Ser Thr Leu Thr Leu Ser Lys Ala Asp Tyr Glu
                180                 185                 190
```

-continued

| | |
|---|---|
| aag cac aag gtg tac gcc tgc gag gtg acc cac cag gga ctg agc agc<br>Lys His Lys Val Tyr Ala Cys Glu Val Thr His Gln Gly Leu Ser Ser<br>               195                          200                  205 | 3083 |
| cca gtg acc aag agc ttc aac cgc gga gag tgc cggaagcggc gggcccagt<br>Pro Val Thr Lys Ser Phe Asn Arg Gly Glu Cys<br>               210                         215 | 3136 |
| gaagcagacc ctgaacttcg atctgctgaa gctggccgga gatgtggaga gcaacccagg | 3196 |
| accaatgtac agaatgcagc tgctgagctg catcgccctg agcctggccc tggtgaccaa | 3256 |
| cagc cag gtg caa cta gtg gag agc gga gga gga gtg gtg cag cca gga<br>      Gln Val Gln Leu Val Glu Ser Gly Gly Gly Val Val Gln Pro Gly<br>          220                          225                          230 | 3305 |
| cgg agc ctg cgg ctg agc tgc gcc gcc agc gga ttc acc ttc agc acc<br>Arg Ser Leu Arg Leu Ser Cys Ala Ala Ser Gly Phe Thr Phe Ser Thr<br>    235                         240                         245 | 3353 |
| tac gcc atg cac tgg gtg cgg cag gcc cca gga aag gga ctg gag tgg<br>Tyr Ala Met His Trp Val Arg Gln Ala Pro Gly Lys Gly Leu Glu Trp<br>250                       255                       260                       265 | 3401 |
| gtg gcc gtg atc agc tac gat gcc aac tac aag tac tac gcc gat agc<br>Val Ala Val Ile Ser Tyr Asp Ala Asn Tyr Lys Tyr Tyr Ala Asp Ser<br>                       270                         275                       280 | 3449 |
| gtg aag gga cgg ttc acc atc agc cgg gat aac agc aag aac acc ctg<br>Val Lys Gly Arg Phe Thr Ile Ser Arg Asp Asn Ser Lys Asn Thr Leu<br>              285                         290                       295 | 3497 |
| tac ctg cag atg aac agc ctg cgg gcc gag gat acc gcc gtg tac tac<br>Tyr Leu Gln Met Asn Ser Leu Arg Ala Glu Asp Thr Ala Val Tyr Tyr<br>                       300                         305                       310 | 3545 |
| tgc gcc aag gat agc cag ctg cgg agc ctg ctg tac ttc gag tgg ctg<br>Cys Ala Lys Asp Ser Gln Leu Arg Ser Leu Leu Tyr Phe Glu Trp Leu<br>315                       320                       325 | 3593 |
| agc cag gga tac ttc gat tac tgg gga cag gga acc ctg gtg acc gtg<br>Ser Gln Gly Tyr Phe Asp Tyr Trp Gly Gln Gly Thr Leu Val Thr Val<br>330                       335                       340                       345 | 3641 |
| agc agc gct agc acc aag gga cca agc gtg ttc cca ctg gcc cca agc<br>Ser Ser Ala Ser Thr Lys Gly Pro Ser Val Phe Pro Leu Ala Pro Ser<br>                 350                         355                       360 | 3689 |
| agc aag agc acc agc gga gga acc gcc gcc ctg gga tgc ctg gtg aag<br>Ser Lys Ser Thr Ser Gly Gly Thr Ala Ala Leu Gly Cys Leu Val Lys<br>           365                         370                       375 | 3737 |
| gat tac ttc cca gag cca gtg acc gtg agc tgg aac agc gga gcc ctg<br>Asp Tyr Phe Pro Glu Pro Val Thr Val Ser Trp Asn Ser Gly Ala Leu<br>        380                         385                       390 | 3785 |
| acc agc gga gtg cac acc ttc cca gcc gtg ctg cag agc agc gga ctg<br>Thr Ser Gly Val His Thr Phe Pro Ala Val Leu Gln Ser Ser Gly Leu<br>395                       400                       405 | 3833 |
| tat agc ctg agc agc gtg gtg acc gtg cca agc agc agc ctg gga acc<br>Tyr Ser Leu Ser Ser Val Val Thr Val Pro Ser Ser Ser Leu Gly Thr<br>410                       415                       420                       425 | 3881 |
| cag acc tac atc tgc aac gtg aac cac aag cca agc aac acc aag gtg<br>Gln Thr Tyr Ile Cys Asn Val Asn His Lys Pro Ser Asn Thr Lys Val<br>                       430                         435                       440 | 3929 |
| gat aag aag gtg gag cca aag agc tgc gat aag acc cac acg tgc cct<br>Asp Lys Lys Val Glu Pro Lys Ser Cys Asp Lys Thr His Thr Cys Pro<br>                       445                         450                       455 | 3977 |
| cct tgt cca gcc ccc gaa ctg ctg ggc ggg cct agc gtg ttc ctg ttt<br>Pro Cys Pro Ala Pro Glu Leu Leu Gly Gly Pro Ser Val Phe Leu Phe<br>        460                         465                       470 | 4025 |
| ccc cct aag cct aaa gat aca ctg atg att agt aga acc cca gag gtc<br>Pro Pro Lys Pro Lys Asp Thr Leu Met Ile Ser Arg Thr Pro Glu Val<br>475                       480                       485 | 4073 |

```
aca tgc gtg gtc gtg gac gtg tcc cac gaa gag cct gac gtg aag ttc    4121
Thr Cys Val Val Val Asp Val Ser His Glu Glu Pro Asp Val Lys Phe
490             495                 500                 505 aac tgg tac gtg gat ggc gtg gag gtg cac aat gct aag act aaa cca    4169
Asn Trp Tyr Val Asp Gly Val Glu Val His Asn Ala Lys Thr Lys Pro
                510                 515                 520 cgc gaa gag cag tat aat agt aca tac cga gtc gtg tca gtc ctg aca    4217
Arg Glu Glu Gln Tyr Asn Ser Thr Tyr Arg Val Val Ser Val Leu Thr
            525                 530                 535 gtg ctg cac cag gat tgg ctg aac ggc aag gag tat aag tgc aag gtg    4265
Val Leu His Gln Asp Trp Leu Asn Gly Lys Glu Tyr Lys Cys Lys Val
        540                 545                 550 tct aac aag gcc ctg ccc gcc cct atc gag aaa aca att agc aag gcc    4313
Ser Asn Lys Ala Leu Pro Ala Pro Ile Glu Lys Thr Ile Ser Lys Ala
    555                 560                 565 aaa ggg cag cca cgg gaa ccc cag gtc tac act ctg cca ccc tca aga    4361
Lys Gly Gln Pro Arg Glu Pro Gln Val Tyr Thr Leu Pro Pro Ser Arg
570                 575                 580                 585 gat gaa ctg act aag aac cag gtc agc ctg acc tgt ctg gtg aaa ggc    4409
Asp Glu Leu Thr Lys Asn Gln Val Ser Leu Thr Cys Leu Val Lys Gly
                590                 595                 600 ttc tac ccc agc gac atc gcc gtg gag tgg gaa agt aac ggc cag cct    4457
Phe Tyr Pro Ser Asp Ile Ala Val Glu Trp Glu Ser Asn Gly Gln Pro
                605                 610                 615 gag aat aac tac aag act acc cct cca gtg ctg gat agc gac ggg tcc    4505
Glu Asn Asn Tyr Lys Thr Thr Pro Pro Val Leu Asp Ser Asp Gly Ser
            620                 625                 630 ttc ttc ctg tat agc aag ctg aca gtg gac aaa tcc cgc tgg cag cag    4553
Phe Phe Leu Tyr Ser Lys Leu Thr Val Asp Lys Ser Arg Trp Gln Gln
        635                 640                 645 gga aac gtc ttt tcc tgt tct gtg atg cat gag gcc ctg cac aat cat    4601
Gly Asn Val Phe Ser Cys Ser Val Met His Glu Ala Leu His Asn His
650                 655                 660                 665 tac acc cag aag agt ctg tca ctg agc ccc ggc aaa tgataaaagg         4647
Tyr Thr Gln Lys Ser Leu Ser Leu Ser Pro Gly Lys
                670                 675 aacccgcgct atgacggcaa taaaaagaca gaataaaacc cacgggtgtt gggtcgtttg    4707
ttcataaacc cgggatcgat aaggatcttc ctagagcatg gctacgtaga taagtagcat    4767
ggcgggttaa tcattaacta caaggaaccc ctagtgatgg agttggccac tccctctctg    4827
cgcgctcgct cgctcactga ggccgggcga ccaaaggtcg cccgacgccc gggctttgcc    4887
cgggcggcct cagtgagcga gcgagcgcgc agccttaatt aacctaattc actggccgtc    4947
gttttacaac gtcgtgactg ggaaaaccct ggcgttaccc aacttaatcg ccttgcagca    5007
catccccctt tcgccagctg gcgtaatagc gaagaggccc gcaccgatcg cccttcccaa    5067
cagttgcgca gcctgaatgg cgaatgggac gcgccctgta gcggcgcatt aagcgcggcg    5127
ggtgtggtgg ttacgcgcag cgtgaccgct acacttgcca gcgccctagc gcccgctcct    5187
ttcgctttct tcccttcctt tctcgccacg ttcgccggct ttccccgtca gctctaaat     5247 cgggggctcc ctttagggtt ccgatttagt gctttacggc acctcgaccc caaaaaactt    5307
gattagggtg atggttcacg tagtgggcca tcgccctgat agacggtttt tcgccctttg    5367
acgttggagt ccacgttctt taatagtgga ctcttgttcc aaactggaac aacactcaac    5427
cctatctcgg tctattcttt tgatttataa gggattttgc cgatttcggc ctattggtta    5487
aaaaatgagc tgatttaaca aaaatttaac gcgaatttta acaaaatatt aacgcttaca    5547
atttaggtgg cacttttcgg ggaaatgtgc gcggaacccc tatttgttta tttttctaaa    5607
```

| | | | | |
|---|---|---|---|---|
| tacattcaaa | tatgtatccg | ctcatgagac | aataaccctg | ataaatgctt caataatatt | 5667 |
| gaaaaaggaa | gagtatgagt | attcaacatt | tccgtgtcgc | ccttattccc tttttttgcgg | 5727 |
| cattttgcct | tcctgttttt | gctcacccag | aaacgctggt | gaaagtaaaa gatgctgaag | 5787 |
| atcagttggg | tgcacgagtg | ggttacatcg | aactggatct | caacagcggt aagatccttg | 5847 |
| agagttttcg | ccccgaagaa | cgttttccaa | tgatgagcac | ttttaaagtt ctgctatgtg | 5907 |
| gcgcggtatt | atcccgtatt | gacgccgggc | aagagcaact | cggtcgccgc atacactatt | 5967 |
| ctcagaatga | cttggttgag | tactcaccag | tcacagaaaa | gcatcttacg gatggcatga | 6027 |
| cagtaagaga | attatgcagt | gctgccataa | ccatgagtga | taacactgcg gccaacttac | 6087 |
| ttctgacaac | gatcggagga | ccgaaggagc | taaccgcttt | tttgcacaac atgggggatc | 6147 |
| atgtaactcg | ccttgatcgt | tgggaaccgg | agctgaatga | agccatacca acgacgagc | 6207 |
| gtgacaccac | gatgcctgta | gcaatggcaa | caacgttgcg | caaactatta actggcgaac | 6267 |
| tacttactct | agcttcccgg | caacaattaa | tagactggat | ggaggcggat aaagttgcag | 6327 |
| gaccacttct | gcgctcggcc | cttccggctg | gctggtttat | tgctgataaa tctggagccg | 6387 |
| gtgagcgtgg | gtctcgcggt | atcattgcag | cactggggcc | agatggtaag ccctcccgta | 6447 |
| tcgtagttat | ctacacgacg | gggagtcagg | caactatgga | tgaacgaaat agacagatcg | 6507 |
| ctgagatagg | tgcctcactg | attaagcatt | ggtaactgtc | agaccaagtt tactcatata | 6567 |
| tactttagat | tgatttaaaa | cttcattttt | aatttaaaag | gatctaggtg aagatccttt | 6627 |
| ttgataatct | catgaccaaa | atcccttaac | gtgagttttc | gttccactga gcgtcagacc | 6687 |
| ccgtagaaaa | gatcaaagga | tcttcttgag | atcctttttt | tctgcgcgta atctgctgct | 6747 |
| tgcaaacaaa | aaaaccaccg | ctaccagcgg | tggtttgttt | gccggatcaa gagctaccaa | 6807 |
| ctcttttccc | gaaggtaact | ggcttcagca | gagcgcagat | accaaatact gttcttctag | 6867 |
| tgtagccgta | gttaggccac | cacttcaaga | actctgtagc | accgcctaca tacctcgctc | 6927 |
| tgctaatcct | gttaccagtg | gctgctgcca | gtggcgataa | gtcgtgtctt accgggttgg | 6987 |
| actcaagacg | atagttaccg | gataaggcgc | agcggtcggg | ctgaacgggg ggttcgtgca | 7047 |
| cacagcccag | cttggagcga | acgacctaca | ccgaactgag | atacctacag cgtgagctat | 7107 |
| gagaaagcgc | cacgcttccc | gaagggagaa | aggcggacag | gtatccggta agcggcaggg | 7167 |
| tcggaacagg | agagcgcacg | agggagcttc | caggggggaaa | cgcctggtat ctttatagtc | 7227 |
| ctgtcgggtt | tcgccacctc | tgacttgagc | gtcgattttt | gtgatgctcg tcaggggggc | 7287 |
| ggagcctatg | gaaaaacgcc | agcaacgcgg | ccttttttacg | gttcctggcc ttttgctggc | 7347 |
| cttttgctca | catgttcttt | cctgcgttat | cccctgattc | tgtggataac cgtattaccg | 7407 |
| cctttgagtg | agctgatacc | gctcgccgca | gccgaacgac | cgagcgcagc gagtcagtga | 7467 |
| gcgaggaagc | ggaagagcgc | ccaatacgca | aaccgcctct | ccccgcgcgt tggccgattc | 7527 |
| attaatgcag | ctggcacgac | aggtttcccg | actggaaagc | gggcagtgag cgcaacgcaa | 7587 |
| ttaatgtgag | ttagctcact | cattaggcac | cccaggcttt | acactttatg cttccggctc | 7647 |
| gtatgttgtg | tggaattgtg | agcggataac | aatttcacac | aggaaacagc tatgaccatg | 7707 |
| attacgccag | atttaattaa | ggccttaatt | agg | | 7740 |

<210> SEQ ID NO 25
<211> LENGTH: 111
<212> TYPE: PRT
<213> ORGANISM: Artificial sequence
<220> FEATURE:
<223> OTHER INFORMATION: Synthetic Construct -continued

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110

<210> SEQ ID NO 26
<211> LENGTH: 107
<212> TYPE: PRT
<213> ORGANISM: Artificial sequence
<220> FEATURE:
<223> OTHER INFORMATION: Synthetic Construct

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 27
<211> LENGTH: 129
<212> TYPE: PRT
<213> ORGANISM: Artificial sequence
<220> FEATURE:
<223> OTHER INFORMATION: Synthetic Construct

<400> SEQUENCE: 27

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

-continued

```
Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
           100                 105                 110

Gln Gly Tyr Phe Asp Tyr Trp Gly Gln Gly Thr Leu Val Thr Val Ser
       115                 120                 125

Ser
```

<210> SEQ ID NO 28
<211> LENGTH: 107
<212> TYPE: PRT
<213> ORGANISM: Artificial sequence
<220> FEATURE:
<223> OTHER INFORMATION: Synthetic Construct

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105
```

<210> SEQ ID NO 29
<211> LENGTH: 223
<212> TYPE: PRT
<213> ORGANISM: Artificial sequence
<220> FEATURE:
<223> OTHER INFORMATION: Synthetic Construct

<400> SEQUENCE: 29

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140
```

```
Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 30
<211> LENGTH: 7782
<212> TYPE: DNA
<213> ORGANISM: Artificial
<220> FEATURE:
<223> OTHER INFORMATION: EcoRV
<220> FEATURE:
<221> NAME/KEY: polyA_signal
<222> LOCATION: (201)..(252)
<223> OTHER INFORMATION: complement - synthetic\polyA
<220> FEATURE:
<221> NAME/KEY: misc_feature
<222> LOCATION: (268)..(588)
<223> OTHER INFORMATION: complement - CL
<220> FEATURE:
<221> NAME/KEY: misc_feature
<222> LOCATION: (589)..(909)
<223> OTHER INFORMATION: complement - TCN032\VL
<220> FEATURE:
<221> NAME/KEY: polyA_signal
<222> LOCATION: (910)..(966)
<223> OTHER INFORMATION: complement - leader
<220> FEATURE:
<221> NAME/KEY: misc_feature
<222> LOCATION: (1026)..(1094)
<223> OTHER INFORMATION: complement - CMV\mp2
<220> FEATURE:
<221> NAME/KEY: misc_feature
<222> LOCATION: (1095)..(1563)
<223> OTHER INFORMATION: Enhancer
<220> FEATURE:
<221> NAME/KEY: misc_feature
<222> LOCATION: (1564)..(1689)
<223> OTHER INFORMATION: CMV\mp1
<220> FEATURE:
<221> NAME/KEY: misc_feature
<222> LOCATION: (1749)..(1805)
<223> OTHER INFORMATION: leader
<220> FEATURE:
<221> NAME/KEY: CDS
<222> LOCATION: (1806)..(2165)
<223> OTHER INFORMATION: TCN032\VH
<220> FEATURE:
<221> NAME/KEY: CDS
<222> LOCATION: (2166)..(2459)
<223> OTHER INFORMATION: CH1
<220> FEATURE:
<221> NAME/KEY: misc_feature
<222> LOCATION: (2460)..(3152)
<223> OTHER INFORMATION: hinge-CH2'-CH3'
<220> FEATURE:
<221> NAME/KEY: misc_feature
<222> LOCATION: (3239)..(3296)
<223> OTHER INFORMATION: leader
<220> FEATURE:
<221> NAME/KEY: CDS
<222> LOCATION: (3297)..(3683)
<223> OTHER INFORMATION: FI6\VH
<220> FEATURE:
<221> NAME/KEY: CDS
<222> LOCATION: (3684)..(4004)
<223> OTHER INFORMATION: CH1
```

```
<220> FEATURE:
<221> NAME/KEY: CDS
<222> LOCATION: (4005)..(4673)
<223> OTHER INFORMATION: CH2-3
<220> FEATURE:
<221> NAME/KEY: polyA_signal
<222> LOCATION: (4693)..(4770)
<223> OTHER INFORMATION: TKpAshort

<400> SEQUENCE: 30
```

| | |
|---|---|
| ggccttaatt aggctgcgcg ctcgctcgct cactgaggcc gcccgggcaa agcccgggcg | 60 |
| tcgggcgacc tttggtcgcc cggcctcagt gagcgagcga gcgcgcagag agggagtggc | 120 |
| caactccatc actaggggtt ccttgtagtt aatgattaac cgccatgct acttatctac | 180 |
| gtagccatgc tctaggaaga tctcacacaa aaaaccaaca cacagatgta atgaaaataa | 240 |
| agatatttta ttgcggccgc tttatcagca ctctccgcgg ttgaagctct tggtcactgg | 300 |
| gctgctcagt ccctggtggg tcacctcgca ggcgtacacc ttgtgcttct cgtaatcggc | 360 |
| cttgctcagg gtcagggtgc tgctcaggct gtaggtgcta tccttgctat cctgctcggt | 420 |
| cacgctctcc tggctgtttc cgctctgcag ggcgttatcc accttccact gcaccttggc | 480 |
| ctcccgtggg tagaagttgt tcagcaggca caccacgctg gcggttccgc tcttcagctg | 540 |
| ctcatcgctt ggtgggaaga tgaacacgct tggggcggcc accgtacgct tgatctccac | 600 |
| ccgggttcct cctccgaagg tcagtggtgg gctgtagctc tgctggcagt agtaggtggc | 660 |
| gaaatcctct ggctgcaggc tggtgatggt cagggtgaaa tcggttccgc ttccgcttcc | 720 |
| gctgaaccgg cttggcactc cgctctgcag tccgctggcg gcgctgatca gtcccttgg | 780 |
| ggcctttcct ggccgctgct ggtaccagtt caggtacttg tagatgttct ggctggcccg | 840 |
| gcaggtgatg tcacccgat ctcccacgct ggcgctcagg ctgcttgggc tctgggtcat | 900 |
| ctggatatcg ctgttggtca ccagggccag gctcagggcg atcagcagca gcagctgcat | 960 |
| tctcatggtg gagagtcgcg tccttgctcg ggtgttgtaa gttccagtgc aaagtgcccc | 1020 |
| aattggcgat ctgacggttc actaaacgag ctctgcttat ataggcctcc caccgtacac | 1080 |
| gccacctcga catacctagt tattaatagt aatcaattac ggggtcatta gttcatagcc | 1140 |
| catatatgga gttccgcgtt acataactta cggtaaatgg cccgcctggc tgaccgccca | 1200 |
| acgaccccg cccattgacg tcaataatga cgtatgttcc catagtaacg ccaataggga | 1260 |
| ctttccattg acgtcaatgg gtggagtatt tacggtaaac tgcccacttg gcagtacatc | 1320 |
| aagtgtatca tatgccaagt acgccccta ttgacgtcaa tgacggtaaa tggcccgcct | 1380 |
| ggcattatgc ccagtacatg acctatggg actttcctac ttggcagtac atctacgtat | 1440 |
| tagtcatcgc tattaccatg gtgatgcggt tttggcagta catcaatggg cgtggatagc | 1500 |
| ggtttgactc acggggattt ccaagtctcc accccattga cgtcaatggg agtttgtttt | 1560 |
| ggcaccaaaa tcaacgggac tttccaaaat gtcgtaacaa ctccgcccca ttgacgcaaa | 1620 |
| tgggcggtag gcgtgtacgg tgggaggtct atataagcag agctggttta gtgaaccgtc | 1680 |
| agatccgctg ctagcgggca ctttgcactg gaacttacaa caccccgagca aggacgcgac | 1740 |
| tctccaccat gcgcatgcag ctgctgctgc tgatcgccct gagcctggcc ctggtgacca | 1800 |

```
acagc cag gtg cag ctg cag gag agc gga cca gga ctg gtg aag cca agc    1850
      Gln Val Gln Leu Gln Glu Ser Gly Pro Gly Leu Val Lys Pro Ser
      1               5                   10                  15 gag acc ctg agc ctg acc tgc acc gtg agc gga agc agc atc agc aac    1898
Glu Thr Leu Ser Leu Thr Cys Thr Val Ser Gly Ser Ser Ile Ser Asn
            20                  25                  30
```

```
tac tac tgg agc tgg atc cgg cag agc cca gga aag gga ctg gag tgg    1946
Tyr Tyr Trp Ser Trp Ile Arg Gln Ser Pro Gly Lys Gly Leu Glu Trp
                35                  40                  45 atc gga ttc atc tac tac gga gga aac acc aag tac aac cca agc ctg    1994
Ile Gly Phe Ile Tyr Tyr Gly Gly Asn Thr Lys Tyr Asn Pro Ser Leu
        50                  55                  60 aag agc cgg gtg acc atc agc cag gat acc agc aag agc cag gtg agc    2042
Lys Ser Arg Val Thr Ile Ser Gln Asp Thr Ser Lys Ser Gln Val Ser
 65                  70                  75 ctg acc atg agc agc gtg acc gcc gcc gag agc gcc gtg tac ttc tgc    2090
Leu Thr Met Ser Ser Val Thr Ala Ala Glu Ser Ala Val Tyr Phe Cys
 80                  85                  90                  95 gcc cgg gcc agc tgc agc gga gga tac tgc atc ctg gat tac tgg gga    2138
Ala Arg Ala Ser Cys Ser Gly Gly Tyr Cys Ile Leu Asp Tyr Trp Gly
                100                 105                 110 cag gga acc ctg gtg acc gtg agc agc gcg tcg acc aag gga cct tcg    2186
Gln Gly Thr Leu Val Thr Val Ser Ser Ala Ser Thr Lys Gly Pro Ser
        115                 120                 125 gtc ttc ccc ctg gca ccc tcc tcc aag agc acc tct ggg ggc aca gcg    2234
Val Phe Pro Leu Ala Pro Ser Ser Lys Ser Thr Ser Gly Gly Thr Ala
130                 135                 140 gcc ctg ggc tgc ctg gtc aag gac tac ttc ccc gaa ccg gtg acg gtg    2282
Ala Leu Gly Cys Leu Val Lys Asp Tyr Phe Pro Glu Pro Val Thr Val
    145                 150                 155 tcg tgg aac tca ggc gcc ctg acc agc ggc gtg cac acc ttc ccg gct    2330
Ser Trp Asn Ser Gly Ala Leu Thr Ser Gly Val His Thr Phe Pro Ala
160                 165                 170                 175 gtc cta cag tcc tca gga ctc tac tcc ctc agc agc gtg gtg acc gtg    2378
Val Leu Gln Ser Ser Gly Leu Tyr Ser Leu Ser Ser Val Val Thr Val
        180                 185                 190 ccc tcc agc agc ttg ggc acc cag acc tac atc tgc aac gtg aat cac    2426
Pro Ser Ser Ser Leu Gly Thr Gln Thr Tyr Ile Cys Asn Val Asn His
            195                 200                 205 aag ccc agc aac acc aag gtg gac aag aaa gtt gaaccaaaga gctgcgacaa   2479
Lys Pro Ser Asn Thr Lys Val Asp Lys Lys Val
                210                 215 gacccacacg tgtcccccct gccctgcccc tgaactgctg ggaggcccca gcgtgttcct   2539 gttccccca aagcccaagg acaccctgat gatcagccgg accccgaag tgacctgcgt    2599 ggtggtggac gtgtcccacg aggaccctga agtgaagttt aattggtacg tggacggcgt   2659
ggaagtgcac aacgccaaga ccaagcccag agaggaacag tacaacagca cctaccgggt   2719
ggtgtccgtg ctgaccgtgc tgcaccagga ctggctgaac ggcaaagagt acaagtgcaa   2779
ggtgtccaac aaggccctgc ctgccccat cgagaaaacc atcagcaagg ccaagggcca    2839
gccccgcgag cctcaggtct acacactgcc ccccagccgg gaagagatga ccaagaacca   2899
ggtgtccctg acctgcctgg tcaagggctt ctaccccagc gacatcgccg tggaatggga   2959
gagcaacggc cagcccgaga caactacaa gaccaccccc cctgtgctgg acagcgacgg   3019
ctcattcttc ctgtatagca agctgaccgt ggacaagagc cggtggcagc agggcaacgt   3079
gttcagctgc agcgtgatgc acgaggccct gcacaaccac tacacccaga gtccctgag    3139 cctgagcccc ggcagaaagc ggagagcccc cgtgaagcag accctgaact cgacctgct    3199 gaagctggcc ggcgacgtgg aaagcaaccc tggccctatg tacagaatgc agctgctgag   3259
ctgcatcgcc ctgagcctgg ccctggtgac caacagc cag gtg caa cta gtg gag    3314
                                        Gln Val Gln Leu Val Glu
                                                220
```

-continued

| | |
|---|---|
| agc gga gga gga gtg gtg cag cca gga cgg agc ctg cgg ctg agc tgc<br>Ser Gly Gly Gly Val Val Gln Pro Gly Arg Ser Leu Arg Leu Ser Cys<br>225                    230                 235                 240 | 3362 |
| gcc gcc agc gga ttc acc ttc agc acc tac gcc atg cac tgg gtg cgg<br>Ala Ala Ser Gly Phe Thr Phe Ser Thr Tyr Ala Met His Trp Val Arg<br>                     245                 250                 255 | 3410 |
| cag gcc cca gga aag gga ctg gag tgg gtg gcc gtg atc agc tac gat<br>Gln Ala Pro Gly Lys Gly Leu Glu Trp Val Ala Val Ile Ser Tyr Asp<br>   260                 265                 270 | 3458 |
| gcc aac tac aag tac tac gcc gat agc gtg aag gga cgg ttc acc atc<br>Ala Asn Tyr Lys Tyr Tyr Ala Asp Ser Val Lys Gly Arg Phe Thr Ile<br>275                     280                 285 | 3506 |
| agc cgg gat aac agc aag aac acc ctg tac ctg cag atg aac agc ctg<br>Ser Arg Asp Asn Ser Lys Asn Thr Leu Tyr Leu Gln Met Asn Ser Leu<br>         290                 295                 300 | 3554 |
| cgg gcc gag gat acc gcc gtg tac tac tgc gcc aag gat agc cag ctg<br>Arg Ala Glu Asp Thr Ala Val Tyr Tyr Cys Ala Lys Asp Ser Gln Leu<br>305                     310                 315                 320 | 3602 |
| cgg agc ctg ctg tac ttc gag tgg ctg agc cag gga tac ttc gat tac<br>Arg Ser Leu Leu Tyr Phe Glu Trp Leu Ser Gln Gly Tyr Phe Asp Tyr<br>                     325                 330                 335 | 3650 |
| tgg gga cag gga acc ctg gtg acc gtg agc agc gcc agc acc aag ggg<br>Trp Gly Gln Gly Thr Leu Val Thr Val Ser Ser Ala Ser Thr Lys Gly<br>   340                 345                 350 | 3698 |
| ccc agc gtg ttc cca ctg gcc cca agc agc aag agc acc agc gga gga<br>Pro Ser Val Phe Pro Leu Ala Pro Ser Ser Lys Ser Thr Ser Gly Gly<br>355                     360                 365 | 3746 |
| acc gcc gcc ctg gga tgc ctg gtg aag gat tac ttc cca gag cca gtg<br>Thr Ala Ala Leu Gly Cys Leu Val Lys Asp Tyr Phe Pro Glu Pro Val<br>         370                 375                 380 | 3794 |
| acc gtg agc tgg aac agc gga gcc ctg acc agc gga gtg cac acc ttc<br>Thr Val Ser Trp Asn Ser Gly Ala Leu Thr Ser Gly Val His Thr Phe<br>385                     390                 395                 400 | 3842 |
| cca gcc gtg ctg cag agc agc gga ctg tat agc ctg agc agc gtg gtg<br>Pro Ala Val Leu Gln Ser Ser Gly Leu Tyr Ser Leu Ser Ser Val Val<br>                     405                 410                 415 | 3890 |
| acc gtg cca agc agc agc ctg gga acc cag acc tac atc tgc aac gtg<br>Thr Val Pro Ser Ser Ser Leu Gly Thr Gln Thr Tyr Ile Cys Asn Val<br>         420                 425                 430 | 3938 |
| aac cac aag cca agc aac acc aag gtg gat aag aag gtg gag cca aag<br>Asn His Lys Pro Ser Asn Thr Lys Val Asp Lys Lys Val Glu Pro Lys<br>                     435                 440                 445 | 3986 |
| agc tgc gat aag acc cac acg tgc cct cca tgt cca gcc ccc gaa ctg<br>Ser Cys Asp Lys Thr His Thr Cys Pro Pro Cys Pro Ala Pro Glu Leu<br>450                     455                 460 | 4034 |
| ctg ggc ggg cct agc gtg ttc ctg ttt ccc cct aag cct aaa gat aca<br>Leu Gly Gly Pro Ser Val Phe Leu Phe Pro Pro Lys Pro Lys Asp Thr<br>465                     470                 475                 480 | 4082 |
| ctg atg att agt aga acc cca gag gtc aca tgc gtg gtc gtg gac gtg<br>Leu Met Ile Ser Arg Thr Pro Glu Val Thr Cys Val Val Val Asp Val<br>                     485                 490                 495 | 4130 |
| tcc cac gaa gag cct gac gtg aag ttc aac tgg tac gtg gat ggc gtg<br>Ser His Glu Glu Pro Asp Val Lys Phe Asn Trp Tyr Val Asp Gly Val<br>         500                 505                 510 | 4178 |
| gag gtg cac aat gct aag act aaa cca cgc gaa gag cag tat aat agt<br>Glu Val His Asn Ala Lys Thr Lys Pro Arg Glu Glu Gln Tyr Asn Ser<br>                   515                 520                 525 | 4226 |
| aca tac cga gtc gtg tca gtc ctg aca gtg ctg cac cag gat tgg ctg<br>Thr Tyr Arg Val Val Ser Val Leu Thr Val Leu His Gln Asp Trp Leu<br>530                     535                 540 | 4274 |

| | | |
|---|---|---|
| aac ggc aag gag tat aag tgc aag gtg tct aac aag gcc ctg ccc gcc<br>Asn Gly Lys Glu Tyr Lys Cys Lys Val Ser Asn Lys Ala Leu Pro Ala<br>545                     550                 555                   560 | 4322 |
| cct atc gag aaa aca att agc aag gcc aaa ggg cag cca cgg gaa ccc<br>Pro Ile Glu Lys Thr Ile Ser Lys Ala Lys Gly Gln Pro Arg Glu Pro<br>                   565                 570                 575 | 4370 |
| cag gtc tac act ctg cca ccc tca aga gat gaa ctg act aag aac cag<br>Gln Val Tyr Thr Leu Pro Pro Ser Arg Asp Glu Leu Thr Lys Asn Gln<br>               580                 585                 590 | 4418 |
| gtc agc ctg acc tgt ctg gtg aaa ggc ttc tac ccc agc gac atc gcc<br>Val Ser Leu Thr Cys Leu Val Lys Gly Phe Tyr Pro Ser Asp Ile Ala<br>             595                 600                 605 | 4466 |
| gtg gag tgg gaa agt aac ggc cag cct gag aat aac tac aag act acc<br>Val Glu Trp Glu Ser Asn Gly Gln Pro Glu Asn Asn Tyr Lys Thr Thr<br>610                     615                 620 | 4514 |
| cct cca gtg ctg gat agc gac ggg tcc ttc ttc ctg tat agc aag ctg<br>Pro Pro Val Leu Asp Ser Asp Gly Ser Phe Phe Leu Tyr Ser Lys Leu<br>625                     630                 635                 640 | 4562 |
| aca gtg gac aaa tcc cgc tgg cag cag gga aac gtc ttt tcc tgt tct<br>Thr Val Asp Lys Ser Arg Trp Gln Gln Gly Asn Val Phe Ser Cys Ser<br>                   645                 650                 655 | 4610 |
| gtg atg cat gag gcc ctg cac aat cat tac acc cag aag agt ctg tca<br>Val Met His Glu Ala Leu His Asn His Tyr Thr Gln Lys Ser Leu Ser<br>             660                 665                 670 | 4658 |
| ctg agc ccc ggc aaa tgataaaaag cttctcgaga aggaacccgc gctatgacgg<br>Leu Ser Pro Gly Lys<br>             675 | 4713 |
| caataaaaag acagaataaa acccacgggt gttgggtcgt tgttcataa acccgggaag | 4773 |
| cttatcgata aggatcttcc tagagcatgg ctacgtagat aagtagcatg gcgggttaat | 4833 |
| cattaactac aaggaacccc tagtgatgga gttggccact ccctctctgc gcgctcgctc | 4893 |
| gctcactgag gccgggcgac caaaggtcgc ccgacgcccg ggctttgccc gggcggcctc | 4953 |
| agtgagcgag cgagcgcgca gccttaatta acctaattca ctggccgtcg ttttacaacg | 5013 |
| tcgtgactgg gaaaaccctg gcgttaccca acttaatcgc cttgcagcac atccccttt | 5073 |
| cgccagctgg cgtaatagcg aagaggcccg caccgatcgc ccttcccaac agttgcgcag | 5133 |
| cctgaatggc gaatgggacg cgccctgtag cggcgcatta agcgcggcgg gtgtggtggt | 5193 |
| tacgcgcagc gtgaccgcta cacttgccag cgccctagcg cccgctcctt tcgctttctt | 5253 |
| cccttccttt ctcgccacgt tcgccggctt tccccgtcaa gctctaaatc gggggctccc | 5313 |
| tttagggttc cgatttagtg ctttacggca cctcgacccc aaaaaacttg attagggtga | 5373 |
| tggttcacgt agtgggccat cgccctgata gacggttttt cgccctttga cgttggagtc | 5433 |
| cacgttcttt aatagtggac tcttgttcca actggaaca acactcaacc ctatctcggt | 5493 |
| ctattctttt gatttataag ggattttgcc gatttcggcc tattggttaa aaaatgagct | 5553 |
| gatttaacaa aaatttaacg cgaattttaa caaatatta acgcttacaa ttaggtggc | 5613 |
| acttttcggg gaaatgtgcg cggaacccct atttgtttat ttttctaaat acattcaaat | 5673 |
| atgtatccgc tcatgagaca ataaccctga taaatgcttc aataatattg aaaaggaag | 5733 |
| agtatgagta ttcaacattt ccgtgtcgcc cttattccct tttttgcggc attttgcctt | 5793 |
| cctgtttttg ctcacccaga aacgctggtg aaagtaaaag atgctgaaga tcagttgggt | 5853 |
| gcacgagtgg gttacatcga actggatctc aacagcggta agatccttga gttttcgc | 5913 |
| cccgaagaac gttttccaat gatgagcact tttaaagttc tgctatgtgg cgcggtatta | 5973 |
| tcccgtattg acgccgggca agagcaactc ggtcgccgca tacactattc tcagaatgac | 6033 |

| ttggttgagt actcaccagt cacagaaaag catcttacgg atggcatgac agtaagagaa | 6093 |
| ttatgcagtg ctgccataac catgagtgat aacactgcgg ccaacttact tctgacaacg | 6153 |
| atcggaggac cgaaggagct aaccgctttt ttgcacaaca tggggatca tgtaactcgc | 6213 |
| cttgatcgtt gggaaccgga gctgaatgaa gccataccaa acgacgagcg tgacaccacg | 6273 |
| atgcctgtag caatggcaac aacgttgcgc aaactattaa ctggcgaact acttactcta | 6333 |
| gcttcccggc aacaattaat agactggatg gaggcggata agttgcagg accacttctg | 6393 |
| cgctcggccc ttccggctgg ctggtttatt gctgataaat ctggagccgg tgagcgtggg | 6453 |
| tctcgcggta tcattgcagc actggggcca gatggtaagc cctcccgtat cgtagttatc | 6513 |
| tacacgacgg ggagtcaggc aactatggat gaacgaaata gacagatcgc tgagataggt | 6573 |
| gcctcactga ttaagcattg gtaactgtca gaccaagttt actcatatat actttagatt | 6633 |
| gatttaaaac ttcatttta atttaaaagg atctaggtga agatcctttt tgataatctc | 6693 |
| atgaccaaaa tcccttaacg tgagttttcg ttccactgag cgtcagaccc cgtagaaaag | 6753 |
| atcaaaggat cttcttgaga tccttttttt ctgcgcgtaa tctgctgctt gcaaacaaaa | 6813 |
| aaaccaccgc taccagcggt ggtttgtttg ccggatcaag agctaccaac tcttttccg | 6873 |
| aaggtaactg gcttcagcag agcgcagata ccaaatactg ttcttctagt gtagccgtag | 6933 |
| ttaggccacc acttcaagaa ctctgtagca ccgcctacat acctcgctct gctaatcctg | 6993 |
| ttaccagtgg ctgctgccag tggcgataag tcgtgtctta ccgggttgga ctcaagacga | 7053 |
| tagttaccgg ataaggcgca gcggtcgggc tgaacggggg gttcgtgcac acagcccagc | 7113 |
| ttggagcgaa cgacctacac cgaactgaga tacctacagc gtgagctatg agaaagcgcc | 7173 |
| acgcttcccg aagggagaaa ggcggacagg tatccggtaa gcggcagggt cggaacagga | 7233 |
| gagcgcacga gggagcttcc agggggaaac gcctggtatc tttatagtcc tgtcgggttt | 7293 |
| cgccacctct gacttgagcg tcgatttttg tgatgctcgt cagggggggcg gagcctatgg | 7353 |
| aaaaacgcca gcaacgcggc cttttttacgg ttcctggcct tttgctggcc ttttgctcac | 7413 |
| atgttctttc ctgcgttatc ccctgattct gtggataacc gtattaccgc ctttgagtga | 7473 |
| gctgataccg ctcgccgcag ccgaacgacc gagcgcagcg agtcagtgag cgaggaagcg | 7533 |
| gaagagcgcc caatacgcaa accgcctctc cccgcgcgtt ggccgattca ttaatgcagc | 7593 |
| tggcacgaca ggtttcccga ctggaaagcg ggcagtgagc gcaacgcaat taatgtgagt | 7653 |
| tagctcactc attaggcacc ccaggcttta cactttatgc ttccggctcg tatgttgtgt | 7713 |
| ggaattgtga gcggataaca atttcacaca ggaaacagct atgaccatga ttacgccaga | 7773 |
| tttaattaa | 7782 |

<210> SEQ ID NO 31
<211> LENGTH: 120
<212> TYPE: PRT
<213> ORGANISM: Artificial
<220> FEATURE:
<223> OTHER INFORMATION: Synthetic Construct

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Asn Tyr
            20                  25                  30

Tyr Trp Ser Trp Ile Arg Gln Ser Pro Gly Lys Gly Leu Glu Trp Ile
        35                  40                  45

```
Gly Phe Ile Tyr Tyr Gly Gly Asn Thr Lys Tyr Asn Pro Ser Leu Lys
         50                  55                  60

Ser Arg Val Thr Ile Ser Gln Asp Thr Ser Lys Ser Gln Val Ser Leu
 65                  70                  75                  80

Thr Met Ser Ser Val Thr Ala Ala Glu Ser Ala Val Tyr Phe Cys Ala
                 85                  90                  95

Arg Ala Ser Cys Ser Gly Gly Tyr Cys Ile Leu Asp Tyr Trp Gly Gln
                100                 105                 110

Gly Thr Leu Val Thr Val Ser Ser
            115                 120

<210> SEQ ID NO 32
<211> LENGTH: 98
<212> TYPE: PRT
<213> ORGANISM: Artificial
<220> FEATURE:
<223> OTHER INFORMATION: Synthetic Construct

<400> SEQUENCE: 32

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val

<210> SEQ ID NO 33
<211> LENGTH: 129
<212> TYPE: PRT
<213> ORGANISM: Artificial
<220> FEATURE:
<223> OTHER INFORMATION: Synthetic Construct

<400> SEQUENCE: 33

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Thr Tyr
                 20                  25                  30

Ala Met His Trp Val Arg Gln Ala Pro Gly Lys Gly Leu Glu Trp Val
             35                  40                  45

Ala Val Ile Ser Tyr Asp Ala Asn Tyr Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Gln Leu Arg Ser Leu Leu Tyr Phe Glu Trp Leu Ser
                100                 105                 110
```

```
Gln Gly Tyr Phe Asp Tyr Trp Gly Gln Gly Thr Leu Val Thr Val Ser
            115                 120                 125

Ser

<210> SEQ ID NO 34
<211> LENGTH: 107
<212> TYPE: PRT
<213> ORGANISM: Artificial
<220> FEATURE:
<223> OTHER INFORMATION: Synthetic Construct

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105

<210> SEQ ID NO 35
<211> LENGTH: 223
<212> TYPE: PRT
<213> ORGANISM: Artificial
<220> FEATURE:
<223> OTHER INFORMATION: Synthetic Construct

<400> SEQUENCE: 35

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175
```

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 36
<211> LENGTH: 7814
<212> TYPE: DNA
<213> ORGANISM: Artificial sequence
<220> FEATURE:
<223> OTHER INFORMATION: FI6 and CO5 immunoadhesins
<220> FEATURE:
<221> NAME/KEY: polyA_signal
<222> LOCATION: (201)..(432)
<223> OTHER INFORMATION: complement - SV40\polyA
<220> FEATURE:
<221> NAME/KEY: misc_feature
<222> LOCATION: (453)..(1121)
<223> OTHER INFORMATION: complement - CH'2-3
<220> FEATURE:
<221> NAME/KEY: misc_feature
<222> LOCATION: (1125)..(1457)
<223> OTHER INFORMATION: complement - C05\VL
<220> FEATURE:
<221> NAME/KEY: misc_feature
<222> LOCATION: (1458)..(1502)
<223> OTHER INFORMATION: SL\from\3bn201co
<220> FEATURE:
<221> NAME/KEY: misc_feature
<222> LOCATION: (1503)..(1916)
<223> OTHER INFORMATION: complement - C05\VH
<220> FEATURE:
<221> NAME/KEY: misc_feature
<222> LOCATION: (1965)..(1973)
<223> OTHER INFORMATION: leader
<220> FEATURE:
<221> NAME/KEY: misc_feature
<222> LOCATION: (2371)..(2412)
<223> OTHER INFORMATION: complement - CMV\mp2
<220> FEATURE:
<221> NAME/KEY: misc_feature
<222> LOCATION: (2413)..(2881)
<223> OTHER INFORMATION: enhancer
<220> FEATURE:
<221> NAME/KEY: misc_feature
<222> LOCATION: (2882)..(3007)
<223> OTHER INFORMATION: CMV\mp1
<220> FEATURE:
<221> NAME/KEY: misc_feature
<222> LOCATION: (3067)..(3055)
<223> OTHER INFORMATION: leader
<220> FEATURE:
<221> NAME/KEY: CDS
<222> LOCATION: (3124)..(3510)
<223> OTHER INFORMATION: FI6\VH
<220> FEATURE:
<221> NAME/KEY: misc_feature
<222> LOCATION: (3511)..(3555)
<223> OTHER INFORMATION: SL\from\3bn201co
<220> FEATURE:
<221> NAME/KEY: CDS
<222> LOCATION: (3556)..(3888)
<223> OTHER INFORMATION: FI6\VL
<220> FEATURE:
<221> NAME/KEY: CDS
<222> LOCATION: (3892)..(4560)
<223> OTHER INFORMATION: CH2-3
<220> FEATURE:
<221> NAME/KEY: polyA_signal
<222> LOCATION: (4581)..(4812)
<223> OTHER INFORMATION: SV40\polyA

```
<400> SEQUENCE: 36
ggccttaatt aggctgcgcg ctcgctcgct cactgaggcc gcccgggcaa agcccgggcg     60
tcgggcgacc tttggtcgcc cggcctcagt gagcgagcga gcgcgcagag agggagtggc    120
caactccatc actaggggtt ccttgtagtt aatgattaac cgccatgct acttatctac     180
gtagccatgc tctaggaaga tcattttacc acatttgtag aggttttact tgctttaaaa    240
aacctcccac atctccccct gaacctgaaa cataaaatga atgcaattgt tgttgttaac    300
ttgtttattg cagcttataa tggttacaaa taaagcaata gcatcacaaa tttcacaaat    360
aaagcatttt tttcactgca ttctagttgt ggtttgtcca aactcatcaa tgtatcttat    420
catgtctgct cgaagcggcc gcaagcttat cacttcccgg ggctcaggct cagggacttc    480
tgggtgtagt ggttgtgcag ggcctcgtgc atcacgctgc agctgaacac gttgccctgc    540
tgccaccggc tcttgtccac ggtcagcttg ctatacagga agaatgagcc gtcgctgtcc    600
agcacagggg gggtggtctt gtagttgttc tcgggctggc cgttgctctc ccattccacg    660
gcgatctcgc tggggtagaa gcccttgacc aggcaggtca gggacacctg gttcttggtc    720
atctcttccc ggctgggggg cagtgtgtag acctgaggct cgcggggctg gcccttggcc    780
ttgctgatgg ttttctcgat gggggcaggc agggccttgt tggacacctt gcacttgtac    840
tctttgccgt tcagccagtc ctggtgcagc acggtcagca cggacaccac ccggtaggtg    900
ctgttgtact gttcctctct gggcttggtc ttggcgttgt gcacttccac gccgtccacg    960
taccaattga acttcacttc agggtcctcg tgggacacgt ccaccaccac gcaggtcact   1020
tcggggtcc ggctgatcat cagggtgtcc ttgggctttg gggggaacag gaacacgctg    1080
gggcctccca gcagttcagg ggcagggcag gggggacacg tggctagcac cgtacgcttg   1140
atctccagct tggttcctcc tccgaaggtg aatggcagtc catcgtactg ctggcagtag   1200
taggttccca catccttcag gctgcaggcc acgctgctgc tcaggctgat ctgtcccaga   1260
tccactccgt gaaccggct tggcactccc cgctgcaggt tgctggcatc gtagatcagc    1320
agctttggtc cctttcctgg cttctgctgg taccagttca ggaacttcct gatgtcctgg   1380
ctggcctggc aggtcagggt cacccgatct cccacgctgg cgctcaggct gcttgggctc   1440
tgggtcagct ggatatcaga tcccccgcct ccggaccctc ctcctccgct gcctcctccg   1500
ccgctcgaga cggtcaccag ggttccctgt ccccacacat cgaaggcatc tcccaccaga   1560
tcggcccgct cccatccggc gctcaccacc tgctgcatgg acatgtgctt ggcgcagtag   1620
tacactccgg tatcctccac ccgcaggttg gtcatctgca ggtacagggt ctccttgctg   1680
ttatcccggc tgatggtgaa ccgtccctcc acgctatcgg cgtaatcaat gtctcctcct   1740
ccggcgttga tgatgctcag ccactccagt cccttcctg gggcctgccg cacccagctc    1800
acggcgtagt agctcagggt gctctctccg aagctgcttc cgcttccac gcagctcagc    1860
cgcaggctct ctcctggctg caccagtcct cctccgctct cctgcagctg cacctgtgaa   1920
ttcgtcacca gggccaggct cagggcgatc agcagcagca gctgcatgcg catggtgggg   1980
cggcagagtc gcgtccttgc tcgggtgttg taagttccag tgcaaagtgc cctagcctat   2040
agtgagtcgt attaagtact ctagccttaa gagctgtaat tgaactggga gtggacacct   2100
gtggagagaa aggcaaagtg gatgtcagta agaccaatag gtgcctatca gaaacgcaag   2160
agtcttctct gtctcgacaa gcccagtttc tattggtctc cttaaacctg tcttgtaacc   2220
ttgatactta cctgcccagt gcctcacgac caacttctgc agcttaagtt cgagactgtt   2280
gtgtcagaag cactgactgc gttagcaatt taactgtgat aaactaccgc ataaagctt    2340
```

```
ctagtgatct gacggttcac taaacgagct ctgcttatat aggcctccca ccgtacacgc    2400
cacctcgaca tacctagtta ttaatagtaa tcaattacgg ggtcattagt tcatagccca    2460
tatatggagt tccgcgttac ataacttacg gtaaatggcc cgcctggctg accgcccaac    2520
gaccccgcc cattgacgtc aataatgacg tatgttccca tagtaacgcc aatagggact    2580
ttccattgac gtcaatgggt ggagtattta cggtaaactg cccacttggc agtacatcaa    2640
gtgtatcata tgccaagtac gccccctatt gacgtcaatg acggtaaatg gcccgcctgg    2700
cattatgccc agtacatgac cttatgggac tttcctactt ggcagtacat ctacgtatta    2760
gtcatcgcta ttaccatggt gatgcggttt tggcagtaca tcaatgggcg tggatagcgg    2820
tttgactcac ggggatttcc aagtctccac cccattgacg tcaatgggag tttgttttgg    2880
caccaaaatc aacgggactt tccaaaatgt cgtaacaact ccgccccatt gacgcaaatg    2940
ggcggtaggc gtgtacggtg ggaggtctat ataagcagag ctggtttagt gaaccgtcag    3000
atccgctggg cactttgcac tggaacttac aacacccgag caaggacgcg actctgccgc    3060
cccaccatgc gcatgcagct gctgctgctg atcgccctga gcctggccct ggtgaccaac    3120
```

| | | | | | | | | | | | | | | | | |
|---|---|---|---|---|---|---|---|---|---|---|---|---|---|---|---|---|
| agc | cag | gtg | caa | ttg | gtg | gag | agc | gga | gga | gga | gtg | gtg | cag | cca | gga | 3168 |
| Gln | Val | Gln | Leu | Val | Glu | Ser | Gly | Gly | Gly | Val | Val | Gln | Pro | Gly | | |
| 1 | | | | 5 | | | | | 10 | | | | | 15 | | |

```
cgg agc ctg cgg ctg agc tgc gcc gcc agc gga ttc acc ttc agc acc    3216
Arg Ser Leu Arg Leu Ser Cys Ala Ala Ser Gly Phe Thr Phe Ser Thr
            20                      25                      30 tac gcc atg cac tgg gtg cgg cag gcc cca gga aag gga ctg gag tgg    3264
Tyr Ala Met His Trp Val Arg Gln Ala Pro Gly Lys Gly Leu Glu Trp
        35                      40                      45 gtg gcc gtg atc agc tac gat gcc aac tac aag tac tac gcc gat agc    3312
Val Ala Val Ile Ser Tyr Asp Ala Asn Tyr Lys Tyr Tyr Ala Asp Ser
    50                      55                      60 gtg aag gga cgg ttc acc atc agc cgg gat aac agc aag aac acc ctg    3360
Val Lys Gly Arg Phe Thr Ile Ser Arg Asp Asn Ser Lys Asn Thr Leu
65                      70                      75 tac ctg cag atg aac agc ctg cgg gcc gag gat acc gcc gtg tac tac    3408
Tyr Leu Gln Met Asn Ser Leu Arg Ala Glu Asp Thr Ala Val Tyr Tyr
80                      85                      90                      95 tgc gcc aag gat agc cag ctg cgg agc ctg ctg tac ttc gag tgg ctg    3456
Cys Ala Lys Asp Ser Gln Leu Arg Ser Leu Leu Tyr Phe Glu Trp Leu
                100                     105                     110 agc cag gga tac ttc gat tac tgg gga cag gga acc ctg gtg acc gtg    3504
Ser Gln Gly Tyr Phe Asp Tyr Trp Gly Gln Gly Thr Leu Val Thr Val
            115                     120                     125 agc agc ggcggaggag gcagcggagg aggagggtcc ggaggcgggg gatct gat atc    3561
Ser Ser                                                    Asp Ile
                                                           130 gtc atg acc cag agc cca gat agc ctg gcc gtg agc ctg gga gag cgg    3609
Val Met Thr Gln Ser Pro Asp Ser Leu Ala Val Ser Leu Gly Glu Arg
        135                     140                     145 gcc acc atc aac tgc aag agc agc cag agc gtg acc ttc aac tac aag    3657
Ala Thr Ile Asn Cys Lys Ser Ser Gln Ser Val Thr Phe Asn Tyr Lys
    150                     155                     160 aac tac ctg gcc tgg tac cag cag aag cca gga cag cca cca aag ctg    3705
Asn Tyr Leu Ala Trp Tyr Gln Gln Lys Pro Gly Gln Pro Pro Lys Leu
165                     170                     175 ctg atc tac tgg gcc agc acc cgg gag agc gga gtg cca gat cgg ttc    3753
Leu Ile Tyr Trp Ala Ser Thr Arg Glu Ser Gly Val Pro Asp Arg Phe
180                     185                     190                     195
```

| | | |
|---|---|---|
| agc gga agc gga agc gga acc gat ttc acc ctg acc atc agc agc ctg<br>Ser Gly Ser Gly Ser Gly Thr Asp Phe Thr Leu Thr Ile Ser Ser Leu<br>200 205 210 | | 3801 |
| cag gcc gag gat gtg gcc gtg tac tac tgc cag cag cac tac cgg acc<br>Gln Ala Glu Asp Val Ala Val Tyr Tyr Cys Gln Gln His Tyr Arg Thr<br>215 220 225 | | 3849 |
| cca cca acc ttc gga cag gga acc aag gtg gag atc aag gcc acg tgc<br>Pro Pro Thr Phe Gly Gln Gly Thr Lys Val Glu Ile Lys Thr Cys<br>230 235 240 | | 3897 |
| cct cca tgt cca gcc ccc gaa ctg ctg ggg ggg cct agc gtg ttc ctg<br>Pro Pro Cys Pro Ala Pro Glu Leu Leu Gly Gly Pro Ser Val Phe Leu<br>245 250 255 | | 3945 |
| ttt ccc cct aag cct aaa gat aca ctg atg att agt aga acc cca gag<br>Phe Pro Pro Lys Pro Lys Asp Thr Leu Met Ile Ser Arg Thr Pro Glu<br>260 265 270 | | 3993 |
| gtc aca tgc gtg gtc gtg gac gtg tcc cac gaa gag cct gac gtg aag<br>Val Thr Cys Val Val Val Asp Val Ser His Glu Glu Pro Asp Val Lys<br>275 280 285 290 | | 4041 |
| ttc aac tgg tac gtg gat ggc gtg gag gtg cac aat gct aag act aaa<br>Phe Asn Trp Tyr Val Asp Gly Val Glu Val His Asn Ala Lys Thr Lys<br>295 300 305 | | 4089 |
| cca cgc gaa gag cag tat aat agt aca tac cga gtc gtg tca gtc ctg<br>Pro Arg Glu Glu Gln Tyr Asn Ser Thr Tyr Arg Val Val Ser Val Leu<br>310 315 320 | | 4137 |
| aca gtg ctg cac cag gat tgg ctg aac ggc aag gag tat aag tgc aag<br>Thr Val Leu His Gln Asp Trp Leu Asn Gly Lys Glu Tyr Lys Cys Lys<br>325 330 335 | | 4185 |
| gtg tct aac aag gcc ctg ccc gcc cct atc gag aaa aca att agc aag<br>Val Ser Asn Lys Ala Leu Pro Ala Pro Ile Glu Lys Thr Ile Ser Lys<br>340 345 350 | | 4233 |
| gcc aaa ggg cag cca cgg gaa ccc cag gtc tac act ctg cca ccc tca<br>Ala Lys Gly Gln Pro Arg Glu Pro Gln Val Tyr Thr Leu Pro Pro Ser<br>355 360 365 370 | | 4281 |
| aga gat gaa ctg act aag aac cag gtc agc ctg acc tgt ctg gtg aaa<br>Arg Asp Glu Leu Thr Lys Asn Gln Val Ser Leu Thr Cys Leu Val Lys<br>375 380 385 | | 4329 |
| ggc ttc tac ccc agc gac atc gcc gtg gag tgg gaa agt aac ggc cag<br>Gly Phe Tyr Pro Ser Asp Ile Ala Val Glu Trp Glu Ser Asn Gly Gln<br>390 395 400 | | 4377 |
| cct gag aat aac tac aag act acc cct cca gtg ctg gat agc gac ggg<br>Pro Glu Asn Asn Tyr Lys Thr Thr Pro Pro Val Leu Asp Ser Asp Gly<br>405 410 415 | | 4425 |
| tcc ttc ttc ctg tat agc aag ctg aca gtg gac aaa tcc cgc tgg cag<br>Ser Phe Phe Leu Tyr Ser Lys Leu Thr Val Asp Lys Ser Arg Trp Gln<br>420 425 430 | | 4473 |
| cag gga aac gtc ttt tcc tgt tct gtg atg cat gag gcc ctg cac aat<br>Gln Gly Asn Val Phe Ser Cys Ser Val Met His Glu Ala Leu His Asn<br>435 440 445 450 | | 4521 |
| cat tac acc cag aag agt ctg tca ctg agc ccc ggc aaa tgataagctt<br>His Tyr Thr Gln Lys Ser Leu Ser Leu Ser Pro Gly Lys<br>455 460 | | 4570 |
| gcggccgctt cgagcagaca tgataagata cattgatgag tttggacaaa ccacaactag | | 4630 |
| aatgcagtga aaaaaatgct ttatttgtga aatttgtgat gctattgctt tatttgtaac | | 4690 |
| cattataagc tgcaataaac aagttaacaa caacaattgc attcatttta tgtttcaggt | | 4750 |
| tcagggggag atgtgggagg ttttttaaag caagtaaaac ctctacaaat gtggtaaaat | | 4810 |
| cgataaggat cttcctagag catggctacg tagataagta gcatggcggg ttaatcatta | | 4870 |
| actacaagga accccctagtg atggagttgg ccactccctc tctgcgcgct cgctcgctca | | 4930 |

```
ctgaggccgg gcgaccaaag gtcgcccgac gcccgggctt tgcccgggcg gcctcagtga   4990
gcgagcgagc gcgcagcctt aattaaccta attcactggc cgtcgtttta caacgtcgtg   5050
actgggaaaa ccctggcgtt acccaactta atcgccttgc agcacatccc cctttcgcca   5110
gctgcgtaa tagcgaagag gcccgcaccg atcgcccttc ccaacagttg cgcagcctga   5170
atggcgaatg ggacgcgccc tgtagcggcg cattaagcgc ggcgggtgtg gtggttacgc   5230
gcagcgtgac cgctcacttt gccagcgccc tagcgcccgc tcctttcgct ttcttccctt   5290
cctttctcgc cacgttcgcc ggctttcccc gtcaagctct aaatcggggg ctcccttag    5350
ggttccgatt tagtgcttta cggcacctcg accccaaaaa acttgattag ggtgatggtt   5410
cacgtagtgg gccatcgccc tgatagacgg ttttcgccc tttgacgttg gagtccacgt    5470
tctttaatag tggactcttg ttccaaactg gaacaacact caaccctatc tcggtctatt   5530
cttttgattt ataagggatt tgccgatttc ggcctattg gttaaaaaat gagctgattt     5590
aacaaaaatt taacgcgaat tttaacaaaa tattaacgct tacaatttag gtggcacttt    5650
tcggggaaat gtgcgcggaa cccctatttg tttatttttc taaatacatt caaatatgta    5710
tccgctcatg agacaataac cctgataaat gcttcaataa tattgaaaaa ggaagagtat    5770
gagtattcaa catttccgtg tcgcccttat ccctttttt gcggcatttt gccttcctgt     5830
ttttgctcac ccagaaacgc tggtgaaagt aaaagatgct gaagatcagt tgggtgcacg    5890
agtgggttac atcgaactgg atctcaacag cggtaagatc cttgagagtt ttcgccccga    5950
agaacgtttt ccaatgatga gcacttttaa agttctgcta tgtggcgcgg tattatcccg    6010
tattgacgcc gggcaagagc aactcggtcg ccgcatacac tattctcaga atgacttggt    6070
tgagtactca ccagtcacag aaaagcatct tacggatggc atgacagtaa gagaattatg    6130
cagtgctgcc ataaccatga gtgataacac tgcggccaac ttacttctga caacgatcgg    6190
aggaccgaag gagctaaccg cttttttgca acatggggg atcatgtaa ctcgccttga     6250
tcgttgggaa ccggagctga atgaagccat accaaacgac gagcgtgaca ccacgatgcc    6310
tgtagcaatg gcaacaacgt tgcgcaaact attaactggc gaactactta ctctagcttc    6370
ccggcaacaa ttaatagact ggatggaggc ggataaagtt gcaggaccac ttctgcgctc    6430
ggcccttccg gctggctggt ttattgctga taaatctgga gccggtgagc gtgggtctcg    6490
cggtatcatt gcagcactgg ggccagatgg taagccctcc cgtatcgtag ttatctacac    6550
gacggggagt caggcaacta tggatgaacg aaatagacag atcgctgaga taggtgcctc    6610
actgattaag cattggtaac tgtcagacca agtttactca tatatacttt agattgattt    6670
aaaacttcat ttttaattta aaaggatcta ggtgaagatc ctttttgata atctcatgac    6730
caaaatccct taacgtgagt tttcgttcca ctgagcgtca gaccccgtag aaaagatcaa    6790
aggatcttct tgagatcctt ttttctgcg cgtaatctgc tgcttgcaaa caaaaaaacc    6850
accgctacca gcggtggttt gtttgccgga tcaagagcta ccaactcttt ttccgaaggt    6910
aactggcttc agcagagcgc agataccaaa tactgttctt ctagtgtagc cgtagttagg    6970
ccaccacttc aagaactctg tagcaccgcc tacatacctc gctctgctaa tcctgttacc    7030
agtggctgct gccagtggcg ataagtcgtg tcttaccggg ttggactcaa gacgatagtt    7090
accggataag gcgcagcggt cgggctgaac ggggggttcg tgcacacagc ccagcttgga    7150
gcgaacgacc tacaccgaac tgagatacct acagcgtgag ctatgagaaa gcgccacgct    7210
tcccgaaggg agaaaggcgg acaggtatcc ggtaagcggc agggtcggaa caggagagcg    7270
cacgagggag cttccagggg gaaacgcctg gtatctttat agtcctgtcg gtttcgcca    7330
```

-continued

```
cctctgactt gagcgtcgat ttttgtgatg ctcgtcaggg gggcggagcc tatggaaaaa    7390
cgccagcaac gcggccttt tacggttcct ggccttttgc tggccttttg ctcacatgtt    7450
ctttcctgcg ttatccctg attctgtgga taaccgtatt accgcctttg agtgagctga    7510
taccgctcgc cgcagccgaa cgaccgagcg cagcgagtca gtgagcgagg aagcggaaga    7570
gcgcccaata cgcaaaccgc ctctccccgc gcgttggccg attcattaat gcagctggca    7630
cgacaggttt cccgactgga aagcgggcag tgagcgcaac gcaattaatg tgagttagct    7690
cactcattag gcaccccagg ctttacactt tatgcttccg gctcgtatgt tgtgtggaat    7750
tgtgagcgga taacaatttc acacaggaaa cagctatgac catgattacg ccagatttaa    7810
ttaa                                                                 7814
```

<210> SEQ ID NO 37
<211> LENGTH: 129
<212> TYPE: PRT
<213> ORGANISM: Artificial sequence
<220> FEATURE:
<223> OTHER INFORMATION: Synthetic Construct

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 38
<211> LENGTH: 111
<212> TYPE: PRT
<213> ORGANISM: Artificial sequence
<220> FEATURE:
<223> OTHER INFORMATION: Synthetic Construct

<400> SEQUENCE: 38

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
            85                  90                  95

Arg Thr Pro Pro Thr Phe Gly Gln Gly Thr Lys Val Glu Ile Lys
            100                 105                 110

<210> SEQ ID NO 39
<211> LENGTH: 223
<212> TYPE: PRT
<213> ORGANISM: Artificial sequence
<220> FEATURE:
<223> OTHER INFORMATION: Synthetic Construct

<400> SEQUENCE: 39

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
            85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
            115                 120                 125

Pro Ser Arg Asp Glu Leu Thr Lys Asn Gln Val Ser Leu Thr Cys Leu
        130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
            165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 40
<211> LENGTH: 7784
<212> TYPE: DNA
<213> ORGANISM: Artificial sequence
<220> FEATURE:
<223> OTHER INFORMATION: FI6 and CR8033 immunoadhesins
<220> FEATURE:
<221> NAME/KEY: polyA_signal
<222> LOCATION: (201)..(432)
<223> OTHER INFORMATION: complement - SV40\polyA
<220> FEATURE:
<221> NAME/KEY: misc_feature
<222> LOCATION: (453)..(1121)
<223> OTHER INFORMATION: complement - CH'2-3
<220> FEATURE:
<221> NAME/KEY: misc_feature
<222> LOCATION: (1125)..(1460)
<223> OTHER INFORMATION: complement - 033\VL

```
<220> FEATURE:
<221> NAME/KEY: misc_feature
<222> LOCATION: (1461)..(1505)
<223> OTHER INFORMATION: SL\from\3bn201co
<220> FEATURE:
<221> NAME/KEY: misc_feature
<222> LOCATION: (1506)..(1886)
<223> OTHER INFORMATION: complement - 033\VH
<220> FEATURE:
<221> NAME/KEY: misc_feature
<222> LOCATION: (1935)..(1946)
<223> OTHER INFORMATION: complement - leader
<220> FEATURE:
<221> NAME/KEY: misc_feature
<222> LOCATION: (2341)..(2382)
<223> OTHER INFORMATION: complement - CMV\mp2
<220> FEATURE:
<221> NAME/KEY: misc_feature
<222> LOCATION: (2383)..(2851)
<223> OTHER INFORMATION: enhancer
<220> FEATURE:
<221> NAME/KEY: misc_feature
<222> LOCATION: (2852)..(2977)
<223> OTHER INFORMATION: CMV\mp1
<220> FEATURE:
<221> NAME/KEY: misc_feature
<222> LOCATION: (3073)..(3045)
<223> OTHER INFORMATION: leader
<220> FEATURE:
<221> NAME/KEY: CDS
<222> LOCATION: (3094)..(3480)
<223> OTHER INFORMATION: FI6\VH
<220> FEATURE:
<221> NAME/KEY: misc_feature
<222> LOCATION: (3481)..(3525)
<223> OTHER INFORMATION: SL\from\3bn201co
<220> FEATURE:
<221> NAME/KEY: CDS
<222> LOCATION: (3526)..(3858)
<223> OTHER INFORMATION: FI6\VL
<220> FEATURE:
<221> NAME/KEY: misc_feature
<222> LOCATION: (3862)..(4530)
<223> OTHER INFORMATION: CH2-3
<220> FEATURE:
<221> NAME/KEY: polyA_signal
<222> LOCATION: (4551)..(4782)
<223> OTHER INFORMATION: SV40\polyA

<400> SEQUENCE: 40
ggccttaatt aggctgcgcg ctcgctcgct cactgaggcc gcccgggcaa agcccgggcg      60
tcgggcgacc tttggtcgcc cggcctcagt gagcgagcga gcgcgcagag agggagtggc     120
caactccatc actaggggtt ccttgtagtt aatgattaac ccgccatgct acttatctac     180
gtagccatgc tctaggaaga tcattttacc acatttgtag aggttttact tgctttaaaa     240
aacctcccac atctcccccct gaacctgaaa cataaaatga atgcaattgt tgttgttaac    300
ttgtttattg cagcttataa tggttacaaa taaagcaata gcatcacaaa tttcacaaat    360
aaagcatttt tttcactgca ttctagttgt ggtttgtcca aactcatcaa tgtatcttat    420
catgtctgct cgaagcggcc gcaagcttat cacttcccgg ggctcaggct cagggacttc    480
tgggtgtagt ggttgtgcag ggcctcgtgc atcacgctgc agctgaacac gttgccctgc    540
tgccaccggc tcttgtccac ggtcagcttg ctatacagga agaatgagcc gtcgctgtcc    600
agcacagggg gggtggtctt gtagttgttc tcgggctggc cgttgctctc ccattccacg    660
gcgatctcgc tggggtagaa gcccttgacc aggcaggtca gggacacctg gttcttggtc    720
atctcttccc ggctgggggg cagtgtgtag acctgaggct cgcggggctg gcccttggcc    780
ttgctgatgg ttttctcgat gggggcaggc agggccttgt tggacaccct gcacttgtac    840
```

| | |
|---|---|
| tctttgccgt tcagccagtc ctggtgcagc acggtcagca cggacaccac ccggtaggtg | 900 |
| ctgttgtact gttcctctct gggcttggtc ttggcgttgt gcacttccac gccgtccacg | 960 |
| taccaattga acttcacttc agggtcctcg tgggacacgt ccaccaccac gcaggtcact | 1020 |
| tcggggtcc ggctgatcat cagggtgtcc ttgggctttg gggggaacag gaacacgctg | 1080 |
| gggcctccca gcagttcagg ggcagggcag ggggacacg tggctagcac cgtacgcttg | 1140 |
| atctccacct tggttccctg tccgaaggtc caagggctgc ttccgtactg ctggcagtag | 1200 |
| tacacggcca gatcctctgg ctccagccgg ctgatggtca gggtgaaatc ggttccgctt | 1260 |
| ccgcttccgc tgaaccgggc tgggattccg gtggcccggg tgctggctcc gtagatcagc | 1320 |
| agccgtgggg cctgtcctgg cttctgctgg taccaggcca ggtagctgct gctcacgctc | 1380 |
| tggctggccc ggcagctcag ggtggcccgc tctcctgggc tcaggctcag ggttcctggg | 1440 |
| ctctgggtca gcacgatctc agatccccg cctccggacc tcctcctcc gctgcctcct | 1500 |
| ccgccgctgc tcacggtcac catggttccc tgtcccaga tatcgaaggt tcctccctcc | 1560 |
| aggatatcca tggcgctgct ctccagccga tccttggcgc agtagtacag ggcggtatcc | 1620 |
| tcggcccgca ggctgttcat ctgcaggtac aggctgttct ttccgttatc ccggctgatg | 1680 |
| gtgaaccgtc cctgcacgct atcggcgtat cccatgaagt ttcccttcca gttgattccg | 1740 |
| gccacccact ccagtcccct tcctggggcc tgccgcaccc agtgcatggt gtactcatcg | 1800 |
| aagctgaatc cgctggcggc gcagctcagc cgcaggctcc gtcctggctg caccagtcct | 1860 |
| cctccggtct ccaccagctg cacctctgaa ttcgtcacca gggccaggct cagggcgatc | 1920 |
| agcagcagca gctgcatgcg catggtgggg cggcagagtc gcgtccttgc tcgggtgttg | 1980 |
| taagttccag tgcaaagtgc cctagcctat agtgagtcgt attaagtact ctagccttaa | 2040 |
| gagctgtaat tgaactggga gtggacacct gtggagagaa aggcaaagtg gatgtcagta | 2100 |
| agaccaatag gtgcctatca gaaacgcaag agtcttctct gtctcgacaa gcccagtttc | 2160 |
| tattggtctc cttaaacctg tcttgtaacc ttgatactta cctgcccagt gcctcacgac | 2220 |
| caacttctgc agcttaagtt cgagactgtt gtgtcagaag cactgactgc gttagcaatt | 2280 |
| taactgtgat aaactaccgc aataaagctt ctagtgatct gacggttcac taaacgagct | 2340 |
| ctgcttatat aggcctccca ccgtacacgc cacctcgaca tacctagtta ttaatagtaa | 2400 |
| tcaattacgg ggtcattagt tcatagccca tatatggagt tccgcgttac ataacttacg | 2460 |
| gtaaatggcc cgcctggctg accgcccaac gacccccgcc cattgacgtc aataatgacg | 2520 |
| tatgttccca tagtaacgcc aatagggact ttccattgac gtcaatgggt ggagtattta | 2580 |
| cggtaaactg cccacttggc agtacatcaa gtgtatcata tgccaagtac gccccctatt | 2640 |
| gacgtcaatg acggtaaatg gcccgcctgg cattatgccc agtacatgac cttatgggac | 2700 |
| tttcctactt ggcagtacat ctacgtatta gtcatcgcta ttaccatggt gatgcggttt | 2760 |
| tggcagtaca tcaatgggcg tggatagcgg tttgactcac ggggatttcc aagtctccac | 2820 |
| cccattgacg tcaatgggag tttgttttgg caccaaaatc aacgggactt tccaaaatgt | 2880 |
| cgtaacaact ccgccccatt gacgcaaatg ggcggtaggc gtgtacggtg ggaggtctat | 2940 |
| ataagcagag ctggtttagt gaaccgtcag atccgctggg cactttgcac tggaacttac | 3000 |
| aacacccgag caaggacgcg actctgccgc cccaccatgc gcatgcagct gctgctgctg | 3060 |
| atcgccctga gcctggccct ggtgaccaac agc cag gtg caa ttg gtg gag agc | 3114 |
|                                                                                 Gln Val Gln Leu Val Glu Ser<br>                                                                                  1               5 | |

| | | |
|---|---|---|
| gga gga gga gtg gtg cag cca gga cgg agc ctg cgg ctg agc tgc gcc<br>Gly Gly Gly Val Val Gln Pro Gly Arg Ser Leu Arg Leu Ser Cys Ala<br>　　　10　　　　　　　　15　　　　　　　　20 | | 3162 |
| gcc agc gga ttc acc ttc agc acc tac gcc atg cac tgg gtg cgg cag<br>Ala Ser Gly Phe Thr Phe Ser Thr Tyr Ala Met His Trp Val Arg Gln<br>25　　　　　　　　30　　　　　　　　35 | | 3210 |
| gcc cca gga aag gga ctg gag tgg gtg gcc gtg atc agc tac gat gcc<br>Ala Pro Gly Lys Gly Leu Glu Trp Val Ala Val Ile Ser Tyr Asp Ala<br>40　　　　　　　　45　　　　　　　　50　　　　　　　　55 | | 3258 |
| aac tac aag tac tac gcc gat agc gtg aag gga cgg ttc acc atc agc<br>Asn Tyr Lys Tyr Tyr Ala Asp Ser Val Lys Gly Arg Phe Thr Ile Ser<br>　　　60　　　　　　　　65　　　　　　　　70 | | 3306 |
| cgg gat aac agc aag aac acc ctg tac ctg cag atg aac agc ctg cgg<br>Arg Asp Asn Ser Lys Asn Thr Leu Tyr Leu Gln Met Asn Ser Leu Arg<br>75　　　　　　　　80　　　　　　　　85 | | 3354 |
| gcc gag gat acc gcc gtg tac tac tgc gcc aag gat agc cag ctg cgg<br>Ala Glu Asp Thr Ala Val Tyr Tyr Cys Ala Lys Asp Ser Gln Leu Arg<br>90　　　　　　　　95　　　　　　　　100 | | 3402 |
| agc ctg ctg tac ttc gag tgg ctg agc cag gga tac ttc gat tac tgg<br>Ser Leu Leu Tyr Phe Glu Trp Leu Ser Gln Gly Tyr Phe Asp Tyr Trp<br>105　　　　　　　　110　　　　　　　　115 | | 3450 |
| gga cag gga acc ctg gtg acc gtg agc agc ggcggaggag gcagcggagg<br>Gly Gln Gly Thr Leu Val Thr Val Ser Ser<br>120　　　　　　　　125 | | 3500 |
| aggagggtcc ggaggcgggg gatct gat atc gtc atg acc cag agc cca gat<br>　　　　　　　　　　　　　　　Asp Ile Val Met Thr Gln Ser Pro Asp<br>　　　　　　　　　　　　　　　130　　　　　　　　135 | | 3552 |
| agc ctg gcc gtg agc ctg gga gag cgg gcc acc atc aac tgc aag agc<br>Ser Leu Ala Val Ser Leu Gly Glu Arg Ala Thr Ile Asn Cys Lys Ser<br>140　　　　　　　　145　　　　　　　　150 | | 3600 |
| agc cag agc gtg acc ttc aac tac aag aac tac ctg gcc tgg tac cag<br>Ser Gln Ser Val Thr Phe Asn Tyr Lys Asn Tyr Leu Ala Trp Tyr Gln<br>155　　　　　　　　160　　　　　　　　165　　　　　　　　170 | | 3648 |
| cag aag cca gga cag cca cca aag ctg ctg atc tac tgg gcc agc acc<br>Gln Lys Pro Gly Gln Pro Pro Lys Leu Leu Ile Tyr Trp Ala Ser Thr<br>　　　175　　　　　　　　180　　　　　　　　185 | | 3696 |
| cgg gag agc gga gtg cca gat cgg ttc agc gga agc gga agc gga acc<br>Arg Glu Ser Gly Val Pro Asp Arg Phe Ser Gly Ser Gly Ser Gly Thr<br>190　　　　　　　　195　　　　　　　　200 | | 3744 |
| gat ttc acc ctg acc atc agc agc ctg cag gcc gag gat gtg gcc gtg<br>Asp Phe Thr Leu Thr Ile Ser Ser Leu Gln Ala Glu Asp Val Ala Val<br>205　　　　　　　　210　　　　　　　　215 | | 3792 |
| tac tac tgc cag cag cac tac cgg acc cca cca acc ttc gga cag gga<br>Tyr Tyr Cys Gln Gln His Tyr Arg Thr Pro Pro Thr Phe Gly Gln Gly<br>220　　　　　　　　225　　　　　　　　230 | | 3840 |
| acc aag gtg gag atc aag gccacgtgcc ctccatgtcc agccccgaa<br>Thr Lys Val Glu Ile Lys<br>235　　　　　　　　240 | | 3888 |
| ctgctgggcg ggcctagcgt gttcctgttt cccctaagc ctaaagatac actgatgatt | | 3948 |
| agtagaaccc cagaggtcac atgcgtggtc gtggacgtgt cccacgaaga gcctgacgtg | | 4008 |
| aagttcaact ggtacgtgga tggcgtggag gtgcacaatg ctaagactaa accacgcgaa | | 4068 |
| gagcagtata atagtacata ccgagtcgtg tcagtcctga cagtgctgca ccaggattgg | | 4128 |
| ctgaacggca aggagtataa gtgcaaggtg tctaacaagg ccctgccgc ccctatcgag | | 4188 |
| aaaacaatta gcaaggccaa agggcagcca cgggaacccc aggtctacac tctgccaccc | | 4248 |
| tcaagagatg aactgactaa gaaccaggtc agcctgacct gtctggtgaa aggcttctac | | 4308 |
| cccagcgaca tcgccgtgga gtgggaaagt aacggccagc tgagaataaa ctacaagact | | 4368 |

```
accccteccag tgctggatag cgacgggtcc ttcttcctgt atagcaagct gacagtggac    4428
aaatcccgct ggcagcaggg aaacgtcttt tcctgttctg tgatgcatga ggccctgcac    4488
aatcattaca cccagaagag tctgtcactg agccccggca aatgataagc ttgcggccgc    4548
ttcgagcaga catgataaga tacattgatg agtttggaca aaccacaact agaatgcagt    4608
gaaaaaaatg ctttatttgt gaaatttgtg atgctattgc tttatttgta accattataa    4668
gctgcaataa acaagttaac aacaacaatt gcattcattt tatgtttcag gttcaggggg    4728
agatgtggga ggttttttaa agcaagtaaa acctctacaa atgtggtaaa atcgataagg    4788
atcttcctag agcatggcta cgtagataag tagcatggcg ggttaatcat taactacaag    4848
gaacccctag tgatggagtt ggccactccc tctctgcgcg ctcgctcgct cactgaggcc    4908
gggcgaccaa aggtcgcccg acgcccgggc tttgcccggg cggcctcagt gagcgagcga    4968
gcgcgcagcc ttaattaacc taattcactg gccgtcgttt tacaacgtcg tgactgggaa    5028
aaccctggcg ttacccaact taatcgcctt gcagcacatc cccctttcgc cagctggcgt    5088
aatagcgaag aggcccgcac cgatcgccct tcccaacagt tgcgcagcct gaatggcgaa    5148
tgggacgcgc cctgtagcgg cgcattaagc gcggcgggtg tggtggttac gcgcagcgtg    5208
accgctacac ttgccagcgc cctagcgccc gctccttttcg ctttcttccc ttcctttctc    5268
gccacgttcg ccggctttcc ccgtcaagct ctaaatcggg ggctccctt agggttccga    5328 tttagtgctt tacggcacct cgaccccaaa aaacttgatt agggtgatgg ttcacgtagt    5388
gggccatcgc cctgatagac ggttttttcgc cctttgacgt tggagtccac gttctttaat    5448
agtggactct tgttccaaac tggaacaaca ctcaaccctc tctcggtcta ttcttttgat    5508
ttataaggga ttttgccgat ttcggcctat tggttaaaaa atgagctgat ttaacaaaaa    5568
tttaacgcga attttaacaa aatattaacg cttacaattt aggtggcact tttcggggaa    5628
atgtgcgcgg aacccctatt tgtttatttt tctaaataca ttcaaatatg tatccgctca    5688
tgagacaata accctgataa atgcttcaat aatattgaaa aaggaagagt atgagtattc    5748
aacatttccg tgtcgccctt attcccttt ttgcggcatt ttgccttcct gtttttgctc    5808
acccagaaac gctggtgaaa gtaaaagatg ctgaagatca gttgggtgca cgagtgggtt    5868
acatcgaact ggatctcaac agcggtaaga tccttgagag ttttcgcccc gaagaacgtt    5928
ttccaatgat gagcactttt aaagttctgc tatgtggcgc ggtattatcc cgtattgacg    5988
ccgggcaaga gcaactcggt cgccgcatac actattctca gaatgacttg gttgagtact    6048
caccagtcac agaaaagcat cttacggatg gcatgacagt aagagaatta tgcagtgctg    6108
ccataaccat gagtgataac actgcggcca acttacttct gacaacgatc ggaggaccga    6168
aggagctaac cgcttttttg cacaacatgg gggatcatgt aactcgcctt gatcgttggg    6228
aaccggagct gaatgaagcc ataccaaacg acgagcgtga ccacgatg cctgtagcaa    6288 tggcaacaac gttgcgcaaa ctattaactg gcgaactact tactctagct tcccggcaac    6348
aattaataga ctggatggag gcggataaag ttgcaggacc acttctgcgc tcggcccttc    6408
cggctggctg gtttattgct gataaatctg gagccggtga gcgtgggtct cgcggtatca    6468
ttgcagcact ggggccagat ggtaagccct cccgtatcgt agttatctac acgacgggga    6528
gtcaggcaac tatggatgaa cgaaatagac agatcgctga gataggtgcc tcactgatta    6588
agcattggta actgtcagac caagtttact catatatact ttagattgat ttaaaacttc    6648
atttttaatt taaaaggatc taggtgaaga tccttttga taatctcatg accaaaatcc    6708
cttaacgtga gttttcgttc cactgagcgt cagacccccgt agaaaagatc aaaggatctt    6768
```

```
cttgagatcc ttttttttctg cgcgtaatct gctgcttgca acaaaaaaaa ccaccgctac    6828
cagcggtggt ttgtttgccg gatcaagagc taccaactct ttttccgaag gtaactggct    6888
tcagcagagc gcagatacca atactgttc ttctagtgta gccgtagtta ggccaccact    6948
tcaagaactc tgtagcaccg cctacatacc tcgctctgct aatcctgtta ccagtggctg    7008
ctgccagtgg cgataagtcg tgtcttaccg ggttggactc aagacgatag ttaccggata    7068
aggcgcagcg gtcgggctga acggggggtt cgtgcacaca gcccagcttg gagcgaacga    7128
cctacaccga actgagatac ctacagcgtg agctatgaga aagcgccacg cttcccgaag    7188
ggagaaaggc ggacaggtat ccggtaagcg cagggtcgg aacaggagag cgcacgaggg    7248
agcttccagg gggaaacgcc tggtatcttt atagtcctgt cgggtttcgc cacctctgac    7308
ttgagcgtcg atttttgtga tgctcgtcag ggggcggag cctatggaaa aacgccagca    7368
acgcggcctt tttacggttc ctggcctttt gctggccttt tgctcacatg ttctttcctg    7428
cgttatcccc tgattctgtg gataaccgta ttaccgcctt tgagtgagct gataccgctc    7488
gccgcagccg aacgaccgag cgcagcgagt cagtgagcga ggaagcggaa gagcgcccaa    7548
tacgcaaacc gcctctcccc gcgcgttggc cgattcatta atgcagctgg cacgacaggt    7608
ttcccgactg gaaagcgggc agtgagcgca acgcaattaa tgtgagttag ctcactcatt    7668
aggcacccca ggctttacac tttatgcttc cggctcgtat gttgtgtgga attgtgagcg    7728
gataacaatt tcacacagga aacagctatg accatgatta cgccagattt aattaa       7784
```

<210> SEQ ID NO 41
<211> LENGTH: 129
<212> TYPE: PRT
<213> ORGANISM: Artificial sequence
<220> FEATURE:
<223> OTHER INFORMATION: Synthetic Construct

<400> SEQUENCE: 41

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser
```

<210> SEQ ID NO 42
<211> LENGTH: 111
<212> TYPE: PRT
<213> ORGANISM: Artificial sequence
<220> FEATURE:
<223> OTHER INFORMATION: Synthetic Construct

<400> SEQUENCE: 42

```
Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65              70                  75                  80

Ser Leu Gln Ala Glu Asp Val Ala Val Tyr Tyr Cys Gln Gln His Tyr
                85                  90                  95

Arg Thr Pro Pro Thr Phe Gly Gln Gly Thr Lys Val Glu Ile Lys
            100                 105                 110
```

<210> SEQ ID NO 43
<211> LENGTH: 7782
<212> TYPE: DNA
<213> ORGANISM: Artificial sequence
<220> FEATURE:
<223> OTHER INFORMATION: Plasmid carrying TCN032 and Fi6 monoclonal antibodies
<220> FEATURE:
<221> NAME/KEY: repeat_region
<222> LOCATION: (14)..(143)
<220> FEATURE:
<221> NAME/KEY: polyA_signal
<222> LOCATION: (204)..(252)
<223> OTHER INFORMATION: synthetic polyA
<220> FEATURE:
<221> NAME/KEY: misc_feature
<222> LOCATION: (261)..(267)
<223> OTHER INFORMATION: stop cassette (complement)
<220> FEATURE:
<221> NAME/KEY: misc_feature
<222> LOCATION: (268)..(588)
<223> OTHER INFORMATION: constant light (on complementary strand)
<220> FEATURE:
<221> NAME/KEY: misc_feature
<222> LOCATION: (967)..(971)
<223> OTHER INFORMATION: Kozak (located on complementary strand)
<220> FEATURE:
<221> NAME/KEY: misc_feature
<222> LOCATION: (972)..(1019)
<223> OTHER INFORMATION: c-myc 5' UTR (located on complementary strand)
<220> FEATURE:
<221> NAME/KEY: misc_feature
<222> LOCATION: (1026)..(1094)
<223> OTHER INFORMATION: CMV\mp2
<220> FEATURE:
<221> NAME/KEY: enhancer
<222> LOCATION: (1026)..(1094)
<220> FEATURE:
<221> NAME/KEY: misc_feature
<222> LOCATION: (1564)..(1689)
<220> FEATURE:
<221> NAME/KEY: misc_feature
<222> LOCATION: (1696)..(1743)
<223> OTHER INFORMATION: c-myc 5' UTR
<220> FEATURE:
<221> NAME/KEY: misc_feature
<222> LOCATION: (1744)..(1748)
<223> OTHER INFORMATION: Kozak
<220> FEATURE:
<221> NAME/KEY: misc_feature
<222> LOCATION: (1749)..(1805)
<223> OTHER INFORMATION: leader -continued

```
<220> FEATURE:
<221> NAME/KEY: CDS
<222> LOCATION: (1806)..(2165)
<223> OTHER INFORMATION: TCN032 variable heavy
<220> FEATURE:
<221> NAME/KEY: repeat_region
<222> LOCATION: (1845)..(4974)
<223> OTHER INFORMATION: inverted terminal repeat
<220> FEATURE:
<221> NAME/KEY: repeat_region
<222> LOCATION: (1845)..(4974)
<223> OTHER INFORMATION: inverted terminal repeat (located on
      complement)
<220> FEATURE:
<221> NAME/KEY: CDS
<222> LOCATION: (2166)..(2459)
<223> OTHER INFORMATION: CH1
<220> FEATURE:
<221> NAME/KEY: misc
<222> LOCATION: (2166)..(2459)
<223> OTHER INFORMATION: CH1
<220> FEATURE:
<221> NAME/KEY: CDS
<222> LOCATION: (2460)..(3152)
<223> OTHER INFORMATION: hinge-CH2'-CH3'
<220> FEATURE:
<221> NAME/KEY: misc_feature
<222> LOCATION: (3153)..(3164)
<223> OTHER INFORMATION: furin cleavage site
<220> FEATURE:
<221> NAME/KEY: misc_feature
<222> LOCATION: (3165)..(3236)
<223> OTHER INFORMATION: F2A linker
<220> FEATURE:
<221> NAME/KEY: misc_feature
<222> LOCATION: (3239)..(3296)
<220> FEATURE:
<221> NAME/KEY: misc_feature
<222> LOCATION: (3239)..(3296)
<220> FEATURE:
<221> NAME/KEY: CDS
<222> LOCATION: (3297)..(3683)
<223> OTHER INFORMATION: FI6 VH
<220> FEATURE:
<221> NAME/KEY: CDS
<222> LOCATION: (3684)..(4004)
<223> OTHER INFORMATION: CH1
<220> FEATURE:
<221> NAME/KEY: CDS
<222> LOCATION: (4005)..(4673)
<223> OTHER INFORMATION: CH2-3
<220> FEATURE:
<221> NAME/KEY: misc_feature
<222> LOCATION: (4674)..(4680)
<223> OTHER INFORMATION: Stop cassette
<220> FEATURE:
<221> NAME/KEY: misc_feature
<222> LOCATION: (4674)..(4680)
<220> FEATURE:
<221> NAME/KEY: polyA_signal
<222> LOCATION: (4693)..(4770)
<223> OTHER INFORMATION: TKpAshort
<220> FEATURE:
<221> NAME/KEY: rep_origin
<222> LOCATION: (5151)..(5606)
<220> FEATURE:
<221> NAME/KEY: CDS
<222> LOCATION: (5737)..(6594)
<223> OTHER INFORMATION: Amp-R
<220> FEATURE:
<221> NAME/KEY: misc_feature
<222> LOCATION: (6768)..(.7356)
<223> OTHER INFORMATION: col\E1\origin

<400> SEQUENCE: 43
ggccttaatt aggctgcgcg ctcgctcgct cactgaggcc gcccgggcaa agcccgggcg     60
tcgggcgacc tttggtcgcc cggcctcagt gagcgagcga gcgcgcagag agggagtggc    120
```

-continued

| | |
|---|---|
| caactccatc actaggggtt ccttgtagtt aatgattaac ccgccatgct acttatctac | 180 |
| gtagccatgc tctaggaaga tctcacacaa aaaaccaaca cacagatgta atgaaaataa | 240 |
| agatatttta ttgcggccgc tttatcagca ctctccgcgg ttgaagctct tggtcactgg | 300 |
| gctgctcagt ccctggtggg tcacctcgca ggcgtacacc ttgtgcttct cgtaatcggc | 360 |
| cttgctcagg gtcagggtgc tgctcaggct gtaggtgcta tccttgctat cctgctcggt | 420 |
| cacgctctcc tggctgtttc cgctctgcag ggcgttatcc accttccact gcaccttggc | 480 |
| ctcccgtggg tagaagttgt tcagcaggca caccacgctg gcggttccgc tcttcagctg | 540 |
| ctcatcgctt ggtgggaaga tgaacacgct tggggcggcc accgtacgct tgatctccac | 600 |
| ccgggttcct cctccgaagg tcagtggtgg gctgtagctc tgctggcagt agtaggtggc | 660 |
| gaaatcctct ggctgcaggc tggtgatggt cagggtgaaa tcggttccgc ttccgcttcc | 720 |
| gctgaaccgg cttggcactc cgctctgcag tccgctggcg gcgctgatca gtcccttttgg | 780 |
| ggcctttcct ggccgctgct ggtaccagtt caggtacttg tagatgttct ggctggcccg | 840 |
| gcaggtgatg gtcacccgat ctcccacgct ggcgctcagg ctgcttgggc tctgggtcat | 900 |
| ctggatatcg ctgttggtca ccagggccag gctcagggcg atcagcagca gcagctgcat | 960 |
| tctcatggtg gagagtcgcg tccttgctcg ggtgttgtaa gttccagtgc aaagtgcccc | 1020 |
| aattggcgat ctgacggttc actaaacgag ctctgcttat ataggcctcc caccgtacac | 1080 |
| gccacctcga cataccctagt tattaatagt aatcaattac ggggtcatta gttcatagcc | 1140 |
| catatatgga gttccgcgtt acataactta cggtaaatgg cccgcctggc tgaccgccca | 1200 |
| acgaccccg cccattgacg tcaataatga cgtatgttcc catagtaacg ccaatagga | 1260 |
| ctttccattg acgtcaatgg gtggagtatt tacggtaaac tgcccacttg gcagtacatc | 1320 |
| aagtgtatca tatgccaagt acgccccta ttgacgtcaa tgacggtaaa tggcccgcct | 1380 |
| ggcattatgc ccagtacatg accttatggg actttcctac ttggcagtac atctacgtat | 1440 |
| tagtcatcgc tattaccatg gtgatgcggt tttggcagta catcaatggg cgtggatagc | 1500 |
| ggtttgactc acggggattt ccaagtctcc accccattga cgtcaatggg agtttgtttt | 1560 |
| ggcaccaaaa tcaacgggac tttccaaaat gtcgtaacaa ctccgcccca ttgacgcaaa | 1620 |
| tgggcggtag gcgtgtacgg tgggaggtct atataagcag agctggttta gtgaaccgtc | 1680 |
| agatccgctg ctagcgggca cttttgcactg gaacttacaa cacccgagca aggacgcgac | 1740 |
| tctccaccat gcgcatgcag ctgctgctgc tgatcgccct gagcctggcc ctggtgacca | 1800 |
| acagc cag gtg cag ctg cag gag agc gga cca gga ctg gtg aag cca agc<br>        Gln Val Gln Leu Gln Glu Ser Gly Pro Gly Leu Val Lys Pro Ser<br>        1             5                 10               15 | 1850 |
| gag acc ctg agc ctg acc tgc acc gtg agc gga agc agc atc agc aac<br>Glu Thr Leu Ser Leu Thr Cys Thr Val Ser Gly Ser Ser Ile Ser Asn<br>                  20                25                30 | 1898 |
| tac tac tgg agc tgg atc cgg cag agc cca gga aag gga ctg gag tgg<br>Tyr Tyr Trp Ser Trp Ile Arg Gln Ser Pro Gly Lys Gly Leu Glu Trp<br>        35                  40                45 | 1946 |
| atc gga ttc atc tac tac gga gga aac acc aag tac aac cca agc ctg<br>Ile Gly Phe Ile Tyr Tyr Gly Gly Asn Thr Lys Tyr Asn Pro Ser Leu<br>        50                  55                60 | 1994 |
| aag agc cgg gtg acc atc agc cag gat acc agc aag agc cag gtg agc<br>Lys Ser Arg Val Thr Ile Ser Gln Asp Thr Ser Lys Ser Gln Val Ser<br>     65                  70                75 | 2042 |
| ctg acc atg agc agc gtg acc gcc gcc gag agc gcc gtg tac ttc tgc<br>Leu Thr Met Ser Ser Val Thr Ala Ala Glu Ser Ala Val Tyr Phe Cys<br>80                  85                90                95 | 2090 |

```
gcc cgg gcc agc tgc agc gga gga tac tgc atc ctg gat tac tgg gga      2138
Ala Arg Ala Ser Cys Ser Gly Gly Tyr Cys Ile Leu Asp Tyr Trp Gly
            100                 105                 110 cag gga acc ctg gtg acc gtg agc agc gcg tcg acc aag gga cct tcg      2186
Gln Gly Thr Leu Val Thr Val Ser Ser Ala Ser Thr Lys Gly Pro Ser
        115                 120                 125 gtc ttc ccc ctg gca ccc tcc tcc aag agc acc tct ggg ggc aca gcg      2234
Val Phe Pro Leu Ala Pro Ser Ser Lys Ser Thr Ser Gly Gly Thr Ala
    130                 135                 140 gcc ctg ggc tgc ctg gtc aag gac tac ttc ccc gaa ccg gtg acg gtg      2282
Ala Leu Gly Cys Leu Val Lys Asp Tyr Phe Pro Glu Pro Val Thr Val
145                 150                 155 tcg tgg aac tca ggc gcc ctg acc agc ggc gtg cac acc ttc ccg gct      2330
Ser Trp Asn Ser Gly Ala Leu Thr Ser Gly Val His Thr Phe Pro Ala
160                 165                 170                 175 gtc cta cag tcc tca gga ctc tac tcc ctc agc agc gtg gtg acc gtg      2378
Val Leu Gln Ser Ser Gly Leu Tyr Ser Leu Ser Ser Val Val Thr Val
            180                 185                 190 ccc tcc agc agc ttg ggc acc cag acc tac atc tgc aac gtg aat cac      2426
Pro Ser Ser Ser Leu Gly Thr Gln Thr Tyr Ile Cys Asn Val Asn His
        195                 200                 205 aag ccc agc aac acc aag gtg gac aag aaa gtt gaa cca aag agc tgc      2474
Lys Pro Ser Asn Thr Lys Val Asp Lys Lys Val Glu Pro Lys Ser Cys
    210                 215                 220 gac aag acc cac acg tgt ccc ccc tgc cct gcc cct gaa ctg ctg gga      2522
Asp Lys Thr His Thr Cys Pro Pro Cys Pro Ala Pro Glu Leu Leu Gly
225                 230                 235 ggc ccc agc gtg ttc ctg ttc ccc cca aag ccc aag gac acc ctg atg      2570
Gly Pro Ser Val Phe Leu Phe Pro Pro Lys Pro Lys Asp Thr Leu Met
240                 245                 250                 255 atc agc cgg acc ccc gaa gtg acc tgc gtg gtg gtg gac gtg tcc cac      2618
Ile Ser Arg Thr Pro Glu Val Thr Cys Val Val Val Asp Val Ser His
            260                 265                 270 gag gac cct gaa gtg aag ttt aat tgg tac gtg gac ggc gtg gaa gtg      2666
Glu Asp Pro Glu Val Lys Phe Asn Trp Tyr Val Asp Gly Val Glu Val
        275                 280                 285 cac aac gcc aag acc aag ccc aga gag gaa cag tac aac agc acc tac      2714
His Asn Ala Lys Thr Lys Pro Arg Glu Glu Gln Tyr Asn Ser Thr Tyr
    290                 295                 300 cgg gtg gtg tcc gtg ctg acc gtg ctg cac cag gac tgg ctg aac ggc      2762
Arg Val Val Ser Val Leu Thr Val Leu His Gln Asp Trp Leu Asn Gly
305                 310                 315 aaa gag tac aag tgc aag gtg tcc aac aag gcc ctg cct gcc ccc atc      2810
Lys Glu Tyr Lys Cys Lys Val Ser Asn Lys Ala Leu Pro Ala Pro Ile
320                 325                 330                 335 gag aaa acc atc agc aag gcc aag ggc cag ccc cgc gag cct cag gtc      2858
Glu Lys Thr Ile Ser Lys Ala Lys Gly Gln Pro Arg Glu Pro Gln Val
            340                 345                 350 tac aca ctg ccc ccc agc cgg gaa gag atg acc aag aac cag gtg tcc      2906
Tyr Thr Leu Pro Pro Ser Arg Glu Glu Met Thr Lys Asn Gln Val Ser
        355                 360                 365 ctg acc tgc ctg gtc aag ggc ttc tac ccc agc gac atc gcc gtg gaa      2954
Leu Thr Cys Leu Val Lys Gly Phe Tyr Pro Ser Asp Ile Ala Val Glu
    370                 375                 380 tgg gag agc aac ggc cag ccc gag aac aac tac aag acc acc ccc cct      3002
Trp Glu Ser Asn Gly Gln Pro Glu Asn Asn Tyr Lys Thr Thr Pro Pro
385                 390                 395 gtg ctg gac agc gac ggc tca ttc ttc ctg tat agc aag ctg acc gtg      3050
Val Leu Asp Ser Asp Gly Ser Phe Phe Leu Tyr Ser Lys Leu Thr Val
400                 405                 410                 415
```

-continued

| | |
|---|---|
| gac aag agc cgg tgg cag cag ggc aac gtg ttc agc tgc agc gtg atg<br>Asp Lys Ser Arg Trp Gln Gln Gly Asn Val Phe Ser Cys Ser Val Met<br>    420                              425                        430 | 3098 |
| cac gag gcc ctg cac aac cac tac acc cag aag tcc ctg agc ctg agc<br>His Glu Ala Leu His Asn His Tyr Thr Gln Lys Ser Leu Ser Leu Ser<br>             435                       440                        445 | 3146 |
| ccc ggc agaaagcgga gagcccccgt gaagcagacc ctgaacttcg acctgctgaa<br>Pro Gly | 3202 |
| gctggccggc gacgtggaaa gcaaccctgg ccctatgtac agaatgcagc tgctgagctg | 3262 |
| catcgccctg agcctggccc tggtgaccaa cagc cag gtg caa cta gtg gag agc<br>                                                              Gln Val Gln Leu Val Glu Ser<br>                                                                         450                        455 | 3317 |
| gga gga gga gtg gtg cag cca gga cgg agc ctg cgg ctg agc tgc gcc<br>Gly Gly Gly Val Val Gln Pro Gly Arg Ser Leu Arg Leu Ser Cys Ala<br>             460                       465                        470 | 3365 |
| gcc agc gga ttc acc ttc agc acc tac gcc atg cac tgg gtg cgg cag<br>Ala Ser Gly Phe Thr Phe Ser Thr Tyr Ala Met His Trp Val Arg Gln<br>          475                         480                        485 | 3413 |
| gcc cca gga aag gga ctg gag tgg gtg gcc gtg atc agc tac gat gcc<br>Ala Pro Gly Lys Gly Leu Glu Trp Val Ala Val Ile Ser Tyr Asp Ala<br>490                                495                        500 | 3461 |
| aac tac aag tac tac gcc gat agc gtg aag gga cgg ttc acc atc agc<br>Asn Tyr Lys Tyr Tyr Ala Asp Ser Val Lys Gly Arg Phe Thr Ile Ser<br>505                        510                          515                        520 | 3509 |
| cgg gat aac agc aag aac acc ctg tac ctg cag atg aac agc ctg cgg<br>Arg Asp Asn Ser Lys Asn Thr Leu Tyr Leu Gln Met Asn Ser Leu Arg<br>                 525                        530                        535 | 3557 |
| gcc gag gat acc gcc gtg tac tac tgc gcc aag gat agc cag ctg cgg<br>Ala Glu Asp Thr Ala Val Tyr Tyr Cys Ala Lys Asp Ser Gln Leu Arg<br>           540                       545                        550 | 3605 |
| agc ctg ctg tac ttc gag tgg ctg agc cag gga tac ttc gat tac tgg<br>Ser Leu Leu Tyr Phe Glu Trp Leu Ser Gln Gly Tyr Phe Asp Tyr Trp<br>          555                         560                        565 | 3653 |
| gga cag gga acc ctg gtg acc gtg agc agc gcc agc acc aag ggg ccc<br>Gly Gln Gly Thr Leu Val Thr Val Ser Ser Ala Ser Thr Lys Gly Pro<br>        570                         575                        580 | 3701 |
| agc gtg ttc cca ctg gcc cca agc agc aag agc acc agc gga gga acc<br>Ser Val Phe Pro Leu Ala Pro Ser Ser Lys Ser Thr Ser Gly Gly Thr<br>585                        590                          595                        600 | 3749 |
| gcc gcc ctg gga tgc ctg gtg aag gat tac ttc cca gag cca gtg acc<br>Ala Ala Leu Gly Cys Leu Val Lys Asp Tyr Phe Pro Glu Pro Val Thr<br>                      605                        610                        615 | 3797 |
| gtg agc tgg aac agc gga gcc ctg acc agc gga gtg cac acc ttc cca<br>Val Ser Trp Asn Ser Gly Ala Leu Thr Ser Gly Val His Thr Phe Pro<br>                620                        625                        630 | 3845 |
| gcc gtg ctg cag agc agc gga ctg tat agc ctg agc agc gtg gtg acc<br>Ala Val Leu Gln Ser Ser Gly Leu Tyr Ser Leu Ser Ser Val Val Thr<br>            635                       640                        645 | 3893 |
| gtg cca agc agc agc ctg gga acc cag acc tac atc tgc aac gtg aac<br>Val Pro Ser Ser Ser Leu Gly Thr Gln Thr Tyr Ile Cys Asn Val Asn<br>650                        655                        660 | 3941 |
| cac aag cca agc aac acc aag gtg gat aag aag gtg gag cca aag agc<br>His Lys Pro Ser Asn Thr Lys Val Asp Lys Lys Val Glu Pro Lys Ser<br>665                      670                        675                        680 | 3989 |
| tgc gat aag acc cac acg tgc cct cca tgt cca gcc ccc gaa ctg ctg<br>Cys Asp Lys Thr His Thr Cys Pro Pro Cys Pro Ala Pro Glu Leu Leu<br>                685                        690                        695 | 4037 |

| | | |
|---|---|---|
| ggc ggg cct agc gtg ttc ctg ttt ccc cct aag cct aaa gat aca ctg<br>Gly Gly Pro Ser Val Phe Leu Phe Pro Pro Lys Pro Lys Asp Thr Leu<br>700                                  705                         710 | 4085 |
| atg att agt aga acc cca gag gtc aca tgc gtg gtg gtg gac gtg tcc<br>Met Ile Ser Arg Thr Pro Glu Val Thr Cys Val Val Val Asp Val Ser<br>            715                         720                       725 | 4133 |
| cac gaa gag cct gac gtg aag ttc aac tgg tac gtg gat ggc gtg gag<br>His Glu Glu Pro Asp Val Lys Phe Asn Trp Tyr Val Asp Gly Val Glu<br>730                                  735                         740 | 4181 |
| gtg cac aat gct aag act aaa cca cgc gaa gag cag tat aat agt aca<br>Val His Asn Ala Lys Thr Lys Pro Arg Glu Glu Gln Tyr Asn Ser Thr<br>745                          750                         755                    760 | 4229 |
| tac cga gtc gtg tca gtc ctg aca gtg ctg cac cag gat tgg ctg aac<br>Tyr Arg Val Val Ser Val Leu Thr Val Leu His Gln Asp Trp Leu Asn<br>                       765                       770                       775 | 4277 |
| ggc aag gag tat aag tgc aag gtg tct aac aag gcc ctg ccc gcc cct<br>Gly Lys Glu Tyr Lys Cys Lys Val Ser Asn Lys Ala Leu Pro Ala Pro<br>                780                         785                         790 | 4325 |
| atc gag aaa aca att agc aag gcc aaa ggg cag cca cgg gaa ccc cag<br>Ile Glu Lys Thr Ile Ser Lys Ala Lys Gly Gln Pro Arg Glu Pro Gln<br>795                                800                         805 | 4373 |
| gtc tac act ctg cca ccc tca aga gat gaa ctg act aag aac cag gtc<br>Val Tyr Thr Leu Pro Pro Ser Arg Asp Glu Leu Thr Lys Asn Gln Val<br>810                                 815                      820 | 4421 |
| agc ctg acc tgt ctg gtg aaa ggc ttc tac ccc agc gac atc gcc gtg<br>Ser Leu Thr Cys Leu Val Lys Gly Phe Tyr Pro Ser Asp Ile Ala Val<br>825                           830                         835                   840 | 4469 |
| gag tgg gaa agt aac ggc cag cct gag aat aac tac aag act acc cct<br>Glu Trp Glu Ser Asn Gly Gln Pro Glu Asn Asn Tyr Lys Thr Thr Pro<br>                       845                       850                       855 | 4517 |
| cca gtg ctg gat agc gac ggg tcc ttc ttc ctg tat agc aag ctg aca<br>Pro Val Leu Asp Ser Asp Gly Ser Phe Phe Leu Tyr Ser Lys Leu Thr<br>                      860                       865                      870 | 4565 |
| gtg gac aaa tcc cgc tgg cag cag gga aac gtc ttt tcc tgt tct gtg<br>Val Asp Lys Ser Arg Trp Gln Gln Gly Asn Val Phe Ser Cys Ser Val<br>875                             880                       885 | 4613 |
| atg cat gag gcc ctg cac aat cat tac acc cag aag agt ctg tca ctg<br>Met His Glu Ala Leu His Asn His Tyr Thr Gln Lys Ser Leu Ser Leu<br>         890                       895                       900 | 4661 |
| agc ccc ggc aaa tgataaaaag cttctcgaga aggaacccgc gctatgacgg<br>Ser Pro Gly Lys<br>905 | 4713 |
| caataaaaag acagaataaa acccacgggt gttgggtcgt tgttcataa acccgggaag | 4773 |
| cttatcgata aggatcttcc tagagcatgg ctacgtagat aagtagcatg gcgggttaat | 4833 |
| cattaactac aaggaacccc tagtgatgga gttggccact ccctctctgc gcgctcgctc | 4893 |
| gctcactgag gccgggcgac caaaggtcgc ccgacgcccg gctttgccc gggcggcctc | 4953 |
| agtgagcgag cgagcgcgca gccttaatta acctaattca ctggccgtcg ttttacaacg | 5013 |
| tcgtgactgg gaaaaccctg gcgttaccca acttaatcgc cttgcagcac atccccctt | 5073 |
| cgccagctgg cgtaatagcg aagaggcccg caccgatcgc ccttcccaac agttgcgcag | 5133 |
| cctgaatggc gaatgggacg cgccctgtag cggcgcatta agcgcggcgg gtgtggtggt | 5193 |
| tacgcgcagc gtgaccgcta cacttgccag cgccctagcg cccgctcctt tcgctttctt | 5253 |
| cccttccttt ctcgccacgt tcgccggctt tccccgtcaa gctctaaatc gggggctccc | 5313 |
| tttagggttc cgatttagtg ctttacggca cctcgacccc aaaaaacttg attagggtga | 5373 |
| tggttcacgt agtgggccat cgccctgata gacggttttt cgccctttga cgttggagtc | 5433 |

```
cacgttcttt aatagtggac tcttgttcca aactggaaca acactcaacc ctatctcggt      5493
ctattctttt gatttataag ggattttgcc gatttcggcc tattggttaa aaaatgagct      5553
gatttaacaa aaatttaacg cgaattttaa caaaatatta acgcttacaa tttaggtggc      5613
acttttcggg gaaatgtgcg cggaaccccct atttgtttat ttttctaaat acattcaaat      5673
atgtatccgc tcatgagaca ataaccctga taaatgcttc aataatattg aaaaaggaag      5733 agt atg agt att caa cat ttc cgt gtc gcc ctt att ccc ttt ttt gcg        5781
    Met Ser Ile Gln His Phe Arg Val Ala Leu Ile Pro Phe Phe Ala
        910             915                 920 gca ttt tgc ctt cct gtt ttt gct cac cca gaa acg ctg gtg aaa gta        5829
Ala Phe Cys Leu Pro Val Phe Ala His Pro Glu Thr Leu Val Lys Val
925                 930                 935 aaa gat gct gaa gat cag ttg ggt gca cga gtg ggt tac atc gaa ctg        5877
Lys Asp Ala Glu Asp Gln Leu Gly Ala Arg Val Gly Tyr Ile Glu Leu
940                 945                 950                 955 gat ctc aac agc ggt aag atc ctt gag agt ttt cgc ccc gaa gaa cgt        5925
Asp Leu Asn Ser Gly Lys Ile Leu Glu Ser Phe Arg Pro Glu Glu Arg
                960                 965                 970 ttt cca atg atg agc act ttt aaa gtt ctg cta tgt ggc gcg gta tta        5973
Phe Pro Met Met Ser Thr Phe Lys Val Leu Leu Cys Gly Ala Val Leu
        975                 980                 985 tcc cgt att gac gcc ggg caa gag caa ctc ggt cgc cgc ata cac tat        6021
Ser Arg Ile Asp Ala Gly Gln Glu Gln Leu Gly Arg Arg Ile His Tyr
        990                 995                 1000 tct cag  aat gac ttg gtt gag  tac tca cca gtc aca  gaa aag cat        6066
Ser Gln  Asn Asp Leu Val Glu  Tyr Ser Pro Val Thr  Glu Lys His
    1005                 1010                 1015 ctt acg  gat ggc atg aca gta  aga gaa tta tgc agt  gct gcc ata        6111
Leu Thr  Asp Gly Met Thr Val  Arg Glu Leu Cys Ser  Ala Ala Ile
    1020                 1025                 1030 acc atg  agt gat aac act gcg  gcc aac tta ctt ctg  aca acg atc        6156
Thr Met  Ser Asp Asn Thr Ala  Ala Asn Leu Leu Leu  Thr Thr Ile
    1035                 1040                 1045 gga gga  ccg aag gag cta acc  gct ttt ttg cac aac  atg ggg gat        6201
Gly Gly  Pro Lys Glu Leu Thr  Ala Phe Leu His Asn  Met Gly Asp
    1050                 1055                 1060 cat gta  act cgc ctt gat cgt  tgg gaa ccg gag ctg  aat gaa gcc        6246
His Val  Thr Arg Leu Asp Arg  Trp Glu Pro Glu Leu  Asn Glu Ala
    1065                 1070                 1075 ata cca  aac gac gag cgt gac  acc acg atg cct gta  gca atg gca        6291
Ile Pro  Asn Asp Glu Arg Asp  Thr Thr Met Pro Val  Ala Met Ala
    1080                 1085                 1090 aca acg  ttg cgc aaa cta tta  act ggc gaa cta ctt  act cta gct        6336
Thr Thr  Leu Arg Lys Leu Leu  Thr Gly Glu Leu Leu  Thr Leu Ala
    1095                 1100                 1105 tcc cgg  caa caa tta ata gac  tgg atg gag gcg gat  aaa gtt gca        6381
Ser Arg  Gln Gln Leu Ile Asp  Trp Met Glu Ala Asp  Lys Val Ala
    1110                 1115                 1120 gga cca  ctt ctg cgc tcg gcc  ctt ccg gct ggc tgg  ttt att gct        6426
Gly Pro  Leu Leu Arg Ser Ala  Leu Pro Ala Gly Trp  Phe Ile Ala
    1125                 1130                 1135 gat aaa  tct gga gcc ggt gag  cgt ggg tct cgc ggt  atc att gca        6471
Asp Lys  Ser Gly Ala Gly Glu  Arg Gly Ser Arg Gly  Ile Ile Ala
    1140                 1145                 1150 gca ctg  ggg cca gat ggt aag  ccc tcc cgt atc gta  gtt atc tac        6516
Ala Leu  Gly Pro Asp Gly Lys  Pro Ser Arg Ile Val  Val Ile Tyr
    1155                 1160                 1165
```

```
acg acg ggg agt cag gca act atg gat gaa cga aat aga cag atc      6561
Thr Thr Gly Ser Gln Ala Thr Met Asp Glu Arg Asn Arg Gln Ile
    1170                1175                1180 gct gag ata ggt gcc tca ctg att aag cat tgg taactgtcag            6604
Ala Glu Ile Gly Ala Ser Leu Ile Lys His Trp
    1185                1190 accaagttta ctcatatata ctttagattg atttaaaact tcattttaa tttaaaagga   6664 tctaggtgaa gatccttttt gataatctca tgaccaaaat cccttaacgt gagttttcgt  6724
tccactgagc gtcagacccc gtagaaaaga tcaaggatc ttcttgagat cctttttttc   6784
tgcgcgtaat ctgctgcttg caaacaaaaa aaccaccgct accagcggtg tttgtttgc   6844 cggatcaaga gctaccaact cttttccga aggtaactgg cttcagcaga gcgcagatac   6904
caaatactgt tcttctagtg tagccgtagt taggccacca cttcaagaac tctgtagcac   6964
cgcctacata cctcgctctg ctaatcctgt taccagtggc tgctgccagt ggcgataagt   7024
cgtgtcttac cgggttggac tcaagacgat agttaccgga taaggcgcag cggtcgggct   7084
gaacgggggg ttcgtgcaca cagcccagct tggagcgaac gacctacacc gaactgagat   7144
acctacagcg tgagctatga aaagcgcca cgcttcccga agggagaaag gcggacaggt    7204
atccggtaag cggcagggtc ggaacaggag agcgcacgag ggagcttcca gggggaaacg   7264
cctggtatct ttatagtcct gtcgggtttc gccacctctg acttgagcgt cgattttgt   7324 gatgctcgtc aggggggcgg agcctatgga aaaacgccag caacgcggcc ttttacggt   7384 tcctggcctt ttgctggcct tttgctcaca tgttctttcc tgcgttatcc cctgattctg   7444
tggataaccg tattaccgcc tttgagtgag ctgataccgc tcgccgcagc cgaacgaccg   7504
agcgcagcga gtcagtgagc gaggaagcgg aagagcgccc aatacgcaaa ccgcctctcc   7564
ccgcgcgttg gccgattcat taatgcagct ggcacgacag gtttcccgac tggaaagcgg   7624
gcagtgagcg caacgcaatt aatgtgagtt agctcactca ttaggcaccc caggctttac   7684
actttatgct tccggctcgt atgttgtgtg gaattgtgag cggataacaa tttcacacag   7744
gaaacagcta tgaccatgat tacgccagat ttaattaa                          7782

<210> SEQ ID NO 44
<211> LENGTH: 120
<212> TYPE: PRT
<213> ORGANISM: Artificial sequence
<220> FEATURE:
<223> OTHER INFORMATION: Synthetic Construct

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Asn Tyr
            20                  25                  30

Tyr Trp Ser Trp Ile Arg Gln Ser Pro Gly Lys Gly Leu Glu Trp Ile
        35                  40                  45

Gly Phe Ile Tyr Tyr Gly Gly Asn Thr Lys Tyr Asn Pro Ser Leu Lys
    50                  55                  60

Ser Arg Val Thr Ile Ser Gln Asp Thr Ser Lys Ser Gln Val Ser Leu
65                  70                  75                  80

Thr Met Ser Ser Val Thr Ala Ala Glu Ser Ala Val Tyr Phe Cys Ala
                85                  90                  95
```

```
Arg Ala Ser Cys Ser Gly Gly Tyr Cys Ile Leu Asp Tyr Trp Gly Gln
            100                 105                 110

Gly Thr Leu Val Thr Val Ser Ser
        115                 120

<210> SEQ ID NO 45
<211> LENGTH: 98
<212> TYPE: PRT
<213> ORGANISM: Artificial sequence
<220> FEATURE:
<223> OTHER INFORMATION: Synthetic Construct

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 46
<211> LENGTH: 231
<212> TYPE: PRT
<213> ORGANISM: Artificial sequence
<220> FEATURE:
<223> OTHER INFORMATION: Synthetic Construct

<400> SEQUENCE: 46

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230
```

<210> SEQ ID NO 47
<211> LENGTH: 129
<212> TYPE: PRT
<213> ORGANISM: Artificial sequence
<220> FEATURE:
<223> OTHER INFORMATION: Synthetic Construct

<400> SEQUENCE: 47

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser
```

<210> SEQ ID NO 48
<211> LENGTH: 107
<212> TYPE: PRT
<213> ORGANISM: Artificial sequence
<220> FEATURE:
<223> OTHER INFORMATION: Synthetic Construct

<400> SEQUENCE: 48

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His
            100                 105
```

<210> SEQ ID NO 49
<211> LENGTH: 223
<212> TYPE: PRT
<213> ORGANISM: Artificial sequence
<220> FEATURE:
<223> OTHER INFORMATION: Synthetic Construct

<400> SEQUENCE: 49

```
Thr Cys Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Glu Pro Asp
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 50
<211> LENGTH: 286
<212> TYPE: PRT
<213> ORGANISM: Artificial sequence
<220> FEATURE:
<223> OTHER INFORMATION: Synthetic Construct

<400> SEQUENCE: 50

```
Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95
```

-continued

```
Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
        130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
                180                 185                 190

Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
                260                 265                 270

Arg Gln Ile Ala Glu Ile Gly Ala Ser Leu Ile Lys His Trp
            275                 280                 285
```

COMPOSITIONS COMPRISING AAV EXPRESSING DUAL ANTIBODY CONSTRUCTS AND USES THEREOF

CROSS-REFERENCE TO RELATED APPLICATIONS

This is a continuation of U.S. patent application Ser. No. 16/460,623, filed Jul. 2, 2019, now pending, U.S. patent application Ser. No. 16/160,040, filed Oct. 15, 2018, now U.S. Pat. No. 10,385,119, issued Aug. 20, 2019, which is a continuation of U.S. patent application Ser. No. 15/310,555, filed Nov. 11, 2016, now U.S. Pat. No. 10,138,295, issued Nov. 27, 2018, which is a national stage application under 35 USC 371 of PCT/US2015/030533, filed May 13, 2015, now expired, which claims the benefit under 35 USC 119(e) of U.S. Provisional Patent Application No. 61/992,649, filed May 13, 2014. Each of these applications is hereby incorporated by reference in its entirety.

STATEMENT REGARDING FEDERALLY SPONSORED RESEARCH OR DEVELOPMENT

This invention was made with government support under grant number ARO No. 64047-LS-DRP awarded by Defense Advanced Research Projects Agency (DARPA). The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "14-7032PCT_Seq Listing_ST25.txt" and dated May 13, 2015 with a size of 220 KB.

BACKGROUND OF THE INVENTION

Monoclonal antibodies have been proven as effective therapeutics for cancer and other diseases. Current antibody therapy often involves repeat administration and long term treatment regimens, which are associated with a number of disadvantages, such as inconsistent serum levels and limited duration of efficacy per administration such that frequent re-administration is required and high cost. The use of antibodies as diagnostic tools and therapeutic modalities has found increasing use in recent years. The first FDA-approved monoclonal antibody for cancer treatment, Rituxan® (Rituximab) was approved in 1997 for the treatment of patients with non-Hodgkin's lymphoma and soon thereafter in 1995, Herceptin®, a humanized monoclonal antibody for treatment of patients with metastatic breast cancer, was approved. Numerous antibody-based therapies that are in various stages of clinical development are showing promise. Given the success of various monoclonal antibody therapies, it has been suggested the next generation of biopharmaceuticals will involve cocktails, i.e., mixtures, of antibodies.

One limitation to the widespread clinical application of antibody technology is that typically large amounts of antibody are required for therapeutic efficacy and the costs associated with production are significant. Chinese Hamster Ovarian (CHO) cells, SP20 and NSO2 myeloma cells are the most commonly used mammalian cell lines for commercial scale production of glycosylated human proteins such as antibodies. The yields obtained from mammalian cell line production typically range from 50-250 mg/L for 5-7 day culture in a batch fermenter or 300-1000 mg/L in 7-12 days in fed batch fermenters.

Adeno associated virus (AAV) is a desirable vector for delivering therapeutic genes due to its safety profile and capability of long term gene expression in vivo. Recombinant AAV vectors (rAAV) have been previously used to express single chain and full length antibodies in vivo. Due to the limited transgene packaging capacity of AAV, it has been a technical challenge to have a tightly regulated system to express heavy and light chains of an antibody using a single AAV vector in order to generate full length antibodies.

There remains a need in the art for delivering two antibodies in a single composition for therapeutic use.

SUMMARY OF THE INVENTION

A recombinant adeno-associated virus (AAV) having an AAV capsid which has packaged therein a heterologous nucleic acid which expresses two functional antibodies in a cell is provided herein. In one embodiment, the recombinant AAV contains an ORF encoding an immunoglobulin light chain, a second ORF encoding a first immunoglobulin heavy chain and a third ORF encoding a second heavy chain, whereby the expressed functional antibody constructs have two different heavy chains with different specificities which share a light chain. In one embodiment, the two antibodies with different specificities are co-expressed, with a third, bispecific antibody having the specificities of the two monospecific antibodies.

In one embodiment, the rAAV comprises: a 5' AAV inverted terminal repeat (ITR); a first expression cassette which encodes at least a first open reading frame (ORF) for a first immunoglobulin under the control of regulatory control sequences which direct expression thereof; a second expression cassette which comprises a second ORF, a linker, and a third ORF under the control of regulatory control sequences which direct expression thereof, wherein the second and third ORF encode for a second and third immunoglobulin construct; and a 3' AAV ITR.

A pharmaceutical composition is provided which comprises a recombinant AAV which expresses at least two functional antibody constructs and pharmaceutically acceptable carrier. In one embodiment, the at least two functional antibodies have different specificities. Optionally, also co-expressed is a bispecific antibody.

A composition comprising at least two functional antibodies having different specificities is provided, wherein each of the antibodies has the same light chain and a different heavy chain. The light chain is from a different source than the heavy chain for one or both of the antibodies. In one embodiment, two functional monospecific antibodies and a bifunctional antibody are expressed. In one embodiment, the ratio of antibodies is about 25:about 50:about 25, homodimeric:bispecific:homodimeric.

A method of delivering two functional antibodies to a subject is provided which comprises administering a recombinant AAV to the subject.

Still other aspects and advantages of the invention will be readily apparent from the following detailed description of the invention.

BRIEF DESCRIPTION OF THE DRAWINGS

FIG. 3 illustrates the binding ability of an FI6v3k2 antibody co-expressed with a C05 antibody from a recombinant AAV8 prepared as described herein. The results demonstrate the expected binding to full-length HA and the HA stem characteristic of FI6 and binding to HA and HA head only (no stem) characteristic of C05.

FIG. 4A is a bar chart showing binding to protein A captures total monoclonal antibody in the mixture (negative control is represented by the bar on the left, antibody mixture by the bar on the right). FIG. 4B is a graph showing that binding to the TSG101 peptide captures only the MAB containing 1A6 heavy chain (upper line). These data demonstrate that when co-expressed with FI6v3k2, 1A6 antibody retained the binding specificity of antibody from which its heavy chains originated.

FIG. 5 illustrates systemic expression levels in mice administered FI6 co-expressed from an AAV vector with a second antibody at doses of $1\times10^{11}$ genome copies (GC) or $1\times10^{10}$ GC.

FIG. 6A is a line graph showing percent change in weight. The circle represents the AAV9 construct with a bidirectional promoter expressing synthetic FI6v3 and CR8033 monoclonal antibodies having the same heterologous light chain. The square represents a positive control, i.e., AAV9 expressing a single antibody type FI6 also delivered at $1\times10^{11}$ GC, and the triangle represents naïve animals. FIG. 6B shows survival post-challenge.

FIG. 7A is a line graph showing percent change in weight. The circle represents the AAV9 construct with a bidirectional promoter expressing synthetic FI6 and CR8033 monoclonal antibodies having the same heterologous light chain. The square represents a positive control, i.e., AAV9 expressing a single antibody type CR8033 also delivered at $1\times10^{11}$ GC, and the triangle represents naïve animals. FIG. 7B shows survival post-challenge.

FIG. 8A is a chart showing protection in a mouse model following administration of an AAV which expresses both FI6v3 and TCN monoclonal antibodies, as expressed by weight of the mouse over days. The top line (diamonds) represents a dose of 25 micrograms (μg/mL) and the bottom line represents 0.4 μg/mL.

FIG. 8B is a chart showing protection in a mouse model following administration of an AAV which expresses both FI6v3 and IA6 monoclonal antibodies, as expressed by weight of the mouse over days. The top line (diamonds) represents a dose of 263.2 micrograms (μg/mL) and the bottom line represents 36.5 μg/mL.

FIG. 8C is a chart showing protection in a mouse model following administration of an AAV which expresses both FI6v3 and CR8033 monoclonal antibodies, as expressed by weight of the mouse over days. The top line (diamonds) represents a dose of 126.3 micrograms (μg/mL) and the bottom line represents 6.9 μg/mL.

DETAILED DESCRIPTION OF THE INVENTION

Figure 1A:
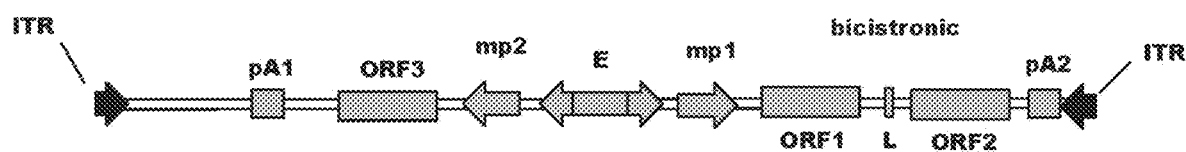
FIG. 1A is a cartoon illustrating an exemplary arrangement for a vector expressing two monospecific antibody constructs containing a first and a second heavy chain and a light chain, which may be from an antibody heterologous to one or both of the antibodies from which the first and second heavy chain originate, and a third, bispecific antibody. This arrangement utilizes a shared enhancer which is bidirectional and which separates a first expression cassette and a second expression cassette. Three open reading frames (ORF) are illustrated. L refers to a linker. pA1 refers to a first polyA and pA2 refers to a second polyA. MP1 refers to a first minimal promoter and MP2 refers to a second minimal promoter. The polyA and the MP may be the same or different for each expression cassette.

A vector is provided herein which delivers at least two functional antibodies by co-expressing two different heavy chains and single light chain which when expressed in a cell form two functional antibodies with different specificities, i.e., which recognize different antigens (or ligands). A third functional antibody may also be expressed and is bispecific, having the heavy chain of each of the two monospecific antibodies. Typically, the third antibody is expressed at a lower level than the two monospecific antibodies. A vector may be used in vivo for efficient production of compositions which will utilize the at least two antibodies or an antibody-producing host cell may be engineered to contain the expression cassettes for the two, different heavy chains and a single type of light chain. Thus, the invention also encompasses a host cell expressing a mixture of two monospecific antibodies, wherein each antibody has a distinct specificity but contains the same light chain, and a third antibody which is bispecific. In one desired embodiment, the vector is designed to deliver the three different antibody constructs in a subject to which the vector is administered.

In one embodiment, the vector is a recombinant AAV which has packaged within an AAV capsid a nucleic acid molecule containing sequences encoding two different heavy chains and a single light chain, which when co-expressed forms two functional monospecific antibodies, i.e., first antibody with a first heavy chain and the light chain and a second antibody with the second heavy chain and the light chain, and a third antibody that has one of each of the heavy chains and the same light chain to make a bispecific antibody.

A "functional antibody" may be an antibody or immunoglobulin which binds to a selected target (e.g., an antigen on a cancer cell or a pathogen, such as a virus, bacteria, or parasite) with sufficient binding affinity to effect a desired physiologic result, which may be protective (e.g., passive immunization) or therapeutic.

The AAV vector provided herein may contain 1, 2, or 3 open reading frames (ORF) for up to ten immunoglobulin domains. As used herein, an "immunoglobulin domain" refers to a domain of an antibody heavy chain or light chain as defined with reference to a conventional, full-length antibody. More particularly, a full-length antibody contains a heavy (H) chain polypeptide which contains four domains: one N-terminal variable (VH) region and three C-terminal constant (CH1, CH2 and CH3) regions and a light (L) chain polypeptide which contains two domains: one N-terminal variable (VL) region and one C-terminal constant (CL) region. An Fc region contains two domains (CH2-CH3). A Fab region may contain one constant and one variable domain for each the heavy and light chains.

In an AAV vector described herein, two full-length heavy chain polypeptides may be expressed (4 domains each) and a light chain polypeptide (two domains). In one desirable embodiment, the two heavy chain polypeptides have different specificities, i.e., are directed to different targets. Thus, the vectors are useful alone or in combination, for expressing mixtures of antibodies.

As used herein, "different specificities" indicates that the referenced immunoglobulin constructs (e.g., a full-length antibody, a heavy chain, or other construct capable of binding a specific target) bind to a different target site. Suitably, in a dual expressed antibody construct, the two specificities are non-overlapping and/or non-interfering, and may optionally enhance each other. Two antibody (immunoglobulin) constructs as described herein confer different specificity by binding to a different target site on the same pathogen or target site (e.g., a virus protein or tumor). Such different target antigens may be different strains of the same viral type (e.g., two different influenza strains), or two different antigens (e.g., an antiviral and anti-cancer, two different anti-cancer constructs, amongst others). For example, a first heavy chain polypeptide may combine with the light chain to form an antibody construct having a first specificity, the second heavy chain polypeptide may combine with the light chain to form a second antibody construct having a second specificity, and the first and second heavy-chain may combine with the light chain to form a bispecific antibody. The antibodies may optionally both be directed to different antigenic sites (epitopes) on a single target (e.g., different target sites on a selected viral, bacterial, fungal or parasite pathogen) or to different targets. For example, heavy chains from the two antibodies may be directed to the influenza virus, and may be co-expressed to form two monospecific antibodies (e.g., heavy chains from influenza viruses FI6, CR8033 and C05 may be selected) and expressed with a selected light chain, and a bispecific antibody. Examples of suitable influenza anitbody and other anti-airborne pathogen antibody constructs and a method for delivering same are described in, e.g., WO 2012/145572A1. The antibodies may also be directed to different targets (e.g., an anti-viral antibody, including chronic viral infections, viral infections associated with cancers, or different anti-neoplastic cell surface proteins or other targets. Examples of suitable viral targets include the influenza hemagglutinin protein or other viral proteins, human immunodeficiency virus (HIV), human papilloma virus (HPV), Epstein-Barr virus, human herpes virus, respiratory syncytial virus, amongst others. Thus, the invention is particularly well suited for use in therapeutics and passive prophylaxis for which combinations of antibodies are desired.

The term "immunoglobulin" is used herein to include antibodies, and functional fragments thereof. Antibodies may exist in a variety of forms including, for example, polyclonal antibodies, monoclonal antibodies, camelized single domain antibodies, intracellular antibodies ("intrabodies"), recombinant antibodies, multispecific antibody (bispecific), antibody fragments, such as, Fv, Fab, F(ab)$_2$, F(ab)$_3$, Fab', Fab'-SH, F(ab')$_2$, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, and the like. "Antibody fragment" refers to at least a portion of the variable region of the immunoglobulin that binds to its target, e.g., the tumor cell. In one embodiment, immunoglobulin is an IgG. However, other types of immunoglobulin may be selected. In another embodiment, the IgG subtype selected is an IgG1. However, other isotypes may be selected. Further, any of the IgG1 allotypes may be selected.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. The term "heterologous light chain" is a light chain containing a variable domain and/or constant domain from an antibody which has a different target specificity from the specificity of the heavy chain.

The two or more ORF(s) carried by the nucleic acid molecule packaged within the vector may be expressed from two expression cassettes, one or both of which may be bicistronic. Because the expression cassettes contain heavy chains from two different antibodies, it is desirable to introduce sequence variation between the two heavy chain sequences to minimize the possibility of homologous recombination. Typically there is sufficient variation between the variable domains of the two antibodies (VH-Ab1 and VH-Ab2). However, it is desirable to ensure there is sufficient coding sequence variation between the constant regions of the first antibody (Ab1) and the second antibody (Ab2), most preferably in each of the CH1, CH2, and CH3 regions. For example, in one embodiment, the heavy chain constant regions of a first antibody may have the sequence of nt 1 to 705 of SEQ ID NO: 1 (which encodes amino acids 1-233 of SEQ ID NO:2) or a sequence which is about 95% to about 99% identical thereto without any introducing any amino acid changes. In one embodiment, variation in the sequence of these regions is introduced in the form of synonymous codons (i.e., variations of the nucleic acid sequence are introduced without any changes at the amino acid level). For example, the second heavy chain may have constant regions which are at least 15%, at least about 25%, at least about 35%, divergent (i.e., about 65% to about 85% identical) over CH1, CH2 and/or CH3.

Once the target and immunoglobulin are selected, the coding sequences for the selected immunoglobulin (e.g., heavy and/or light chain(s)) may be obtained and/or synthesized. Methods for sequencing a nucleic acid (e.g., RNA and DNA) are known to those of skill in the art. Once the sequence of a nucleic acid is known, the amino acid can be deduced and subsequently, there are web-based and commercially available computer programs, as well as service based companies which back translate the amino acids sequences to nucleic acid coding sequences. See, e.g., backtranseq by EMBOSS (www.ebi.ac.uk/Tools/st/); Gene Infinity (www.geneinfinity.org/sms/sms_backtranslation); ExPasy (www.expasy.org/tools/). In one embodiment, the RNA and/or cDNA coding sequences are designed for optimal expression in human cells. Methods for synthesizing nucleic acids are known to those of skill in the art and may be utilized for all, or portions, of the nucleic acid constructs described herein.

Codon-optimized coding regions can be designed by various different methods. This optimization may be performed using methods which are available on-line (e.g., GeneArt), published methods, or a company which provides codon optimizing services, e.g., as DNA2.0 (Menlo Park, Calif.). One codon optimizing algorithm is described, e.g., in WO 2015/012924, which is incorporated by reference herein. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

Optionally, amino acid substitutions may be introduced into a heavy chain constant region in order to increase sequence diversity between the two antibody heavy chains and/or for another purpose. Methods and computer programs for preparing such alignments are available and well known to those of skill in the art. Substitutions may also be written as (amino acid identified by single letter code)-position #-(amino acid identified by single letter code) whereby the first amino acid is the substituted amino acid and the second amino acid is the substituting amino acid at the specified position. The terms "substitution" and "substitution of an amino acid" and "amino acid substitution" as used herein refer to a replacement of an amino acid in an amino acid sequence with another one, wherein the latter is different from the replaced amino acid. Methods for replacing an amino acid are well known to the skilled in the art and include, but are not limited to, mutations of the nucleotide sequence encoding the amino acid sequence. Methods of making amino acid substitutions in IgG are described, e.g., for WO 2013/046704, which is incorporated by reference for its discussion of amino acid modification techniques.

The term "amino acid substitution" and its synonyms described above are intended to encompass modification of an amino acid sequence by replacement of an amino acid with another, substituting amino acid. The substitution may be a conservative substitution. The term conservative, in referring to two amino acids, is intended to mean that the amino acids share a common property recognized by one of skill in the art. The term non-conservative, in referring to two amino acids, is intended to mean that the amino acids which have differences in at least one property recognized by one of skill in the art. For example, such properties may include amino acids having hydrophobic nonacidic side chains, amino acids having hydrophobic side chains (which may be further differentiated as acidic or nonacidic), amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Thus, a conservative amino acid substitution may involve changing a first amino acid having a hydrophobic side chain with a different amino acid having a hydrophobic side chain; whereas a non-conservative amino acid substitution may involve changing a first amino acid with an acidic hydrophobic side chain with a different amino acid having a different side chain, e.g., a basic hydrophobic side chain or a hydrophilic side chain. Still other conservative or non-conservative changes can be determined by one of skill in the art. In still other embodiments, the substitution at a given position will be to an amino acid, or one of a group of amino acids, that will be apparent to one of skill in the art in order to accomplish an objective identified herein.

In order to express a selected immunoglobulin domain, a nucleic acid molecule may be designed which contains codons which have been selected for optimal expression of the immunoglobulin polypeptides in a selected mammalian species, e.g., humans. Further, the nucleic acid molecule may include a heterologous leader sequence for each heavy chain and light chain of the selected antibody, which encodes the wild-type or a mutated IL-2 signal leader peptide fused upstream of the heavy and light chain polypeptides composed of the variable and constant regions. However, another heterologous leader sequence may be substituted for one or both of the IL-2 signal peptide. Signal/leader peptides may be the same or different for each the heavy chain and light chain immunoglobulin constructs. These may be signal sequences which are natively found in an immunoglobulin (e.g., IgG), or may be from a heterologous source. Such heterologous sources may be a cytokine (e.g., IL-2, IL12, IL18, or the like), insulin, albumin, β-glucuronidase, alkaline protease or the fibronectin secretory signal peptides, amongst others.

As used herein, an "expression cassette" refers to a nucleic acid sequence which comprises at least a first open reading frame (ORF) and optionally a second ORF. An ORF may contain two, three, or four antibody domains. For example, the ORF may contain a full-length heavy chain. Alternatively, an ORF may contain one or two antibody domains. For example, the ORF may contain a heavy chain variable domain and a single heavy chain constant domain. In another example, the ORF may contain a light chain variable and a light chain constant region. Thus, an expression cassette may be designed to be bicistronic, i.e., to contain regulatory sequences which direct expression of the ORFs thereon from shared regulatory sequences. In this instance, the two ORFs are typically separated by a linker. Suitable linkers, such as an internal ribozyme binding site (IRES) and/or a furin-2a self-cleaving peptide linker (F2a), [see, e.g., Radcliffe and Mitrophanous, Gene Therapy (2004), 11, 1673-1674] are known in the art. Suitably, the ORF are operably linked to regulatory control sequences which direct expression in a target cell. Such regulatory control sequences may include a polyA, a promoter, and an enhancer. In order to facilitate co-expression from an AAV vector, at least one of the enhancer and/or polyA sequence may be shared by the first and second expression cassettes.

In one embodiment, the rAAV has packaged within the selected AAV capsid, a nucleic acid molecule comprising: a 5' ITR, a first expression cassette, a bidirectional enhancer, and a second expression cassette, where the bidirectional enhancer separates the first and second expression cassettes, and a 3' ITR. FIG. 1A is provided herein as an example of this embodiment. For example, in such an embodiment, a first promoter for a first expression cassette is located to the left of the bidirectional enhancer, followed by at least a first open reading frame, and a polyA sequence, and a second promoter. Further, a second promoter for the second expression cassette is located to the right of the bidirectional enhancer, followed by at least a second open reading frame and a polyA. The first and second promoters and the first and second polyA sequences may be the same or different. A minimal promoter and/or a minimal polyA may be selected in order to conserve space. Typically, in this embodiment, each promoter is located adjacent (either to the left or the right (or 5' or 3')) to the enhancer sequence and the polyA sequences are located adjacent to the ITRs, with the ORFs there between. While FIG. 1A is illustrative, the order of the ORFs may be varied, as may the immunoglobulin domains encoded thereby. For example, the light chain constant and variable sequences may be located to the left of the enhancer and the two heavy chains may be encoded by ORFs located to the right of the enhancer. Alternatively, one of the heavy chains may be located to the left of the enhancer and the ORFs to the right of the enhancer by encode a second heavy chain and a light chain. Alternatively, the opposite configuration is possible, and the expression cassette to the left of the enhancer may be bicistronic. Alternatively, depending upon what domains are encoded, both expression cassettes may be monocistronic (e.g., encoding two immunoadhesins), or both can be bicistronic (e.g., encoding two complete FABs).

Figure 1B:
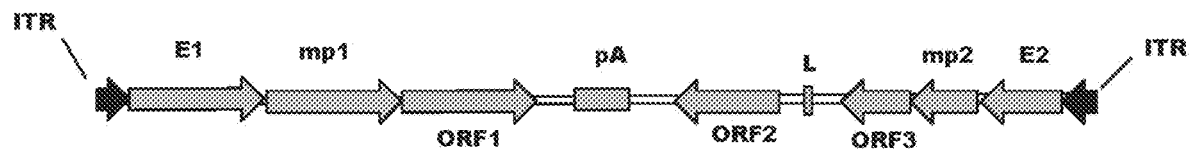
FIG. 1B is a cartoon illustrating an alternative exemplary arrangement for a vector expressing two antibody constructs containing a first and a second heavy chain and a light chain, which may be from an antibody heterologous to one or both of the antibodies from which the first and second heavy chain originate, and a third, bispecific antibody. This arrangement utilizes a shared polyA. E1 refers to a first enhancer and E2 refers to a second enhancer. These may be same or different enhancers for each of the expression cassettes. Similarly MP1 and MP2 may the same or different.

In another embodiment, the rAAV has packaged within the selected AAV capsid, a nucleic acid molecule comprising: a 5' ITR, a first expression cassette, a polyA which functions bidirectionally, and a second expression cassette, where the bidirectional polyA separates and functions for both the first and the second expression cassettes, and a 3' ITR. FIG. 1B is provided herein as an example of this embodiment. In this embodiment, a first enhancer and a first promoter (or enhancer/promoter combination) is located to the right of the 5' ITR, followed by the ORF(s) and the bidirectional polyA. The second expression cassette is separated from the first expression cassette by the bidirectional polyA and is transcribed in the opposite orientation. In this expression cassette, the enhancer and promoter (or promoter/enhancer combination) is located adjacent to the 3' ITR and the ORF(s) are adjacent to the bidirectional polyA. While FIG. 1B is illustrative, the order of the ORFs may be varied, as may the immunoglobulin domains encoded thereby. For example, the light chain constant and variable sequences may be located to the left of the polyA and the two heavy chains may be encoded by ORF(s) located to the right of the polyA. Alternatively, one of the heavy chains may be located to the left of the polyA and the ORFs to the right of the polyA encode a second heavy chain and a light chain. Alternatively, the opposite configuration is possible, and the expression cassette to the left of the polyA may be bicistronic. Alternatively, depending upon what domains are encoded, both expression cassettes may be monocistronic (e.g., encoding two immunoadhesins), or both can be bicistronic.

Optionally, the expression configuration exemplified in FIGS. 1A and 1B and described herein may be used to co-express other immunoglobulin constructs. For example, two immunoadhesins (IA) may be expressed from two monocistronic expression cassettes. An immunoadhesin includes a form of antibody that is expressed as single open reading frame containing a single chain variable fragment (scFv) unit (i.e., VH linked to VL or VL linked to VH) fused to an Fc domain (CH2-CH3), (e.g., VH-VL-CH2-CH3 or VL-VH-CH2-CH3). Alternatively, up to four scFvs could be expressed from two bicistronic expression cassettes. In another alternative, an IA may be co-expressed with a full-length antibody. In another alternative, one complete FABS may be co-expressed with a full-length antibody or two complete FABs may be co-expressed. In still another embodiment, other combinations of full-length antibody, IA, or FAB fragment may be co-expressed.

Suitable regulatory control sequences may be selected and obtained from a variety of sources. In one embodiment, a minimal promoter and/or a minimal polyA may be utilized to conserve size.

As used herein, the term "minimal promoter" means a short DNA sequence comprised of a TATA-box and other sequences that serve to specify the site of transcription initiation, to which regulatory elements are added for control of expression. In one embodiment, a promoter refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. In one embodiment, the minimal promoter is a Cytomegalovirus (CMV) minimal promoter. In another embodiment, the minimal promoter is derived from human CMV (hCMV) such as the hCMV immediate early promoter derived minimal promoter (see, US 20140127749, and Gossen and Bujard (Proc. Natl. Acad. Sci. USA, 1992, 89: 5547-5551), which are incorporated herein by reference). In another embodiment, the minimal promoter is derived from a viral source such as, for example: SV40 early or late promoters, cytomegalovirus (CMV) immediate early promoters, or Rous Sarcoma Virus (RSV) early promoters; or from eukaryotic cell promoters, for example, beta actin promoter (Ng, Nuc. Acid Res. 17:601-615, 1989; Quitsche et al., J. Biol. Chem. 264:9539-9545, 1989), GADPH promoter (Alexander, M. C. et al., Proc. Nat. Acad. Sci. USA 85:5092-5096, 1988, Ercolani, L. et al., J. Biol. Chem. 263:15335-15341, 1988), TK-1 (thymidine kinase) promoter, HSP (heat shock protein) promoters, UbB or UbC promoter, PGK, Ef1-alpha promoter or any eukaryotic promoter containing a TATA box (US Published Application No. 2014/0094392). In another embodiment, the minimal promoter includes a mini-promoter, such as the CLDN5 mini-promoter described in US Published Application No. 2014/0065666. In another embodiment, the minimal promoter is the Thymidine Kinase (TK) promoter. In one embodiment, the minimal promoter is tissue specific, such as one of the muscle-cell specific promoters, minimal TnISlow promoter, a minimal TnIFast promoter or a muscle creatine kinase promoter (US Published Application No. 2012/0282695). Each of these documents is incorporated herein by reference.

In one embodiment, the polyadenylation (poly(A)) signal is a minimal poly(A) signal, i.e., the minimum sequence required for efficient polyadenylation. In one embodiment, the minimal poly(A) is a synthetic poly(A), such as that described in Levitt et al, Genes Dev., 1989 July, 3(7):1019-25; and Xia et al, Nat Biotechnol. 2002 October; 20(10): 1006-10. Epub 2002 Sep. 16. In another embodiment, the poly(A) is derived from the rabbit beta-globin poly(A). In one embodiment, the polyA acts bidirectionally (An et al, 2006, PNAS, 103(49): 18662-18667). In one embodiment, the poly(A) is derived from the SV40 early poly A signal sequence. Each of these documents is incorporated herein by reference.

As described herein, in one embodiment, a single enhancer, or the same enhancer, may regulate the transcription of multiple heterologous genes in the plasmid construct. Various enhancers suitable for use in the invention are known in the art and include, for example, the CMV early enhancer, Hoxc8 enhancer, nPE1 and nPE2. Additional enhancers useful herein are described in Andersson et al, Nature, 2014 March, 507(7493):455-61, which is incorporated herein by reference. Still other enhancer elements may include, e.g., an apolipoprotein enhancer, a zebrafish enhancer, a GFAP enhancer element, and tissue specific enhancers such as described in WO 2013/1555222, woodchuck hepatitis post-transcriptional regulatory element. Additionally, or alternatively, other, e.g., the hybrid human cytomegalovirus (HCMV)-immediate early (IE)-PDGR promoter or other promoter-enhancer elements may be selected. To enhance expression the other elements can be introns (like promega intron or chimeric chicken globin-human immunoglobulin intron). Other promoters and enhancers useful herein can be found in the Mammalian Promoter/Enhancer Database found at promoter.cdb.riken.jp/.

The constructs described herein may further contain other expression control or regulatory sequences such as, e.g., include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A promoter may be selected from amongst a constitutive promoter, a tissue-specific promoter, a cell-specific promoter, a promoter responsive to physiologic cues, or an regulatable promoter [see, e.g., WO 2011/126868 and WO 2013/049492].

These control sequences are "operably linked" to the immunoglobulin construct gene sequences. As used herein, the term "operably linked" refers to both expression control sequences that are contiguous with the gene of interest and expression control sequences that act in trans or at a distance to control the gene of interest.

Examples of constitutive promoters suitable for controlling expression of the antibody domains include, but are not limited to chicken β-actin (CB) or beta actin promoters from other species, human cytomegalovirus (CMV) promoter, the early and late promoters of simian virus 40 (SV40), U6 promoter, metallothionein promoters, EF1α promoter, ubiquitin promoter, hypoxanthine phosphoribosyl transferase (HPRT) promoter, dihydrofolate reductase (DHFR) promoter (Scharfmann et al., Proc. Natl. Acad. Sci. USA 88:4626-4630 (1991)), adenosine deaminase promoter, phosphoglycerol kinase (PGK) promoter, pyruvate kinase promoter phosphoglycerol mutase promoter, the β-actin promoter (Lai et al., Proc. Natl. Acad. Sci. USA 86: 10006-10010 (1989)), UbB, UbC, the long terminal repeats (LTR) of Moloney Leukemia Virus and other retroviruses, the thymidine kinase promoter of Herpes Simplex Virus and other constitutive promoters known to those of skill in the art. Examples of tissue- or cell-specific promoters suitable for use in the present invention include, but are not limited to, endothelin-I (ET-I) and Flt-I, which are specific for endothelial cells, FoxJ1 (that targets ciliated cells).

Inducible promoters suitable for controlling expression of the antibody domains include promoters responsive to exogenous agents (e.g., pharmacological agents) or to physiological cues. These response elements include, but are not limited to a hypoxia response element (HRE) that binds HIF-Iα and β, a metal-ion response element such as described by Mayo et al. (1982, Cell 29:99-108); Brinster et al. (1982, Nature 296:39-42) and Searle et al. (1985, Mol. Cell. Biol. 5:1480-1489); or a heat shock response element such as described by Nouer et al. (in: Heat Shock Response, ed. Nouer, L., CRC, Boca Raton, Fla., ppI67-220, 1991).

In one embodiment, expression of an open reading frame is controlled by a regulatable promoter that provides tight control over the transcription of the ORF (gene), e.g., a pharmacological agent, or transcription factors activated by a pharmacological agent or in alternative embodiments, physiological cues. Examples of regulatable promoters which are ligand-dependent transcription factor complexes that may be used include, without limitation, members of the nuclear receptor superfamily activated by their respective ligands (e.g., glucocorticoid, estrogen, progestin, retinoid, ecdysone, and analogs and mimetics thereof) and rTTA activated by tetracycline. Examples of such systems, include, without limitation, the ARGENT™ Transcriptional Technology (ARIAD Pharmaceuticals, Cambridge, Mass.). Examples of such promoter systems are described, e.g., in WO 2012/145572, which is incorporated by reference herein.

Still other promoters may include, e.g., human cytomegalovirus (CMV) immediate-early enhancer/promoter, the SV40 early enhancer/promoter, the JC polymavirus promoter, myelin basic protein (MBP) or glial fibrillary acidic protein (GFAP) promoters, herpes simplex virus (HSV-1) latency associated promoter (LAP), rouse sarcoma virus (RSV) long terminal repeat (LTR) promoter, neuron-specific promoter (NSE), platelet derived growth factor (PDGF) promoter, hSYN, melanin-concentrating hormone (MCH) promoter, CBA, matrix metalloprotein promoter (MPP), and the chicken beta-actin promoter. The promoters may the same or different for each expression cassette.

For use in producing an AAV viral vector (e.g., a recombinant (r) AAV), the expression cassettes can be carried on any suitable vector, e.g., a plasmid, which is delivered to a packaging host cell. The plasmids useful in this invention may be engineered such that they are suitable for replication and packaging in prokaryotic cells, mammalian cells, or both. Suitable transfection techniques and packaging host cells are known and/or can be readily designed by one of skill in the art.

Methods for generating and isolating AAVs suitable for use as vectors are known in the art. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. For packaging a transgene into virions, the ITRs are the only AAV components required in cis in the same construct as the nucleic acid molecule containing the expression cassettes. The cap and rep genes can be supplied in trans.

As described above, the term "about" when used to modify a numerical value means a variation of ±10%, unless otherwise specified.

As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of the modified ORFs provided herein) when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

In one embodiment, the expression cassettes described herein are engineered into a genetic element (e.g., a shuttle plasmid) which transfers the immunoglobulin construct sequences carried thereon into a packaging host cell for production a viral vector. In one embodiment, the selected genetic element may be delivered to a an AAV packaging cell by any suitable method, including transfection, electroporation, liposome delivery, membrane fusion techniques, high velocity DNA-coated pellets, viral infection and protoplast fusion. Stable AAV packaging cells can also be made. Alternatively, the expression cassettes may be used to generate a viral vector other than AAV, or for production of mixtures of antibodies in vitro. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, N.Y. (2012).

AAV Vectors

A recombinant AAV vector (AAV viral particle) may comprise, packaged within an AAV capsid, a nucleic acid molecule containing a 5' AAV ITR, the expression cassettes described herein and a 3' AAV ITR. As described herein, an expression cassette may contain regulatory elements for an open reading frame(s) within each expression cassette and the nucleic acid molecule may optionally contain additional regulatory elements.

The AAV vector may contain a full-length AAV 5' inverted terminal repeat (ITR) and a full-length 3' ITR. A shortened version of the 5' ITR, termed ΔITR, has been described in which the D-sequence and terminal resolution site (trs) are deleted. The abbreviation "sc" refers to self-complementary. "Self-complementary AAV" refers to a construct in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

Where a pseudotyped AAV is to be produced, the ITRs are selected from a source which differs from the AAV source of the capsid. For example, AAV2 ITRs may be selected for use with an AAV capsid having a particular efficiency for a selected cellular receptor, target tissue or viral target. In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. However, other sources of AAV ITRs may be utilized.

A variety of AAV capsids have been described. Methods of generating AAV vectors have been described extensively in the literature and patent documents, including, e.g., WO 2003/042397; WO 2005/033321, WO 2006/110689; U.S. Pat. No. 7,588,772 B2. The source of AAV capsids may be selected from an AAV which targets a desired tissue. For example, suitable AAV may include, e.g., AAV9 [U.S. Pat. No. 7,906,111; US 2011-0236353-A1], rh10 [WO 2003/042397] and/or hu37 [see, e.g., U.S. Pat. No. 7,906,111; US 2011-0236353-A1]. However, other AAV, including, e.g., AAV1, AAV2, AAV3, AAV4, AAV5, AAV6, AAV7, AAV8, [U.S. Pat. Nos. 7,790,449; 7,282,199] and others. However, other sources of AAV capsids and other viral elements may be selected, as may other immunoglobulin constructs and other vector elements.

A single-stranded AAV viral vector is provided. Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus ULS, ULB, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065.

Uses and Regimens

The rAAV, preferably suspended in a physiologically compatible carrier, may be administered to a human or non-human mammalian patient. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, maltose, and water. The selection of the carrier is not a limitation of the present invention. Optionally, the compositions of the invention may contain, in addition to the rAAV and carrier(s), other conventional pharmaceutical ingredients, such as preservatives, or chemical stabilizers.

Methods for using these rAAV, e.g., for passive immunization are described, e.g., in WO 2012/145572. Other methods of delivery and uses will be apparent to one of skill in the art. For example, a regimen as described herein may comprise, in addition to one or more of the combinations described herein, further combination with one or more of a biological drug, a small molecule drug, a chemotherapeutic agent, immune enhancers, radiation, surgery, and the like. A biological drug as described herein, is based on a peptide, polypeptide, protein, enzyme, nucleic acid molecule, vector (including viral vectors), or the like.

In a combination therapy, the AAV-delivered immunoglobulin construct described herein is administered before, during, or after commencing therapy with another agent, as well as any combination thereof, i.e., before and during, before and after, during and after, or before, during and after commencing the therapy. For example, the AAV can be administered between 1 and 30 days, preferably 3 and 20 days, more preferably between 5 and 12 days before commencing radiation therapy. In another embodiment of the invention, chemotherapy is administered concurrently with or, more preferably, subsequent to AAV-mediated immunoglobulin (antibody) therapy. In still other embodiments, the compositions of the invention may be combined with other biologics, e.g., recombinant monoclonal antibody drugs, antibody-drug conjugates, or the like. Further, combinations of different AAV-delivered immunoglobulin constructs such as are discussed above may be used in such regimens.

Any suitable method or route can be used to administer AAV-containing compositions as described herein, and optionally, to co-administer other active drugs or therapies in conjunction with the AAV-mediated antibodies described herein. Routes of administration include, for example, systemic, oral, intravenous, intraperitoneal, subcutaneous, or intramuscular administration.

Targets for the immunoglobulin constructs described herein may be selected from a variety of pathogens, including, e.g., bacterial, viral, fungal and parasitic infectious agents. Suitable targets may further include cancer or cancer-associated antigens, or the like. Still other targets may include an autoimmune condition such as rheumatoid arthritis (RA) or multiple sclerosis (MS).

Examples of viral targets include influenza virus from the orthomyxovirudae family, which includes: Influenza A, Influenza B, and Influenza C. The type A viruses are the most virulent human pathogens. The serotypes of influenza A which have been associated with pandemics include, H1N1, which caused Spanish Flu in 1918, and Swine Flu in 2009; H2N2, which caused Asian Flu in 1957; H3N2, which caused Hong Kong Flu in 1968; H5N1, which caused Bird Flu in 2004; H7N7; H1N2; H9N2; H7N2; H7N3; and H10N7.

Broadly neutralizing antibodies against influenza A have been described. As used herein, a "broadly neutralizing antibody" refers to a neutralizing antibody which can neutralize multiple strains from multiple subtypes. For example, CR6261 [The Scripps Institute/Crucell] has been described as a monoclonal antibody that binds to a broad range of the influenza virus including the 1918 "Spanish flu" (SC1918/H1) and to a virus of the H5N1 class of avian influenza that jumped from chickens to a human in Vietnam in 2004 (Viet04/H5). CR6261 recognizes a highly conserved helical region in the membrane-proximal stem of hemagglutinin, the predominant protein on the surface of the influenza virus. This antibody is described in WO 2010/130636, incorporated by reference herein. Another neutralizing antibody, F10 [XOMA Ltd] has been described as being useful against H1N1 and H5N1. [Sui et al, Nature Structural and Molecular Biology (Sui, et al. 2009, 16(3):265-73)] Other antibodies against influenza, e.g., Fab28 and Fab49, may be selected. See, e.g., WO 2010/140114 and WO 2009/115972, which are incorporated by reference. Still other antibodies, such as those described in WO 2010/010466, US Published Patent Publication US/2011/076265, and WO 2008/156763, may be readily selected.

Other target pathogenic viruses include, arenaviruses (including funin, machupo, and Lassa), filoviruses (including Marburg and Ebola), hantaviruses, picornaviridae (including rhinoviruses, echovirus), coronaviruses, paramyxovirus, morbillivirus, respiratory syncytial virus, togavirus, coxsackievirus, parvovirus B19, parainfluenza, adenoviruses, reoviruses, variola (Variola major (Smallpox)) and Vaccinia (Cowpox) from the poxvirus family, and varicella-zoster (pseudorabies).

Viral hemorrhagic fevers are caused by members of the arenavirus family (Lassa fever) (which family is also associated with Lymphocytic choriomeningitis (LCM)), filovirus (ebola virus), and hantavirus (puremala). The members of picornavirus (a subfamily of rhinoviruses), are associated with the common cold in humans. The coronavirus family includes a number of non-human viruses such as infectious bronchitis virus (poultry), porcine transmissible gastroenteric virus (pig), porcine hemagglutinatin encephalomyelitis virus (pig), feline infectious peritonitis virus (cat), feline enteric coronavirus (cat), canine coronavirus (dog). The human respiratory coronaviruses, have been putatively associated with the common cold, non-A, B or C hepatitis, and sudden acute respiratory syndrome (SARS). The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus (RSV). The parvovirus family includes feline parvovirus (feline enteritis), feline panleucopeniavirus, canine parvovirus, and porcine parvovirus. The adenovirus family includes viruses (EX, AD7, ARD, O.B.) which cause respiratory disease.

A neutralizing antibody construct against a bacterial pathogen may also be selected for use in the present invention. In one embodiment, the neutralizing antibody construct is directed against the bacteria itself. In another embodiment, the neutralizing antibody construct is directed against a toxin produced by the bacteria. Examples of airborne bacterial pathogens include, e.g., *Neisseria meningitidis* (meningitis), *Klebsiella pneumonia* (pneumonia), *Pseudomonas aeruginosa* (pneumonia), *Pseudomonas pseudomallei* (pneumonia), *Pseudomonas mallei* (pneumonia), *Acinetobacter* (pneumonia), *Moraxella catarrhalis, Moraxella lacunata, Alkaligenes, Cardiobacterium, Haemophilus influenzae* (flu), *Haemophilus parainfluenzae, Bordetella pertussis* (whooping cough), *Francisella tularensis* (pneumonia/fever), *Legionella pneumonia* (Legionnaires disease), *Chlamydia psittaci* (pneumonia), *Chlamydia pneumoniae* (pneumonia), *Mycobacterium tuberculosis* (tuberculosis (TB)), *Mycobacterium kansasii* (TB), *Mycobacterium avium* (pneumonia), *Nocardia asteroides* (pneumonia), *Bacillus anthracis* (anthrax), *Staphylococcus aureus* (pneumonia), *Streptococcus pyogenes* (scarlet fever), *Streptococcus pneumoniae* (pneumonia), *Corynebacteria diphtheria* (diphtheria), *Mycoplasma pneumoniae* (pneumonia).

The causative agent of anthrax is a toxin produced by *Bacillus anthracis*. Neutralizing antibodies against protective agent (PA), one of the three peptides which form the toxoid, have been described. The other two polypeptides consist of lethal factor (LF) and edema factor (EF). Anti-PA neutralizing antibodies have been described as being effective in passively immunization against anthrax. See, e.g., U.S. Pat. No. 7,442,373; R. Sawada-Hirai et al, J Immune Based Ther Vaccines. 2004; 2: 5. (on-line 2004 May 12). Still other anti-anthrax toxin neutralizing antibodies have been described and/or may be generated. Similarly, neutralizing antibodies against other bacteria and/or bacterial toxins may be used to generate an AAV-delivered anti-pathogen construct as described herein.

Other infectious diseases may be caused by airborne fungi including, e.g., *Aspergillus* species, *Absidia corymbifera, Rhixpus stolonifer, Mucor plumbeaus, Cryptococcus neoformans, Histoplasm capsulatum, Blastomyces dermatitidis, Coccidioides immitis, Penicillium* species, *Micropolyspora faeni, Thermoactinomyces vulgaris, Alternaria alternate, Cladosporium* species, *Helminthosporium*, and *Stachybotrys* species.

In addition, passive immunization may be used to prevent fungal infections (e.g., athlete's foot), ringworm, or viruses, bacteria, parasites, fungi, and other pathogens which can be transmitted by direct contact. In addition, a variety of conditions which affect household pets, cattle and other livestock, and other animals. For example, in dogs, infection of the upper respiratory tract by canine sinonasal aspergillosis causes significant disease. In cats, upper respiratory disease or feline respiratory disease complex originating in the nose causes morbidity and mortality if left untreated. Cattle are prone to infections by the infectious bovine rhinotracheitis (commonly called IBR or red nose) is an acute, contagious virus disease of cattle. In addition, cattle are prone to Bovine Respiratory Syncytial Virus (BRSV) which causes mild to severe respiratory disease and can impair resistance to other diseases. Still other pathogens and diseases will be apparent to one of skill in the art. See, e.g., U.S. Pat. No. 5,811,524, which describes generation of anti-respiratory syncytial virus (RSV) neutralizing antibodies. The techniques described therein are applicable to other pathogens. Such an antibody may be used intact or its sequences (scaffold) modified to generate an artificial or recombinant neutralizing antibody construct. Such methods have been described [see, e.g., WO 2010/13036; WO 2009/115972; WO 2010/140114].

Anti-neoplastic immunoglobulins as described herein may target a human epidermal growth factor receptor (HER), such as HER2. For example, trastuzumab is a recombinant IgG1 kappa, humanized monoclonal antibody that selectively binds with high affinity in a cell-based assay (Kd=5 nM) to the extracellular domain of the human epidermal growth factor receptor protein. The commercially available product is produced in CHO cell culture. See, e.g., DrugBank online database. The amino acid sequences of the trastuzumab light chains 1 and 2 and heavy chains 1 and 2, as well as sequences obtained from a study of the x-ray structure of trastuzumab, are provided on this database at accession number DB00072, which sequences are incorporated herein by reference. See, also, 212-Pb-TCMC-trastuzumab [Areva Med, Bethesda, Md.]. Another antibody of interest includes, e.g., pertuzumab, a recombinant humanized monoclonal antibody that targets the extracellular dimerization domain (Subdomain II) of the human epidermal growth factor receptor 2 protein (HER2). It consists of two heavy chains and two lights chains that have 448 and 214 residues respectively. FDA approved Jun. 8, 2012. The amino acid sequences of its heavy chain and light chain are provided, e.g., in DrugBank online database at accession number DB06366. In addition to HER2, other HER targets may be selected.

For example, MM-121/SAR256212 is a fully human monoclonal antibody that targets the HER3 receptor [Merrimack's Network Biology] and which has been reported to be useful in the treatment of non-small cell lung cancer (NSCLC), breast cancer and ovarian cancer. SAR256212 is an investigational fully human monoclonal antibody that targets the HER3 (ErbB3) receptor [Sanofi Oncology]. Another anti-Her3/EGFR antibody is RG7597 [Genentech], described as being useful in head and neck cancers. Another antibody, margetuximab (or MGAH22), a next-generation, Fc-optimized monoclonal antibody (mAb) that targets HER [MacroGenics], may also be utilized.

Alternatively, other human epithelial cell surface markers and/or other tumor receptors or antigens may be targeted. Examples of other cell surface marker targets include, e.g., 5T4, CA-125, CEA (e.g., targeted by labetuzumab), CD3, CD19, CD20 (e.g., targeted by rituximab), CD22 (e.g., targeted by epratuzumab or veltuzumab), CD30, CD33, CD40, CD44, CD51 (also integrin $\alpha_v\beta_3$), CD133 (e.g., glioblastoma cells), CTLA-4 (e.g., Ipilimumab used in treatment of, e.g., neuroblastoma)), Chemokine (C-X-C Motif) Receptor 2 (CXCR2) (expressed in different regions in brain; e.g., Anti-CXCR2 (extracellular) antibody #ACR-012 (Alomene Labs)); EpCAM, fibroblast activation protein (FAP) [see, e.g., WO 2012020006 A2, brain cancers], folate receptor alpha (e.g., pediatric ependymal brain tumors, head and neck cancers), fibroblast growth factor receptor 1 (FGFR1) (see, et al, WO2012125124A1 for discussion treatment of cancers with anti-FGFR1 antibodies), FGFR2 (see, e.g., antibodies described in WO2013076186A and WO2011143318A2), FGFR3 (see, e.g., antibodies described in U.S. Pat. No. 8,187,601 and WO2010111367A1), FGFR4 (see, e.g., anti-FGFR4 antibodies described in WO2012138975A1), hepatocyte growth factor (HGF) (see, e.g., antibodies in WO2010119991A3), integrin $\alpha_5\beta_1$, IGF-1 receptor, gangioloside GD2 (see, e.g., antibodies described in WO2011160119A2), ganglioside GD3, transmembrane glycoprotein NMB (GPNMB) (associated with gliomas, among others and target of the antibody glembatumumab (CR011), mucin, MUC1, phosphatidylserine (e.g., targeted by bavituximab, Peregrine Pharmaceuticals, Inc], prostatic carcinoma cells, PD-L1 (e.g., nivolumab (BMS-936558, MDX-1106, ONO-4538), a fully human gG4, e.g., metastatic melanoma], platelet-derived growth factor receptor, alpha (PDGFR $\alpha$) or CD140, tumor associated glycoprotein 72 (TAG-72), tenascin C, tumor necrosis factor (TNF) receptor (TRAIL-R2), vascular endothelial growth factor (VEGF)-A (e.g., targeted by bevacizumab) and VEGFR2 (e.g., targeted by ramucirumab).

Other antibodies and their targets include, e.g., APN301 (hu14.19-IL2), a monoclonal antibody [malignant melanoma and neuroblastoma in children, Apeiron Biolgics, Vienna, Austria]. See, also, e.g., monoclonal antibody, 8H9, which has been described as being useful for the treatment of solid tumors, including metastatic brain cancer. The monoclonal antibody 8H9 is a mouse IgG1 antibody with specificity for the B7H3 antigen [United Therapeutics Corporation]. This mouse antibody can be humanized. Still other immunoglobulin constructs targeting the B7-H3 and/or the B7-H4 antigen may be used in the invention. Another antibody is S58 (anti-GD2, neuroblastoma). Cotara™ [Perregrince Pharmaceuticals] is a monoclonal antibody described for treatment of recurrent glioblastoma. Other antibodies may include, e.g., avastin, ficlatuzumab, medi-575, and olaratumab. Still other immunoglobulin constructs or monoclonal antibodies may be selected for use in the invention. See, e.g., Medicines in Development Biologics, 2013 Report, pp. 1-87, a publication of PhRMA's Communications & Public Affairs Depaitment. (202)835-3460, which is incorporated by reference herein.

For example, immunogens may be selected from a variety of viral families. Example of viral families against which an immune response would be desirable include, the picornavirus family, which includes the genera *rhinoviruses*, which are responsible for about 50% of cases of the common cold; the genera *enteroviruses*, which include polioviruses, coxsackieviruses, echoviruses, and human *enteroviruses* such as hepatitis A virus; and the genera *apthoviruses*, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera *alphavirus*, which include Sindbis viruses, RossRiver virus, and Venezuelan, Eastern & Western Equine encephalitis, and *rubivirus*, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera *vesiculovirus* (e.g., Vesicular Stomatitis Virus), and the general lyssavirus (e.g., rabies).

Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera *bunyavirus* (California encephalitis, La Crosse), *phlebovirus* (Rift Valley Fever), *hantavirus* (puremala is a hemahagin fever virus), *nairovirus* (Nairobi sheep disease) and various unassigned *bunyaviruses*. The arenavirus family provides a source of antigens against LCM and Lassa fever virus. The reovirus family includes the genera *reovirus, rotavirus* (which causes acute gastroenteritis in children), *orbiviruses*, and *cultivirus* (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected as targets. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. Nos. 5,891,994 and 6,193,981.] See, also, the HIV and SIV proteins described in D. H. Barouch et al, J. Virol., 75(5):2462-2467 (March 2001), and R. R. Amara, et al, *Science,* 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins has been described or could readily be made by one of skill in the art. See, e.g., the modified gag protein that is described in U.S. Pat. No. 5,972,596.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family includes feline parvovirus (feline enteritis), feline panleucopeniavirus, canine parvovirus, and porcine parvovirus. The herpesvirus family includes the sub-family alphaherpesvirinae, which encompasses the genera *simplexvirus* (HSVI, HSVII), *varicellovirus* (pseudorabies, varicella zoster) and the sub-family betaherpesvirinae, which includes the genera *cytomegalovirus* (HCMV, muromegalovirus) and the sub-family gammaherpesvirinae, which includes the genera *lymphocryptovirus*, EBV (Burkitts lymphoma), infectious rhinotracheitis, Marek's disease virus, and rhadinovirus. The poxvirus family includes the sub-family chordopoxvirinae, which encompasses the genera *orthopoxvirus* (Variola (Smallpox) and Vaccinia (Cowpox)), *parapoxvirus, avipoxvirus, capripoxvirus, leporipoxvirus, suipoxvirus*, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

Other pathogenic targets for antibodies may include, e.g., bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include enterobacteriaceae; pseudomonas, acinetobacteria and eikenella; melioidosis; salmonella; shigella; haemophilus; moraxella; *H. ducreyi* (which causes chancroid); *brucella; Franisella tularensis* (which causes tularemia); yersinia (pasteurella); streptobacillus moniliformis and spirillum; Gram-positive bacilli include *Listeria monocytogenes*; erysipelothrix rhusiopathiae; *Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: *Mycoplasma pneumoniae*; lymphogranuloma venereum; psittacosis; and perinatal chlamydial infections. Pathogenic eukaryotes encompass pathogenic protozoa and helminthes and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Depaitment of Health and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae*, *Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to target antigens from these organisms, viruses, their toxins or other by-products, which will prevent and/or treat infection or other adverse reactions with these biological agents.

The following examples are illustrative only and are not a limitation on the invention described herein.

Example 1: Generation of Vectors Containing Full-Length Antibody Co-Expression Cassettes A series of cis-plasmids were prepared for use in generating an AAV viral particle containing a nucleic acid molecule for delivery to a host target cell. The nucleic acid molecules comprise AAV2 5' and 3' ITR sequences at each terminus, a shared CMV enhancer flanked by two expression cassettes in opposite orientations, where a first expression cassette is controlled by a first minimal CMV promoter and a second expression cassette is controlled by a second minimal CMV promoter. All sequences located between AAV2 ITRs were de novo synthesized by a commercial vendor (GeneArt). All coding sequences for immunoglobulin variable domains were flanked with the unique restriction enzymes to allow convenient shuttling of the desired variable domains. To create constructs with heterologous light chain sequence (kgl), a coding sequence encoding germline light chain (IGKV4-1*01) was de novo synthesized and used to replace FI6 variable light sequence.

Figure 2:
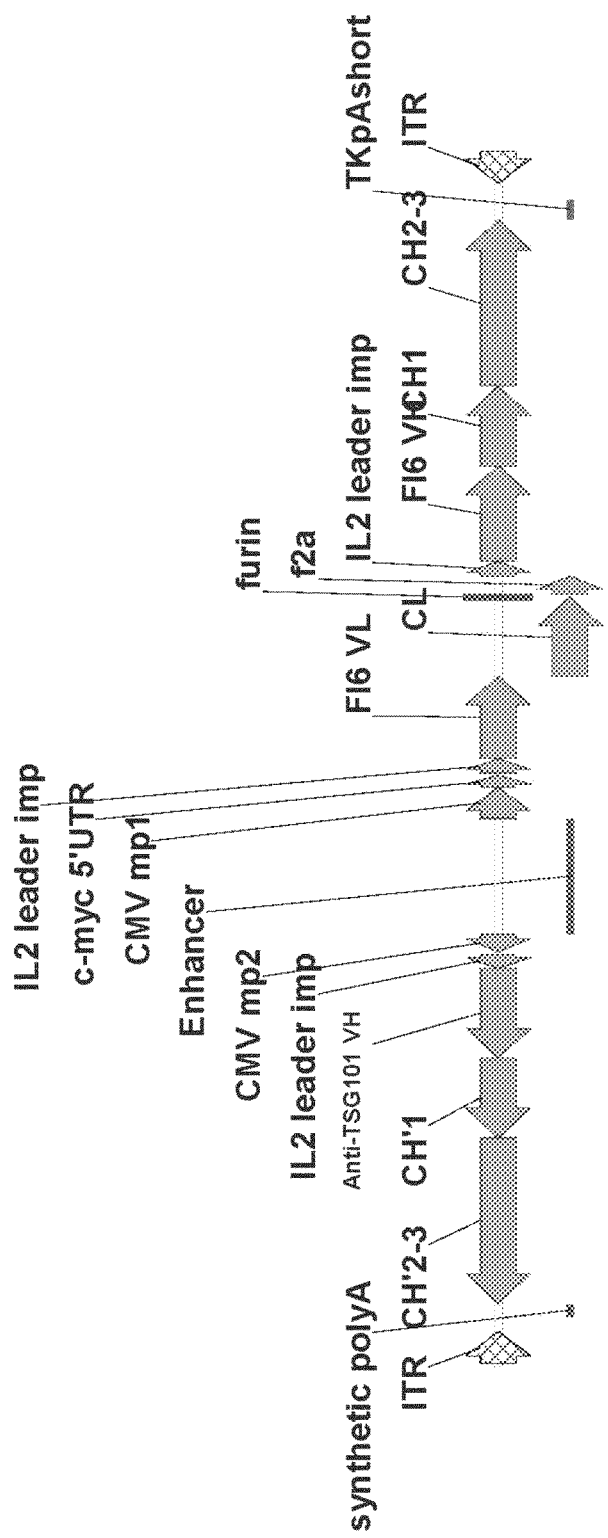
FIG. 2 illustrates a nucleic acid molecule carried by a plasmid for packaging into an AAV capsid, which is used for co-expression of an anti-TSG 101 heavy chain, FI6 influenza heavy chain, and FI6 light chain. These antibody chains utilize heterologous leader from interleukin 2 (IL2). The human CMV enhancer was used in conjunction with CMV promoters. The bicistronic expression cassette contains a furin recognition site and a 2A linker sequence separating the ORF containing the FI6 VL and CL regions from the ORF containing the FI6 heavy chain. The polyA for the expression cassette on the right is a shortened thymidine kinase polyA. The polyA for the expression cassette on the left is a synthetic polyA sequence.
Figure 4B:
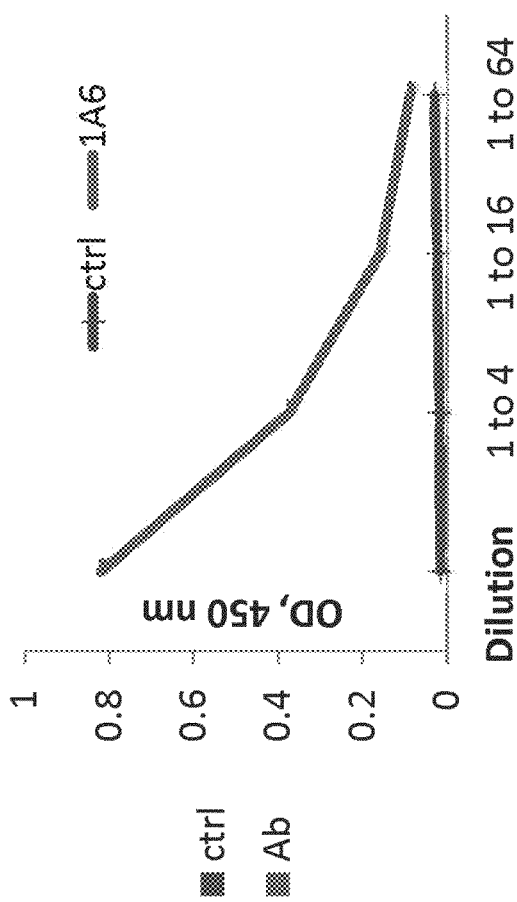
FIGS. 4A-4B illustrates the binding ability of an FI6v3k2 antibody co-expressed with a 1A6 antibody (anti-TSG 101) from a recombinant AAV8 prepared as described herein.
Figure 4A:
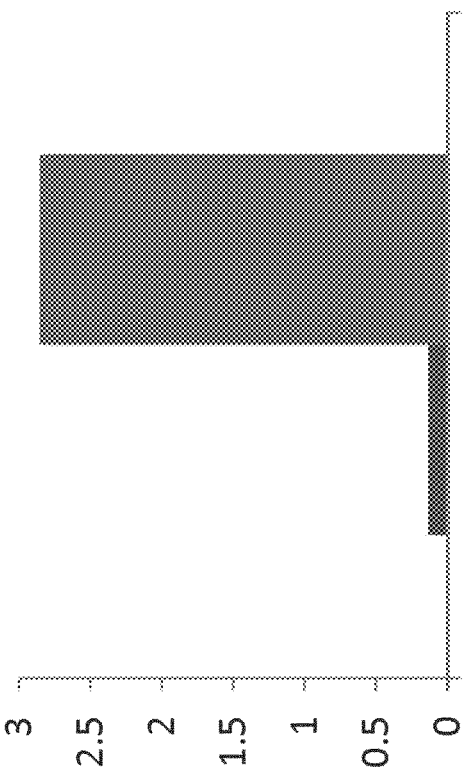

An exemplary antibody co-expression shuttle is illustrated in FIG. 2. This shuttle contains to the left of the enhancer a first expression cassette which contains, from right to left, a CMV minimal promoter, a heterologous IL2 leader sequence linked to an anti-TSG101 antibody (1A6) variable heavy (VH) domain, a CH'1 domain, and a CH'2-3 domain which has been optimized for expression in humans, and a synthetic polyA. To the right of the enhancer is located a CMV minimal promoter, a heterologous IL2 leader sequence, a FI6k2 (anti-influenza antibody) light chain variable domain and a light chain constant domain, furin cleavage site, the 2a linker from the foot-and-mouth disease virus, an IL2 leader sequence, the FI6v3 VH, CH1, CH2-3, and a thymidine kinase short polyA sequence. CH designations refer to the known antibody allotype G1m17,1.

SEQ ID NO: 1 provides sequences of the FI6 constant regions. The amino acid sequences of the FI6 amino acid light chain is provided in SEQ ID NO: 2.

The cis-plasmid of FIG. 2 was used in a triple transfection method as previously described in, e.g., in U.S. patent application Ser. No. 12/226,558, to generate AAV8 and AAV9 vectors which were used in subsequent studies described herein. The resulting plasmid, pN509_ACE Fi6-1A6 MAB_p3160, is 7722 bp in length, the sequence of which is provided in SEQ ID NO: 3, which is incorporated herein by reference together with its features. The encoded sequences for the FI6 variable light (VL) chain [SEQ ID NO:4], FI6 variable heavy [SEQ ID NO: 5], CH1 (SEQ ID NO: 6), CH2-3 [SEQ ID NO: 7] are also provided.

Similar antibody co-expression cis-plasmids were generated by subcloning a seasonal flu antibody (CR8033) or a pandemic flu antibody (C05), or an anti-M2e antibody (TCN-032) in the place of 1A6 heavy variable domain in FIG. 2 using pre-positioned unique restriction sites that allow easy shuffling of the variable domains. These cis-plasmids were in turn used in triple transfection (e.g., performed as described in U.S. patent application Ser. No. 12/226,588) to generate AAV8 and AAV9 vectors used for subsequent studies. Sequences for the pN510_ACE Fi6-C05 MAB shuttle are provided in SEQ ID NO:8; the amino acids sequence of the variable light chain is provided in SEQ ID NO: 9, the constant light is provided in SEQ ID NO: 10, the FI6 variable heavy chain is provided in SEQ ID NO: 11, the CH1 is provided in SEQ ID NO:12 and the CH2-3 is provide in SEQ ID NO: 13. Sequences for the pN514_ACE Fi6-005 MAB shuttle are provided in SEQ ID NO:19; the amino acids sequence of the constant light is provided in SEQ ID NO: 20, the FI6 variable heavy chain is provided in SEQ ID NO: 21, the CH1 is provided in SEQ ID NO:22 and the CH2-3 is provide in SEQ ID NO: 23. These shuttles were in turn used to generate AAV8 and AAV9 vectors which were used for subsequent studies.

Example 2: Characterization of Products Expressed From AAV8 Vectors Co-Expressing F16 Monoclonal Antibody (MAB) and IA6 MAB A series of ELISA assays were performed to characterize expression levels and to assess binding of the FI6 MAB co-expressed with the IA6 MAB from the cis plasmid generated as described in Example 1 after transfection into HEK 293 cells. TSG101 peptide was synthesized using f-Moc chemistry by Mimotopes. All flu antigens were procured from a commercial supplier, ImmuneTechnologies, Inc. ProteinA was purchased from Sigma-Aldrich and was used to monitor expression of total human IgG1. Detection of human IgG1 in tissue culture supernatants was measured by either antigen-specific or proteinA capture ELISA. High binding ELISA plates were coated with 2 µg/ml of HA proteins or peptides, or with 5 µg/ml proteinA diluted in PBS and incubated overnight at 4° C. Wells were washed 5-8 times and blocked with 1 mM EDTA, 5% heat inactivated PBS, 0.07% Tween 20 in PBS for one hour at room temperature. Tissue culture supernatants were added to the plates at various dilutions in duplicates and incubated at 37° C. for one hour. Plates were washed, blocked, and Bio-SP-conjugated Affinipures Goat Anti-Human IgG antibody (Jackson ImmunoResearch Laboratories, Inc., West Grove, Pa., USA) was added at a 1:10,000 dilution. After one hour, plates were washed and streptavidin-conjugated horseradish peroxidase (HRP) was added at a 1:30,000 dilution. After one hour, plates were washed 3,3',5,5'-tetramethylbenzidine (TMB) was added. The reaction was stopped after 30 minutes at room temperature using 2N sulfuric acid and plates were read at 450 nm using a BioTek μQuant plate reader (Winooski, Vt., USA).

As expected, no binding is observed of FI6 to the TSG101 peptide, the HA (B/Malaysia/2506/2/004), or the HA (Head region only of influenza strain A/Brisbane/59/2007). FI6 binding is observed for this same strain of influenza when the full-length HA is present, as well as for influenza strain HA(dTM)(A/Beijing/01/2009, H1N1)). As expected, FI6 binding is also observed for Protein A.

According to published reports, FI6 produced according to prior art methods binds to full-length HA and to HA stem, but not to the head only region. These data demonstrate that the co-expressed FI6 monoclonal antibody retains its characteristic binding profile.

Example 3: Characterization of Products Expressed From AAV8 Vectors Co-Expressing FI6 Monoclonal Antibody (MAB) and Pandemic Flu MAB C05

The possibility of differential detection of two different monoclonal antibodies was assessed in a capture assay. Monoclonal antibodies FI6 and C05 co-expressed from a cis-plasmid prepared as described in Example 1 and transfected into HEK293 cells were assessed for binding. FI6 is expected to bind to full-length HA and to HA stem, but not to the head only region. The results of the binding study illustrated in FIG. 3 demonstrate that the co-expressed antibodies retain their characteristic binding. More particularly, binding to full-length HA and the HA stem characteristic of FI6 is observed and binding to HA and HA head only (no stem) characteristic of C05 is also observed. ELISA assays were performed as described in Example 2.

Example 4: Characterization of Products Expressed From AAV8 Vectors Co-Expressing FI6 Monoclonal Antibody (MAB) and a Second Full-Length MAB 6-8 weeks old male RAG KO mice (The Jackson Laboratory Bar Harbor, Me., USA) were housed under pathogen-free conditions at the University of Pennsylvania's Translational Research Laboratories. All animal procedures and protocols were approved by the Institutional Animal Care and Use Committee. Mice were sacrificed by carbon dioxide asphyxiation and death was confirmed by cervical dislocation. For vector administration, mice were anaesthetized with a mixture of 70 mg/kg of body weight ketamine and 7 mg/kg of body weight xylazine by intraperitoneal (IP) injection. Vectors were diluted in phosphate buffered saline (PBS) and IM injections were performed using a Hamilton syringe. Serum was collected weekly via retro-orbital bleeds. Detection of human IgG1 in tissue culture supernatants was measured by proteinA capture ELISA. High binding ELISA plates were coated with 5 μg/ml proteinA diluted in PBS and incubated overnight at 4° C. Wells were washed 5-8 times and blocked with 1 mM EDTA, 5% heat inactivated PBS, 0.07% Tween 20 in PBS. Mouse serum samples were heat inactivated and added to the plates at various dilutions in duplicates and incubated at 37° C. for one hour. Plates were washed, blocked, and Bio-SP-conjugated Affinipures Goat Anti-Human IgG antibody (Jackson ImmunoResearch Laboratories, Inc., West Grove, Pa., USA) was added at a 1:10,000 dilution. After one hour, plates were washed and incubated with streptavidin-conjugated horseradish peroxidase (HRP) at a 1:30,000 dilution. After one hour, plates were washed 3,3',5,5'-tetramethylbenzidine (TMB) was added. The reaction was stopped after 30 minutes at room temperature using 2N sulfuric acid and plates were read at 450 nm using a BioTek μQuant plate reader (Winooski, Vt., USA).

FIG. 5 illustrates systemic expression levels for total human IgG1 in mice administered an AAV vector co-expressing FI6 with IA6 antibody. Mice were injected intramuscularly at doses of $1 \times 10^{11}$ genome copies (GC) or $1 \times 10^{10}$ GC. Expression levels were assessed at day 7, 15, 21, 28, 34, 42, 49 and 56 and measured at a concentration of micrograms/mL. A dose dependent increase in expression was observed.

Example 5: Characterization of Products Expressed From AAV8 Vectors Co-Expressing FI6 Monoclonal Antibody (MAB) and Three Different Full-Length Monoclonal Antibodies The tables below showing expression levels in mice administered an AAV vector co-expressing FI6 with full-length CR8033, C05, or 1A6 monoclonal antibody. RAG knock-out (KO) mice were injected intramuscularly at doses of $1 \times 10^{11}$ genome copies (GC) or $1 \times 10^{10}$ GC as described in the previous example. Expression levels were assessed weekly at days 7, 15, 21, 28, 34, 42, and 49 and measured at a concentration of micrograms/mL. A dose dependent increase in expression was observed for expressed antibodies. The capture antigen used for the assay is Protein A ELISA as described in the previous example

| | Test Article Fi6v3k2 mAb + CR8033 mAb Dose | | | |
|---|---|---|---|---|
| | $1.00 \times 10^{11}$ | | $1.00 \times 10^{10}$ | |
| | average | stdev. | average | stdev. |
| Day 0 | 0.00 | 0.00 | 0.00 | 0.00 |
| Day 7 | 2.92 | 0.48 | 0.04 | 0.07 |
| Day 14 | 18.30 | 4.79 | 1.24 | 0.66 |
| Day 21 | 33.69 | 7.45 | 2.09 | 0.88 |
| Day 28 | 43.38 | 10.92 | 2.84 | 1.81 |
| Day 35 | 66.45 | 16.61 | 4.47 | 1.86 |
| Day 42 | 64.25 | 12.06 | 4.37 | 2.35 |
| Day 49 | 51.36 | 11.90 | 3.57 | 1.52 |

| | Test Article Fi6v3k2 mAb + CO5 mAb Dose | | | |
|---|---|---|---|---|
| | $1.00 \times 10^{11}$ | | $1.00 \times 10^{10}$ | |
| | average | stdev. | average | stdev. |
| Day 0 | 0.00 | 0.00 | 0.00 | 0.00 |
| Day 7 | 1.73 | 0.42 | 0.00 | 0.00 |
| Day 14 | 9.95 | 3.39 | 0.24 | 0.22 |
| Day 21 | 24.74 | 11.66 | 0.81 | 0.24 |
| Day 28 | 22.32 | 4.77 | 1.11 | 0.17 |
| Day 35 | 31.67 | 7.93 | 1.53 | 0.28 |
| Day 42 | 34.69 | 14.46 | 1.83 | 0.29 |
| Day 49 | 26.14 | 5.85 | 1.46 | 0.49 |

| | Test Article Fi6v3k2 mAb + 1A6 mAb Dose | | | |
|---|---|---|---|---|
| | $1.00 \times 10^{11}$ | | $1.00 \times 10^{10}$ | |
| | average | stdev. | average | stdev. |
| Day 0 | 0 | 0 | 0 | 0 |
| Day 7 | 2.70 | 0.75 | 0 | 0 |
| Day 14 | 5.01 | 0.06 | 1.58 | .055 |
| Day 21 | 30.16 | 13.31 | 1.71 | 0.52 |
| Day 28 | 38.18 | 15.99 | 2.16 | 0.59 |
| Day 35 | 55.18 | 18.52 | 4.09 | 1.53 |
| Day 42 | 50.49 | 16.61 | 3.69 | 0.94 |
| Day 49 | 46.66 | 15.59 | 3.73 | 1.09 |

Figure 6B:
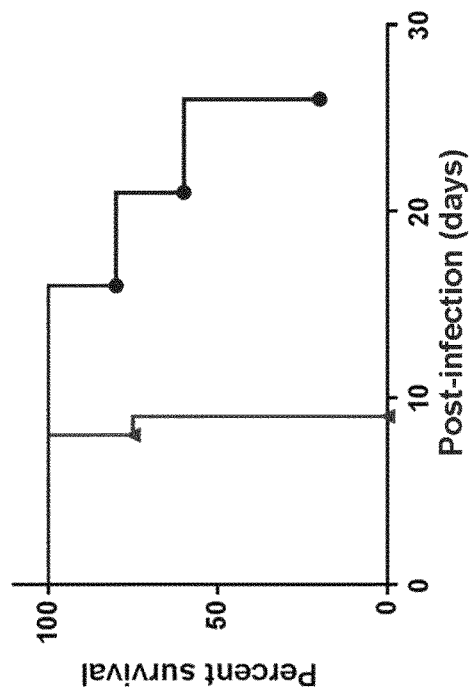
FIGS. 6A-6B illustrate the evaluation of the AAV9.BiD.FI6v3_CR8033mAb delivered intramuscularly (IM) at $1\times10^{11}$ GC for protection against challenge with influenza strain PR8.
Figure 6A:
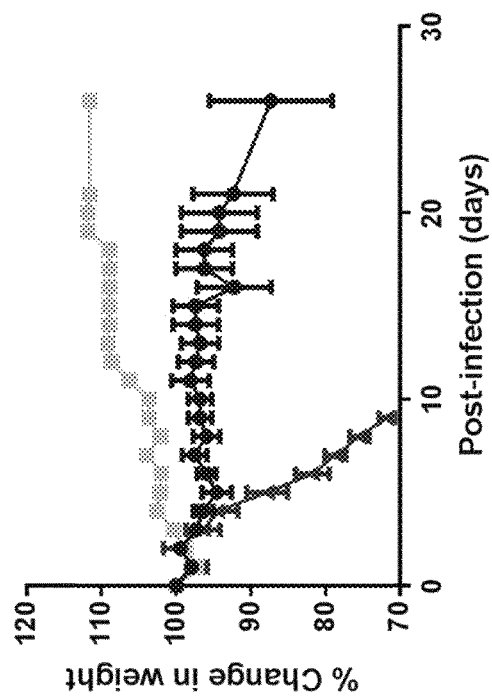

Example 6: Anti-Viral Effect is Conferred by Dual Full-Length Antibodies Expressed from a Single AAV9 and/or AAV8 Vector Intramuscularly A. AAV9.BiD.FI6_CR8033mAb and Influenza A Challenge BALB/c mice were injected with AAV9.BiD.FI6_CR8033mAb delivered intramuscularly (IM) at $1\times10^{11}$ GC. Two weeks later the mice were challenged intranasally with 5LD50 of mouse adapted PR8 (influenza A). The circle represents the AAV9 construct with a bidirectional promoter expressing synthetic FI6 and CR8033 monoclonal antibodies having the same heterologous light chain. The square represents a positive control, i.e., AAV9 expressing a single antibody type FI6 also delivered at $1\times10^{11}$ GC, and the triangle represents naïve animals. FIG. 6B shows survival post-challenge. Administration of the AAV9.BiD.FI6_CR8033mAb at $10^{11}$ GC/mouse dose allowed partial protection with a significant delay in the weight loss.

B. AAV9.BiD.FI6_CR8033mAb and Influenza B Challenge

Figure 7B:
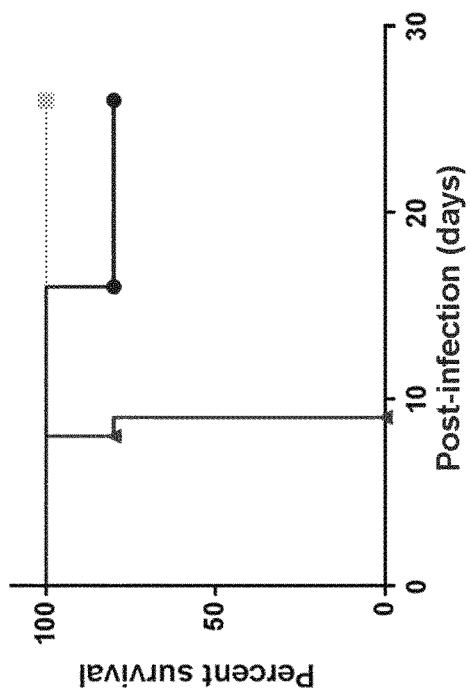
FIGS. 7A-7B illustrate the evaluation of the AAV9.BiD.FI6v3_CR8033mAb delivered intramuscularly (IM) at $1\times10^{11}$ GC for protection against challenge with influenza strain B/Lee/40.

For AAV9 vector injection: BALB/c female mice were anesthetized by an intramuscular injection of a 100 mg/kg ketamine/10 mg/kg xylazine mixture in PBS, and AAV9.BiD.FI6_CR8033mAb vector was injected intramuscularly (IM) at $1\times10^{11}$ GC per mouse. BiD vector was compared to an AAV9 expressing a single antibody type CR8033 also delivered at $1\times10^{11}$ GC, and a negative control (naïve animals). FIG. 7B shows survival post-challenge. For influenza challenge, two weeks after vector treatment, AAV-treated and naïve BALB/c mice were weighed and tails color-coded, anesthetized as described above, suspended by their dorsal incisors with their hind limbs supported on a platform, and administered intranasally with 5LD50 of B/Lee/40 (influenza B) in a total volume of 50 µl of PBS as described above. Mice were then weighed daily and monitored for signs of disease or distress. Animals that exhibited behavioral signs of distress or lost 30% of their initial body weight were euthanized by CO2 asphyxiation.

Figure 7A:
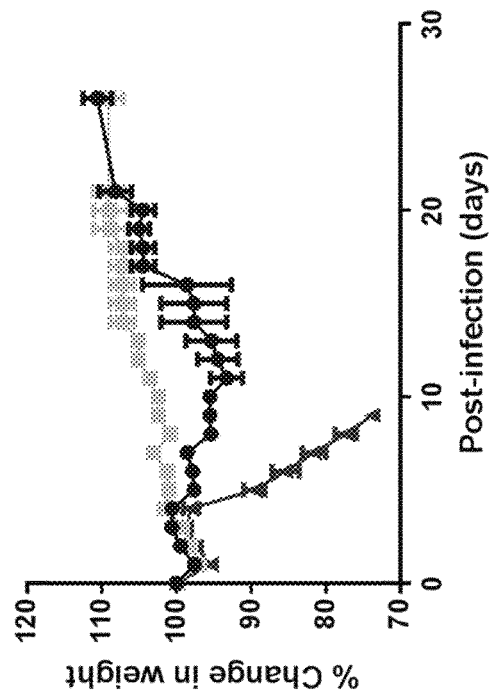

FIG. 7A is a line graph showing percent change in weight. These data show that full protective effect was conferred by the dual expressed antibodies at this dose. FIG. 7B shows survival post-challenge.

C. AAV8.F16-TCN032, AAV8. F16-1A6, and AAV8. F16-CR8033 vectors administered IM and mouse adapted PR8 Influenza A challenge.

These vectors were made as described in Example 1. 6-8 weeks old male RAG KO mice (The Jackson Laboratory Bar Harbor, Me., USA) were housed under pathogen-free conditions at the University of Pennsylvania's Translational Research Laboratories. All animal procedures and protocols were approved by the Institutional Animal Care and Use Committee. For vector administration, mice were anaesthetized with a mixture of 70 mg/kg of body weight ketamine and 7 mg/kg of body weight xylazine by intraperitoneal (IP) injection. Vectors were diluted in phosphate buffered saline (PBS) and IM injections were performed using a Hamilton syringe. Serum was collected weekly via retro-orbital bleeds.

Detection of human IgG1 in tissue culture supernatants was measured by proteinA capture ELISA. High binding ELISA plates were coated with 5 µg/ml proteinA diluted in PBS and incubated overnight at 4° C. Wells were washed 5-8 times and blocked with 1 mM EDTA, 5% heat inactivated PBS, 0.07% Tween 20 in PBS. Mouse serum samples were heat inactivated and added to the plates at various dilutions in duplicates and incubated at 37° C. for one hour. Plates were washed, blocked, and Bio-SP-conjugated Affinipures Goat Anti-Human IgG antibody (Jackson ImmunoResearch Laboratories, Inc., West Grove, Pa., USA) was added at a 1:10,000 dilution. After one hour, plates were washed and incubated with streptavidin-conjugated horseradish peroxidase (HRP) at a 1:30,000 dilution. After one hour, plates were washed 3,3',5,5'-tetramethylbenzidine (TMB) was added. The reaction was stopped after 30 minutes at room temperature using 2N sulfuric acid and plates were read at 450 nm using a BioTek µQuant plate reader (Winooski, Vt., USA).

With reference to FIG. 8C, on all panels, expression levels are indicated on Day 56 after vector administration. Couple days after the last orbital bleed on Day 56, mice were weighed and tails color-coded, anesthetized as described above, suspended by their dorsal incisors with their hind limbs supported on a platform, and administered intranasally with $5LD_{50}$ of mouse adapted PR8 (influenza A) in a total volume of 50 µl of PBS as described above. Mice were then weighed daily and monitored for signs of disease or distress. Animals that exhibited behavioral signs of distress or lost 30% of their initial body weight were euthanized by $CO_2$ asphyxiation and death was confirmed by cervical dislocation. FIG. 8A shows that systemic expression of as little as 25 µl g/ml of anti-influenza antibody is sufficient to afford protection in PR8 challenge, but expression of 0.4 µg/ml is insufficient for protection.

D. AAV9. FI6_IA6 mAbs and Influenza A Challenge

An AAV9 vector expressing artificial FI6 and an anti-HIV immunoadhesin, IA6, were assessed for protection against challenge with influenzA A as described above. FIG. 8B shows that expressing 36.5 µg/ml of anti-influenza antibody is sufficient to provide complete protection against challenge with PR8. FIG. 8C shows expressing 6.9 ug/ml of anti-influenza antibodies is not sufficient to protect against PR8 challenge.

Example 7: Generation of Vectors Containing Two Immunoadhesin Co-Expression Cassettes Using a shuttle vector similar to that illustrated in FIG. 2, vectors containing two immunoadhesins have been generated.

In one embodiment, a vector containing FI6 and C05 immunoadhesins was created. The sequences from a plasmid carrying the FI6 and C05 immunoadhesin expression cassettes are provided in SEQ ID NO: 36; with the translated encoded sequences provided in SEQ ID NO: 37 (FI6 variable heavy chain), SEQ ID NO: 38 (FI6 variable light chain), and SEQ ID NO: 39 (CH2-3). These sequences and their features are incorporated by reference.

In another embodiment, a vector containing FI6 and CR8033 immunoadhesins was created. The sequences from a plasmid containing the FI6 and CR8033 immunoadhesins are provided in SEQ ID NO:40; with the translated encoded sequences provided in SEQ ID NO: 41 (FI6 VH) and SEQ ID NO: 42 (FI6 variable light). These sequences and their features are incorporated by reference.

AAV may be generated from the immunoadhesin shuttle plasmids described above using techniques known to those of skill in the art.

Additional illustrative shuttle plasmids are as follows.

The sequence of a plasmid pN512_ACE FI6v3kg1-1A6 MAB_p3184 containing a kappa germline light chain that is heterologous to the source of both heavy chains, 1A6 and FI6v3 is provided in SEQ ID NO: 14. The translated encode sequences are provide in SEQ ID NO: 15 (constant light), SEQ ID NO: 16 (FI6 variable heavy), SEQ ID NO: 17 (CH1), and SEQ ID NO: 18 (CH2-3).

The sequences of an intermediate vector which carries the TCN032 heavy and light chain immunoglobulins are provided in SEQ ID NO: 30. The translated amino acid sequences encoded by this plasmid include the TCN032 heavy chain in SEQ ID NO: 31; the CH1 sequence in SEQ ID NO: 32; the F16 VH chain in SEQ ID NO: 33; the CH1 sequence in SEQ ID NO: 34 and the CH2-3 sequence in SEQ ID NO: 35.

The sequence of a plasmid carrying the TCN032 and F16 heavy chains and co-expressing two antibodies having these specificities is provided in SEQ ID NO: 43. The translated amino acids of the TCN032 variable heavy chain are in SEQ ID NO: 44, the CH1 is in SEQ ID NO: 45, the hinge-CH2'-CH3' is in SEQ ID NO: 46, the Fi6 VH is in SEQ ID NO: 47, the CH1 is in SEQ ID NO: 48, the CH2-3 is in SEQ ID NO: 49, and the ampicillin resistance gene is in SEQ ID NO: 50. These sequences and their features are incorporated herein by reference.

SEQUENCE LISTING FREE TEXT

The following information is provided for sequences containing free text under numeric identifier <223>.

| SEQ ID NO: (containing free text) | Free text under <223> |
|---|---|
| 1 | <223> Synthetic sequence encoding FI6 heavy chain |
| | <220> <221> CDS <222> (1) . . . (705) <223> FI6 constant |
| 3 | <223> plasmid carrying FI6 and 1A6 antibodies |
| | <220> <221> polyA_signal <222> (191) . . . (239) <223> synthetic\polyA |
| | <220> <221> misc_feature <222> (246) . . . (914) <223> complement - CH'2-3 |

-continued

| SEQ ID NO: (containing free text) | Free text under <223> |
|---|---|
| | <220> <221> misc_feature <222> (915) . . . (1235) <223> complement - CH'1 |
| | <220> <221> misc_feature <222> (1236) . . . (1598) <223> complement - 1A6/VH |
| | <220> <221> misc_feature <222> (1599) . . . (1655) <223> complement - leader |
| | <220> <221> misc_feature <222> (1734) . . . (2202) <223> Enhancer |
| | <220> <221> misc_feature <222> (2388) . . . (2444) <223> leader |
| | <220> <221> CDS <222> (2445) . . . (2777) <223> FI6\VL |
| | <220> <221> misc_feature <222> (3183) . . . (3242) <223> leader |
| | <220> <221> CDS <222> (3243) . . . (3629) <223> FI6\VH |
| | <220> <221> CDS <222> (3630) . . . (3950) <223> CH1 |
| | <220> <221> CDS <222> (3951) . . . (4619) <223> CH2-3 |
| | <220> <221> polyA_signal <222> (4626) . . . (4703) <223> TKpAshort |
| | <220> <221> misc_feature <222> (6995) . . . (7283) <223> COL\E1\Origin |
| 8 | <223> Plasmid encoding FI6 and C05 monoclonal antibodies |
| | <220> <221> polyA_signal <222> (204) . . . (252) <223> synthetic\polyA |
| | <220> <221> misc_feature <222> (259) . . . (927) <223> complement - CH'2-3 |

| SEQ ID NO: (containing free text) | Free text under <223> |
|---|---|
| | <220><br><221> misc_feature<br><222> (928) . . . (1248)<br><223> complement - CH'1 |
| | <220><br><221> misc_feature<br><222> (1251) . . . (1668)<br><223> complement - C05\VH |
| | <220><br><221> misc_feature<br><222> (1669) . . . (1719)<br><223> complement - leader |
| | <220><br><221> misc_feature<br><222> (1729) . . . (1979)<br><223> complement - CMV\mp2 |
| | <220><br><221> misc_feature<br><222> (1798) . . . (2266)<br><223> Enhancer |
| | <220><br><221> misc_feature<br><222> (2267) . . . (2392)<br><223> CMV\mp2 |
| | <220><br><221> CDS<br><222> (2509) . . . (2841)<br><223> FI6\VL |
| | <220><br><221> CDS<br><222> (2842) . . . (3162)<br><223> CL |
| | <220><br><221> misc_feature<br><222> (3247) . . . (3306)<br><223> leader |
| | <220><br><221> CDS<br><222> (3307) . . . (3693)<br><223> FI6/VH |
| | <220><br><221> CDS<br><222> (3694) . . . (4014)<br><223> CH1 |
| | <220><br><221> CDS<br><222> (4015) . . . (4683)<br><223> CH2-3 |
| | <220><br><221> polyA_signal<br><222> (4690) . . . (4767)<br><223> TKpAshort |
| 14 | <223> Plasmid encoding synthetic FI6 and 1A6 monoconals |
| | <220><br><221> polyA_signal<br><222> (191) . . . (239)<br><223> synthetic\polyA |

| SEQ ID NO: (containing free text) | Free text under <223> |
|---|---|
| | <220><br><221> misc_feature<br><222> (246) . . . (914)<br><223> complement - CH'2-3 |
| | <220><br><221> misc_feature<br><222> (915) . . . (1235)<br><223> complement - CH'1 |
| | <220><br><221> misc_feature<br><222> (1236) . . . (1598)<br><223> complement - 1A6\VH |
| | <220><br><221> misc_feature<br><222> (1599) . . . (1655)<br><223> complement - leader |
| | <220><br><221> misc_feature<br><222> (1665) . . . (1733)<br><223> complement - CMV\mp2 |
| | <220><br><221> misc_feature<br><222> (1732) . . . (2202)<br><223> Enhancer |
| | <220><br><221> misc_feature<br><222> (2203) . . . (2328)<br><223> CMV\mp1 |
| | <220><br><221> misc_feature<br><222> (2388) . . . (2444)<br><223> leader |
| | <220><br><221> misc_feature<br><222> (2445) . . . (2789)<br><223> KGL |
| | <220><br><221> CDS<br><222> (2784) . . . (3104)<br><223> CL |
| | <220><br><221> misc_feature<br><222> (3189) . . . (3248)<br><223> leader |
| | <220><br><221> CDS<br><222> (3249) . . . (3635)<br><223> FI6\VH |
| | <220><br><221> CDS<br><222> (3636) . . . (3956)<br><223> CH1 |
| | <220><br><221> CDS<br><222> (3957) . . . (4625)<br><223> CH2-3 |

| SEQ ID NO: (containing free text) | Free text under <223> |
|---|---|
| | <220><br><221> polyA_signal<br><222> (4632) . . . (4709)<br><223> TKpAshort |
| 19 | <223> Plasmid carrying FI6 and CR8033 monoclonals<br><br><220><br><221> polyA_signal<br><222> (173) . . . (221)<br><223> synthetic\polyA<br><br><220><br><221> misc_feature<br><222> (228) . . . (896)<br><223> complement - CH'2-3<br><br><220><br><221> misc_feature<br><222> (897) . . . (1217)<br><223> complement - CH'1<br><br><220><br><221> misc_feature<br><222> (1218) . . . (1604)<br><223> complement - CR8033\VH<br><br><220><br><221> misc_feature<br><222> (1605) . . . (1655)<br><223> complement - leader<br><br><220><br><221> misc_feature<br><222> (1665) . . . (1733)<br><223> complement - CMV\mp2<br><br><220><br><221> misc_feature<br><222> (1734) . . . (2202)<br><223> Enhancer<br><br><220><br><221> misc_feature<br><222> (2203) . . . (2328)<br><223> CMV\mp1<br><br><220><br><221> misc_feature<br><222> (2445) . . . (2789)<br><223> KGL<br><br><220><br><221> CDS<br><222> (2784) . . . (3104)<br><223> CL<br><br><220><br><221> misc_feature<br><222> (3189) . . . (3248)<br><223> leader<br><br><220><br><221> CDS<br><222> (3249) . . . (3635)<br><223> FI6\VH<br><br><220><br><221> CDS<br><222> (3636) . . . (3956)<br><223> CH1 |

| SEQ ID NO: (containing free text) | Free text under <223> |
|---|---|
| | <220><br><221> CDS<br><222> (3957) . . . (4625)<br><223> CH2-3<br><br><220><br><221> misc_feature<br><222> (3968) . . . (3968)<br><223> A -> T<br><br><220><br><221> polyA_signal<br><222> (4632) . . . (4709)<br><223> TKpAshort |
| 24 | <223> Plasmid carrying FI6 and CR8033 monoclonal antibodies<br><br><220><br><221> polyA_signal<br><222> (191) . . . (239)<br><223> synthetic polyA<br><br><220><br><221> misc_feature<br><222> (246) . . . (914)<br><223> complement - CH'2-3<br><br><220><br><221> misc_feature<br><222> (915) . . . (1235)<br><223> complement - CH'1<br><br><220><br><221> misc_feature<br><222> (1236) . . . (1622)<br><223> complement - CR8033\VH<br><br><220><br><221> misc_feature<br><222> (1623) . . . (1673)<br><223> complement - leader<br><br><220><br><221> misc_feature<br><222> (1683) . . . (1751)<br><223> CMV\mp2<br><br><220><br><221> misc_feature<br><222> (1752) . . . (2220)<br><223> Enhancer<br><br><220><br><221> misc_feature<br><222> (2221) . . . (2346)<br><223> CMV\mp1<br><br><220><br><221> misc_feature<br><222> (2406) . . . (2462)<br><223> leader<br><br><220><br><221> CDS<br><222> (2463) . . . (2795)<br><223> FI6\VL<br><br><220><br><221> CDS<br><222> (2796) . . . (3116)<br><223> CL |

| SEQ ID NO: (containing free text) | Free text under <223> |
|---|---|
| | <220><br><221> misc_feature<br><222> (3201) . . . (3260)<br><223> leader |
| | <220><br><221> CDS<br><222> (3261) . . . (3647)<br><223> FI6\VH |
| | <220><br><221> CDS<br><222> (3648) . . . (3968)<br><223> CH1 |
| | <220><br><221> CDS<br><222> (3969) . . . (4637)<br><223> CH2-3 |
| | <220><br><221> misc_feature<br><222> (3980) . . . (3980)<br><223> A -> T |
| | <220><br><221> polyA_signal<br><222> (4644) . . . (4721)<br><223> TKpAshort |
| 30 | <223> EcoRV |
| | <220><br><221> polyA_signal<br><222> (201) . . . (252)<br><223> complement - synthetic\polyA |
| | <220><br><221> misc_feature<br><222> (268) . . . (588)<br><223> complement - CL |
| | <220><br><221> misc_feature<br><222> (589) . . . (909)<br><223> complement - TCN032\VL |
| | <220><br><221> polyA_signal<br><222> (910) . . . (966)<br><223> complement - leader |
| | <220><br><221> misc_feature<br><222> (1026) . . . (1094)<br><223> complement - CMV\mp2 |
| | <220><br><221> misc_feature<br><222> (1095) . . . (1563)<br><223> Enhancer |
| | <220><br><221> misc_feature<br><222> (1564) . . . (1689)<br><223> CMV\mp1 |
| | <220><br><221> misc_feature<br><222> (1749) . . . (1805)<br><223> leader |

| SEQ ID NO: (containing free text) | Free text under <223> |
|---|---|
| | <220><br><221> CDS<br><222> (1806) . . . (2165)<br><223> TCN032\VH |
| | <220><br><221> CDS<br><222> (2166) . . . (2459)<br><223> CH1 |
| | <220><br><221> misc_feature<br><222> (2460) . . . (3152)<br><223> hinge-CH2'—CH3' |
| | <220><br><221> misc_feature<br><222> (3239) . . . (3296)<br><223> leader |
| | <220><br><221> CDS<br><222> (3297) . . . (3683)<br><223> FI6\VH |
| | <220><br><221> CDS<br><222> (3684) . . . (4004)<br><223> CH1 |
| | <220><br><221> CDS<br><222> (4005) . . . (4673)<br><223> CH2-3 |
| | <220><br><221> polyA_signal<br><222> (4693) . . . (4770)<br><223> TKpAshort |
| 36 | <223> FI6 and C05 immunoadhesins |
| | <220><br><221> polyA_signal<br><222> (201) . . . (432)<br><223> complement - SV40\polyA |
| | <220><br><221> misc_feature<br><222> (453) . . . (1121)<br><223> complement - CH'2-3 |
| | <220><br><221> misc_feature<br><222> (1125) . . . (1457)<br><223> complement - C05\VL |
| | <220><br><221> misc_feature<br><222> (1458) . . . (1502)<br><223> SL\from\3bn201co |
| | <220><br><221> misc_feature<br><222> (1503) . . . (1916)<br><223> complement - C05\VH |
| | <220><br><221> misc_feature<br><222> (1965) . . . (1973)<br><223> leader |

| SEQ ID NO: (containing free text) | Free text under <223> |
|---|---|
| | <220><br><221> misc_feature<br><222> (2371) . . . (2412)<br><223> complement - CMV\mp2 |
| | <220><br><221> misc_feature<br><222> (2413) . . . (2881)<br><223> enhancer |
| | <220><br><221> misc_feature<br><222> (2882) . . . (3007)<br><223> CMV\mp1 |
| | <220><br><221> misc_feature<br><222> (3067) . . . (3055)<br><223> leader |
| | <220><br><221> CDS<br><222> (3124) . . . (3510)<br><223> FI6\VH |
| | <220><br><221> misc_feature<br><222> (3511) . . . (3555)<br><223> SL\from\3bn201co |
| | <220><br><221> CDS<br><222> (3556) . . . (3888)<br><223> FI6\VL |
| | <220><br><221> CDS<br><222> (3892) . . . (4560)<br><223> CH2-3 |
| | <220><br><221> polyA_signal<br><222> (4581) . . . (4812)<br><223> SV40\polyA |
| 40 | <223> FI6 and CR8033 immunoadhesins |
| | <220><br><221> polyA_signal<br><222> (201) . . . (432)<br><223> complement - SV40\polyA |
| | <220><br><221> misc_feature<br><222> (453) . . . (1121)<br><223> complement - CH'2-3 |
| | <220><br><221> misc_feature<br><222> (1125) . . . (1460)<br><223> complement - 033\VL |
| | <220><br><221> misc_feature<br><222> (1461) . . . (1505)<br><223> SL\from\3bn201co |
| | <220><br><221> misc_feature<br><222> (1506) . . . (1886)<br><223> complement - 033\VH |

| SEQ ID NO: (containing free text) | Free text under <223> |
|---|---|
| | <220><br><221> misc_feature<br><222> (1935) . . . (1946)<br><223> complement - leader |
| | <220><br><221> misc_feature<br><222> (2341) . . . (2382)<br><223> complement - CMV\mp2 |
| | <220><br><221> misc_feature<br><222> (2383) . . . (2851)<br><223> enhancer |
| | <220><br><221> misc_feature<br><222> (2852) . . . (2977)<br><223> CMV\mp1 |
| | <220><br><221> misc_feature<br><222> (3073) . . . (3045)<br><223> leader |
| | <220><br><221> CDS<br><222> (3094) . . . (3480)<br><223> FI6\VH |
| | <220><br><221> misc_feature<br><222> (3481) . . . (3525)<br><223> SL\from\3bn201co |
| | <220><br><221> CDS<br><222> (3526) . . . (3858)<br><223> FI6\VL |
| | <220><br><221> misc_feature<br><222> (3862) . . . (4530)<br><223> CH2-3 |
| | <220><br><221> polyA_signal<br><222> (4551) . . . (4782)<br><223> SV40\polyA |
| 43 | <223> Plasmid carrying TCN032 and Fi6 monoclonal antibodies |
| | <220><br><221> repeat_region<br><222> (14) . . . (143) |
| | <220><br><221> polyA_signal<br><222> (204) . . . (252)<br><223> synthetic polyA |
| | <220><br><221> misc_feature<br><222> (261) . . . (267)<br><223> stop cassette (complement) |
| | <220><br><221> misc_feature<br><222> (268) . . . (588)<br><223> constant light (on complementary strand) |

| SEQ ID NO: (containing free text) | Free text under <223> |
|---|---|
| | <220><br><221> misc_feature<br><222> (967) . . . (971)<br><223> Kozak (located on complementary strand)<br><br><220><br><221> misc_feature<br><222> (972) . . . (1019)<br><223> c-myc 5' UTR (located on complementary strand)<br><br><220><br><221> misc_feature<br><222> (1026) . . . (1094)<br><223> CMV\mp2<br><br><220><br><221> enhancer<br><222> (1026) . . . (1094)<br><br><220><br><221> misc_feature<br><222> (1564) . . . (1689)<br><br><220><br><221> misc_feature<br><222> (1696) . . . (1743)<br><223> c-myc 5' UTR<br><br><220><br><221> misc_feature<br><222> (1744) . . . (1748)<br><223> Kozak<br><br><220><br><221> misc_feature<br><222> (1749) . . . (1805)<br><223> leader<br><br><220><br><221> CDS<br><222> (1806) . . . (2165)<br><223> TCN032 variable heavy<br><br><220><br><221> repeat_region<br><222> (1845) . . . (4974)<br><223> inverted terminal repeat<br><br><220><br><221> repeat_region<br><222> (1845) . . . (4974)<br><223> inverted terminal repeat (located on complement)<br><br><220><br><221> CDS<br><222> (2166) . . . (2459)<br><223> CH1<br><br><220><br><221> misc<br><222> (2166) . . . (2459)<br><223> CH1<br><br><220><br><221> CDS<br><222> (2460) . . . (3152)<br><223> hinge-CH2'—CH3'<br><br><220><br><221> misc_feature<br><222> (3153) . . . (3164)<br><223> furin cleavage site |

| SEQ ID NO: (containing free text) | Free text under <223> |
|---|---|
| | <220><br><221> misc_feature<br><222> (3165) . . . (3236)<br><223> F2A linker<br><br><220><br><221> misc_feature<br><222> (3239) . . . (3296)<br><br><220><br><221> misc_feature<br><222> (3239) . . . (3296)<br><br><220><br><221> CDS<br><222> (3297) . . . (3683)<br><223> FI6 VH<br><br><220><br><221> CDS<br><222> (3684) . . . (4004)<br><223> CH1<br><br><220><br><221> CDS<br><222> (4005) . . . (4673)<br><223> CH2-3<br><br><220><br><221> misc_feature<br><222> (4674) . . . (4680)<br><223> Stop cassette<br><br><220><br><221> misc_feature<br><222> (4674) . . . (4680)<br><br><220><br><221> polyA_signal<br><222> (4693) . . . (4770)<br><223> TKpAshort<br><br><220><br><221> rep_origin<br><222> (5151) . . . (5606)<br><br><220><br><221> CDS<br><222> (5737) . . . (6594)<br><223> Amp-R<br><br><220><br><221> misc_feature<br><222> (6768) . . . (.7356)<br><223> col\E1\origin |

This application contains sequences and a sequence listing, which is hereby incorporated by reference. All publications, patents, and patent applications cited in this application, and U.S. Provisional Patent Application No. 61/992,649, filed May 13, 2014, the priority of which is claimed, are hereby incorporated by reference in their entireties as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

The invention claimed is:

1. A recombinant adeno-associated virus (AAV) having an AAV capsid and packaged therein a heterologous nucleic acid which expresses at least two immunoglobulins in a cell, wherein the recombinant AAV comprises:
   a 5' AAV inverted terminal repeat (ITR);
   a first expression cassette which encodes at least a first open reading frame (ORF) for a first immunoglobulin chain under the control of regulatory control sequences which direct expression thereof;
   a second expression cassette which comprises a second ORF, a linker, and a third ORF under the control of regulatory control sequences which direct expression thereof, wherein the second and third ORF are for a second and third immunoglobulin chains; and
   a 3' AAV ITR,
   wherein at least one of the expressed immunoglobulins comprises a single chain variable-fragment (scFv).

2. The recombinant AAV according to claim 1, wherein the scFv is fused to a Fc domain.

3. The recombinant AAV according to claim 1, wherein the scFv is a tandem scFv.

4. The recombinant AAV according to claim 1, wherein the scFv is a bispecific scFv.

5. The recombinant AAV according to claim 1, wherein the expressed immunoglobulin chains comprise an scFv fused to a Fc domain, an immunoglobulin light chain, and an immunoglobulin heavy chain.

6. The recombinant AAV according to claim 5, wherein the scFV is an immunoadhesin.

7. The recombinant AAV according to claim 1, wherein the first expression cassette is bicistronic and comprises a further ORF.

8. The recombinant AAV according to claim 7, wherein each of the ORFs of the first expression cassette comprise scFv coding sequences.

9. The recombinant AAV according to claim 1, wherein each of the ORFs contain scFV coding sequences.

10. The recombinant AAV according to claim 1, wherein at least one of the second and third ORF contain modified Fc coding sequences.

11. The recombinant AAV according to claim 1, wherein the linker in the second cassette comprises a linker selected from an IRES or an F2A.

12. The recombinant AAV according to claim 1, wherein the regulatory control sequences for the first expression cassette and/or the second expression cassette comprise a minimal promoter.

13. The recombinant AAV according to claim 1, wherein the regulatory control sequences for the first expression cassette and/or the second expression cassette comprise a minimal or synthetic polyA.

14. The recombinant AAV according to claim 1, wherein a bidirectional promoter is located between the first expression cassette and the second expression cassette.

15. The recombinant AAV according to claim 1, wherein the first expression cassette and/or the second expression cassette comprise an enhancer and a minimal promoter.

16. A pharmaceutical composition comprising the recombinant AAV according to claim 1 and a pharmaceutically acceptable carrier.

17. A method of delivering at least two immunoglobulins to a subject, said method comprising administering a recombinant AAV according to claim 1.

* * * * *